(12) United States Patent
Jungblut et al.

(10) Patent No.: US 7,772,386 B1
(45) Date of Patent: Aug. 10, 2010

(54) IDENTIFICATION OF SPECIFIC DIFFERENTIALLY EXPRESSED ANTIGENS

(75) Inventors: Peter Jungblut, Berlin (DE); Stefan H. E. Kaufmann, Berlin (DE); Ulrich Schaible, Berlin (DE); Hans Mollenkopf, Berlin (DE); Bärbel Raupach, Berlin (DE); Ursula Zimny-Arndt, Berlin (DE); Stephanie Lamer, Berlin (DE); Jens Mattow, Berlin (DE)

(73) Assignee: Max-Planck-Gesellschaft zur Forderung der Wissenschaften E.V., Berlin (DE)

( * ) Notice: Subject to any disclaimer, the term of this patent is extended or adjusted under 35 U.S.C. 154(b) by 0 days.

(21) Appl. No.: 09/890,339

(22) PCT Filed: Jan. 28, 2000

(86) PCT No.: PCT/EP00/00690

§ 371 (c)(1),
(2), (4) Date: Mar. 12, 2002

(87) PCT Pub. No.: WO00/44392

PCT Pub. Date: Aug. 3, 2000

(30) Foreign Application Priority Data

Jan. 29, 1999 (EP) .................................. 99101590

(51) Int. Cl.
*C07H 21/04* (2006.01)
*A61K 39/04* (2006.01)
(52) U.S. Cl. .................... 536/23.7; 536/23.1; 424/248.1
(58) Field of Classification Search .................. 424/9.1, 424/9.2, 184.1, 234.1, 248.1; 536/23.1, 23.7
See application file for complete search history.

(56) References Cited

FOREIGN PATENT DOCUMENTS

FR 2 752 425 2/1998

OTHER PUBLICATIONS

Database biosis 'Online! Bioscience information service, Philadelphia, Pa, 1998, Amara Rama Rao et al. "Characterization of novel immunodominat antigens of *Mycobacterium tuberculosis*", Database accession No. PREV199800303509, XP002146135, Abstract & Microbiology vol. 144, No. 5 pp. 1197-1203.

Urquhart et al., "Proteomic contigs' of *Mycobacterium tuberculosis* and *Mycobacterium bovis* (BCG) using Novel immobilized pH gradients", Electrophotesis vol. 18, No. 8, 1997, pp. 1384-1392, XP000938853.

Kumar et al, "Identification of a 25-kilodalton protein of *Mycobacterium bovis* BCG to distinguish BCG strains From *Mycobacterium tuberculosis*", J. of Clinical Microbiology, 1996 34(1):224-226, XP002146161.

Patent Abstracts of Japan vol. 013, No. 589, 1989, JP 01 247094, Ajinomoto co. Inc. JPO&Japio.

Brosch et al, "Use of a *Mycobacterium tuberculosis* H37Rv Bacterial Artificial Chromosome Library for Genome Mapping, Sequencing, and Comparative Genomics", Infection and Immunity, vol. 66, 1998, pp. 2221-2229, American Society for Microbiology, XP002104659.

Jungblut et al, "Comparative proteome analysis of *Mycobacterium tuberculosis* and *Mycobacterium bovis* BCG Strains: Towards functional genomics of microbial pathogens", Molecular Microbiology, vol. 33, No. 6, 1999 pp. 1103-1117, Blackwell Science Ltd., XP000938898.

Cole et al., "Deciphering the biology of *Mycobacterium tuberculosis* from the complete genome sequence," Nature, Jun. 11, 1998, pp. 537-544 (including an additional 10 pp. of Functional Classifications), vol. 393, Macmillian Publishers Ltd.

Cole et al., "Deciphering the biology of *Mycobacterium tuberculosis* from the complete genome sequence," Nature, Nov. 12, 1998, pp. 190-198, vol. 396, Macmillan Publishers Ltd.

Mollenkopf et al., "Application of Mycobacterial Proteomics to Vaccine Design: Improved Protection by *Mycobacterium bovis* BCG Prime-Rv3407 DNA Boost Vaccination against Tuberculosis," *Infection and Immunity*, Nov. 2004, pp. 6471-6479, vol. 72, No. 11, American Society for Microbiology.

*Primary Examiner*—Rodney P. Swartz
(74) *Attorney, Agent, or Firm*—Foley & Lardner LLP

(57) ABSTRACT

The present invention relates to compositions useful in immunization against pathogenic organisms of the genus *Mycobacterium* and for diagnostic purposes. In particular, the present invention relates to a composition comprising at least one protein which is differentially expressed in a virulent strain as compared to an avirulent strain of *Mycobacteria*. Furthermore, the invention relates to compositions comprising fusion proteins, antigenic fragments, nucleic acid molecules encoding the aforementioned proteinaceous compounds and/or antibodies thereto. Additionally, the invention relates to pharmaceutical and diagnostic compositions comprising or employing compounds of the invention. In addition, the present invention relates to the use of the compounds of the invention for the treatment of *Mycobacterium* induced diseases and/or for the preparation of a vaccine for vaccination against *Mycobacterium* induced diseases.

Figure 1A:
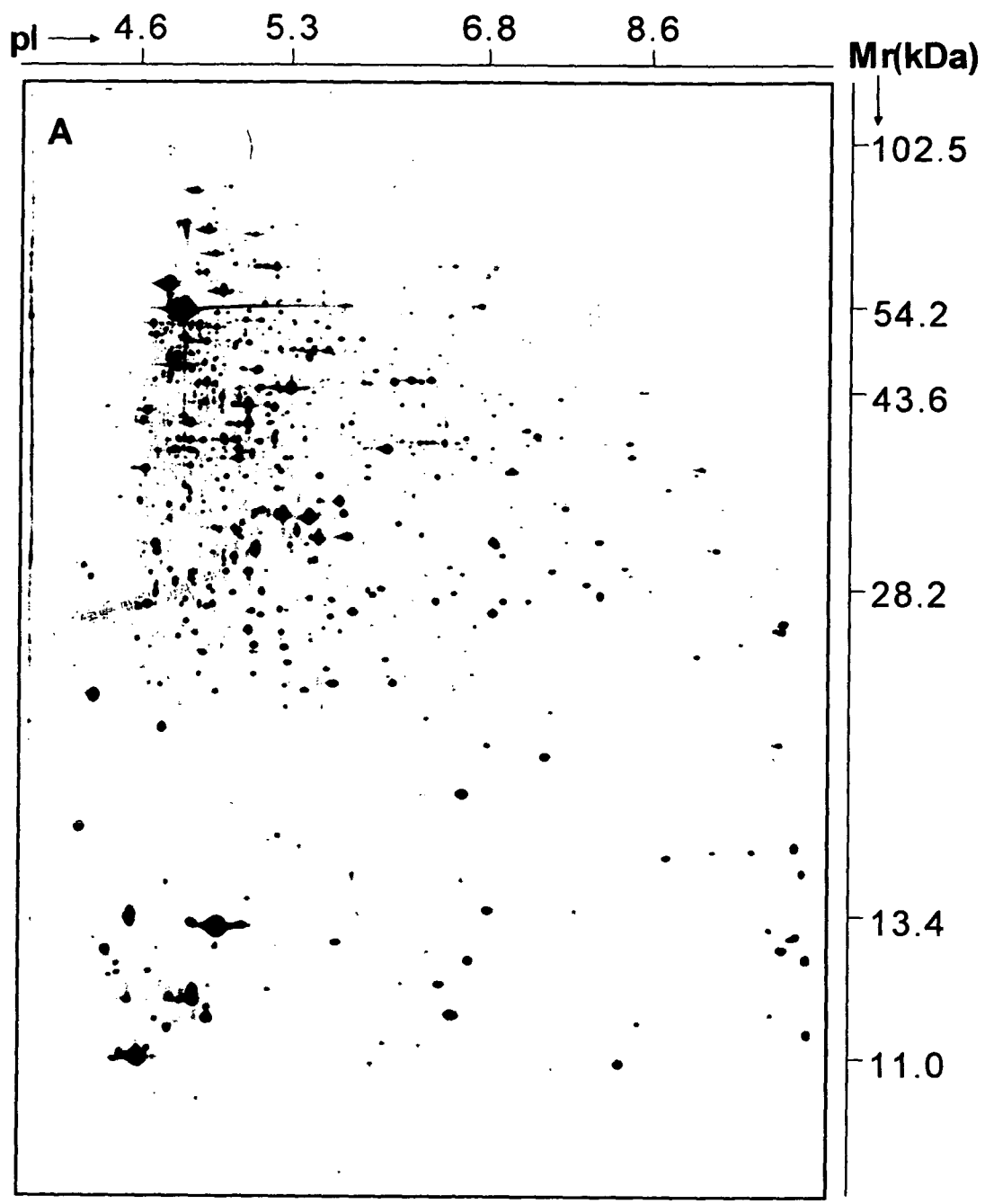

16 Claims, 35 Drawing Sheets a f q r

SEQUENCE LISTING

```
<160> NUMBER OF SEQ ID NOS: 2

<210> SEQ ID NO 1
<211> LENGTH: 303
<212> TYPE: PRT
<213> ORGANISM: M. tuberculosis
<220> FEATURE:
<223> OTHER INFORMATION: PROTEIN CORRESPONDING TO Rv0068

<400> SEQUENCE: 1

Met Thr Lys Trp Thr Ala Ala Asp Ile Pro Asp Gln Thr Gly Arg Thr
1               5                   10                  15

Ala Val Ile Thr Gly Ala Asn Thr Gly Leu Gly Phe Glu Thr Ala Ala
            20                  25                  30

Ala Leu Ala Ala His Gly Ala His Val Val Leu Ala Val Arg Asn Leu
        35                  40                  45

Asp Lys Gly Lys Gln Ala Ala Ala Arg Ile Thr Glu Ala Thr Pro Gly
    50                  55                  60

Ala Glu Val Glu Leu Gln Glu Leu Asp Leu Thr Ser Leu Ala Ser Val
```

```
                65                  70                  75                  80
Arg Ala Ala Ala Ala Gln Leu Lys Ser Asp His Gln Arg Ile Asp Leu
                85                  90                  95

Leu Ile Asn Asn Ala Gly Val Met Tyr Thr Pro Arg Gln Thr Thr Ala
                100                 105                 110

Asp Gly Phe Glu Met Gln Phe Gly Thr Asn His Leu Gly His Phe Ala
                115                 120                 125

Leu Thr Gly Leu Leu Ile Asp Arg Leu Leu Pro Val Ala Gly Ser Arg
                130                 135                 140

Val Val Thr Ile Ser Ser Val Gly His Arg Ile Arg Ala Ala Ile His
145                 150                 155                 160

Phe Asp Asp Leu Gln Trp Glu Arg Arg Tyr Arg Arg Val Ala Ala Tyr
                165                 170                 175

Gly Gln Ala Lys Leu Ala Asn Leu Leu Phe Thr Tyr Glu Leu Gln Arg
                180                 185                 190

Arg Leu Ala Pro Gly Gly Thr Thr Ile Ala Val Ala Ser His Pro Gly
                195                 200                 205

Val Ser Asn Thr Glu Val Val Arg Asn Met Pro Arg Pro Leu Val Ala
                210                 215                 220

Val Ala Ala Ile Leu Ala Pro Leu Met Gln Asp Ala Glu Leu Gly Ala
225                 230                 235                 240

Leu Pro Thr Leu Arg Ala Ala Thr Asp Pro Ala Val Arg Gly Gly Gln
                245                 250                 255

Tyr Phe Gly Pro Asp Gly Phe Gly Glu Ile Arg Gly Tyr Pro Lys Val
                260                 265                 270

Val Ala Ser Ser Ala Gln Ser His Asp Glu Gln Leu Gln Arg Arg Leu
                275                 280                 285

Trp Ala Val Ser Glu Glu Leu Thr Gly Val Val Tyr Pro Val Gly
    290                 295                 300

<210> SEQ ID NO 2
<211> LENGTH: 99
<212> TYPE: PRT
<213> ORGANISM: M. tuberculosis
<220> FEATURE:
<223> OTHER INFORMATION: PROTEIN CORRESPONDING TO Rv3407

<400> SEQUENCE: 2

Met Arg Ala Thr Val Gly Leu Val Glu Ala Ile Gly Ile Arg Glu Leu
1               5                   10                  15

Arg Gln His Ala Ser Arg Tyr Leu Ala Arg Val Glu Ala Gly Glu Glu
                20                  25                  30

Leu Gly Val Thr Asn Lys Gly Arg Leu Val Ala Arg Leu Ile Pro Val
                35                  40                  45

Gln Ala Ala Glu Arg Ser Arg Glu Ala Leu Ile Glu Ser Gly Val Leu
                50                  55                  60

Ile Pro Ala Arg Arg Pro Gln Asn Leu Leu Asp Val Thr Ala Glu Pro
65                  70                  75                  80

Ala Arg Gly Arg Lys Arg Thr Leu Ser Asp Val Leu Asn Glu Met Arg
                85                  90                  95

Asp Glu Gln
```

IDENTIFICATION OF SPECIFIC DIFFERENTIALLY EXPRESSED ANTIGENS

This application is a continuation-of PCT Application No. PCT/EP00/00690, filed Jan. 28, 2000, which claims the benefit of EP99/101590.0, filed Jan. 29, 1999.

SEQUENCE LISTING

The instant application contains a Sequence Listing which has been submitted in both a paper copy and a computer readable copy, and which Sequence Listing is hereby incorporated by reference in its entirety.

The present invention relates to compositions useful in immunization against pathogenic organisms of the genus *Mycobacterium* and for diagnostic purposes. In particular, the present invention relates to a composition comprising at least one protein which is differentially expressed in a virulent strain as compared to an avirulent strain of a pathogenic *Mycobacterium*. Furthermore, the invention relates to compositions comprising fusion proteins, antigenic fragments, nucleic acid molecules encoding the aforementioned proteinaceous compounds and/or antibodies thereto. Additionally, the invention relates to pharmaceutical and diagnostic compositions comprising or employing compounds of the invention. In addition, the present invention relates to the use of the compounds of the invention for the treatment of *Mycobacterium* induced diseases and/or for the preparation of a vaccine for vaccination against *Mycobacterium* induced diseases.

Several documents are cited throughout the text of this specification. Each of the documents cited herein (including any manufacturer's specifications, instructions, etc.) are hereby incorporated by reference; however, there is no admission that any document cited is indeed prior art of the present invention.

Since the beginning of the 1980s, a new trend has been observed in the industrialized countries. On the one hand, resistances to antibiotics have increased, which make it difficult or even impossible to treat many of the disease-causing agents. On the other hand, new infectious diseases, which had been unknown up to now, arise, and old diseases return. For example, malaria and tuberculosis are old epidemics and increasingly surmounting in many different parts of the world. Especially tuberculosis (TB), a chronic infectious disease that is generally caused by infection with *Mycobacterium tuberculosis*, is a disease of major concern. Each year, 8 to 10 million new cases of TB are described, and, causing more than three million deaths per year, TB is a major disease in developing countries as well as an increasing problem in developed areas of the world due to, for example, antibiotic resistance.

Inhibiting the spread of TB will require effective vaccination and accurate, early diagnosis of the disease. Currently, vaccination with live bacteria is the most efficient method for inducing protective immunity. The most common *Mycobacterium* for this purpose is *Bacillus* Calmette-Guerin (BCG), an avirulent strain of *Mycobacterium bovis*.

However, the safety and efficacy of BCG is a source of controversy, and some countries, such as the United States and the Netherlands, do not vaccinate the general public.

Additionally, it has been shown that BCG vaccination affords greater protection against leprosy than against tuberculosis (Ponninghaus, Lancet 339 (1992), 639). Furthermore, *M. bovis* BCG has failed to protect against TB in several trials (WHO, Tech. Rep. Ser. (1980), 651, 1-15) for reasons that are not entirely clear (Fine, Tubercle 65 (1984), 137-153). Additionally, it has been shown that the vaccine strain of *M. bovis* BCG only confers protection against the severe form of miliary tuberculosis in children (Fine, Lancet 346 (1995), 1339-1345). In contrast, its protective capacity against the most common form, pulmonary tuberculosis in adults, is low and highly variable (Colditz (1994), JAMA 271, 698).

Diagnosis of TB is commonly achieved using a skin test, which involves intradermal exposure to tuberculin PPD (protein-purified derivative). Antigen-specific T cell responses result in measurable induration at the injection site by 48-72 hours after injection, which indicates exposure to Mycobacterial antigens. Sensitivity and specificity have, however, been a problem with this test, and individuals vaccinated with BCG cannot be distinguished from infected individuals.

Therefore, it is of major concern that effective and safe vaccines and therapies for the immunization and the treatment of TB as well as useful, reliable diagnostics be developed.

The technical problem of the present invention was thus to provide compositions useful for effective immunization against pathogenic organisms, for effective therapy of infected humans and animals that can be reliably used in low doses and with substantially no side effects and/or for detection/diagnosis of pathogenic organisms in biological/medical samples.

The solution to this technical problem is achieved by providing the embodiments characterized in the claims.

Accordingly, the present invention relates to a composition comprising at least one protein which is differentially expressed in a virulent strain as compared to an avirulent strain of the genus *Mycobacterium*.

The term "composition", as used in accordance with the present invention, comprises at least one protein, an antigenic fragment of said protein, a fusion protein, a nucleic acid molecule and/or an antibody of this invention and, optionally, further molecules, either alone or in combination, like e.g. molecules which are capable of optimizing antigen processing, cytokines, immunoglobulins, lymphokines or CpG-containing DNA stretches or, optionally, adjuvants. The composition may be in solid, liquid or gaseous form and may be, inter alia, in form of (a) powder(s), (a) tablet(s), (a) solution(s) or (an) aerosol(s). In a preferred embodiment, said composition comprises at least two, preferably three, more preferably four, most preferably five differentially expressed proteins.

The term "protein" means, in accordance with the present invention, a peptide(s) or (a) (poly)peptide(s) which encompass amino acid chains of any length, wherein the amino acid residues are linked by covalent peptide bonds. However, peptidomimetics of such proteins wherein amino acid(s) and/or peptide bond(s) have been replaced by functional analogs are also encompassed by the invention. In accordance with this invention, a protein may comprise different protein species. A protein species is defined by its chemical composition and modifications of said peptide(s)/(poly)peptide(s) by, inter alia, glycosylations, acetylations, phosphorylations, lipidations or by amino acid exchanges, the term describes a chemically clearly-defined molecule and corresponds, inter alia, to one spot on a high-performace 2-DE pattern (Jungblut, Electorphoresis 17 (1996), 839-847). The term protein species is therefore defined as the smallest unit of a protein classification, defined by its chemical structure.

The term "differentially expressed" denotes in the context of the present invention proteins/protein species which are distinctly expressed, regulated and/or modified. Therefore, the term "differentially expressed" includes protein(s)/protein species that are absent in, that occur in different amounts in and/or that comprise different post-translating modifications in a "virulent" strain compared to an "avirulent" strain of a pathogenic organism. The term "differentially expressed" as used in accordance with the invention denotes therefore not only proteins/protein species which are missing in one strain as compared to another (+/− variants), but also comprises mobility variants and/or intensity variants. Intensity variants are protein species occurring in comperative protein 2DE-patterns which differ in amount. A +/− variant can be considered as an extreme intensity variant, where the protein species occurs in one pattern and is absent in the other. If the protein occurs in two different compared patterns at different positions, these two positions can be considered as indication for two different protein species of this protein (inter alia, due to secondary modifications as explained herein above) which are defined as mobility variants. These variants (+/−, intensity or mobility) can be detected by proteome analysis.

Previously, the determination of immunogenic antigenic and/or pathogenic determinants of pathogenic organisms had been hampered by the fact that it was not possible to analyze the whole proteome of such organisms, like *Mycobacteria*, by conventional means. However, the previously employed analysis of cellular fractions and/or fragments (like bacterial membranes) can only reflect a limited number of differentially expressed protein(s)/protein species, if any, due to the loss of proteinaceous material during fractionation and isolation of such fragments. In accordance with the present invention, a new method (as examplified in the examples) has been employed that allows the analysis of whole pathogenic organisms and it was surprisingly found, that a great number of differentially expressed proteins in a virulent strain as compared to an avirulent strain of *Mycobacteria* can be identified.

Differentially expressed proteins (protein species) may be identified, detected and/or brought into a biological correlation, inter alia, by proteome analysis of whole organisms (like mycobacteria) or, less preferred, of biochemically defined fractions (like, inter alia, lipoproteins, glycoproteins, phosphoproteins) or of biologically defined fractions (like, inter alia, membranes, cytosol, structural elements of a pathogenic organism); see, e.g. Wilkins (1997), "Proteome Research: New Frontiers in Functional Genomics, Springer-Publishers Berlin; Kahn, Science 270 (1995), 369-370; Jungblut, J. Biotech. 41 (1995), 111-120; Blüggel, Biospektrum 5 (1998), 39-44; Lohaus, Biospekturm 5 (1998), 32-39; Jungblut Electrophoresis 17 (1996), 839-847; Scheler, Electrophoresis 19 (1998), 918-927.

As known to the person skilled in the art, analysis of proteomes of lower complexity, e.g. ribosomes with 60 protein species, can be performed, inter alia, by protein/protein species separation and identification strategies, comprising, for example, 2-dimensional gel electrophoresis (2-DE; Kaltschmidt, Anal. Biochem. 36 (1970), 401) or HPLC (Kamp, J. Chromatogr. 317 (1984), 181). However, analysis of proteomes of higher complexity can be carried out, inter alia, by a combination of isoelectric focusing and SDS-PAGE (Vesterburg, Acta Chem. Scand. 20 (1966), 820; Laemmli, Nature 227 (1970), 680) and the use of large-sized gels (Jungblut, Electrophoresis 15 (1994), 685; Klose, Electrophoresis 16 (1995), 1034). Comparison of individual, specific 2-DE gels allows for the identification of differentially expressed proteins and the identification of proteins separated by 2-DE is known to the skilled artisan (see, e.g. Patterson, Electrophoresis 16 (1995), 1791; Jungblut, Electrophoresis 17 (1996), 839; Jungblut, Mass Spectrometry Reviews 16 (1997), 145; Kaufmann, Jahrbuch der MPG (1998), 42-57; Blüggel (1998), loc. cit., Schaible, DGHM-Kongress (1998), Einhoon-Resse Verlag (ISSN 1433-3988), 20).

In order to further identify differentially expressed proteins, several techniques which are known in the art can be used. These techniques comprise, but are not limited to, in-gel digestions, electroelution procedures, microsequencing, amino acid analysis, Edman-sequencing or mass spectroscopy. For example, some techniques start directly from gel(s), others need a transfer to membranes by blotting. To the first group belong, inter alia, coelectrophoresis, internet comparison of position, peptide mapping by SDS-PAGE (Cleveland, J. Biol. Chem. 252 (1977), 1102), protein elution and MALDI-MS or N-terminal sequencing by Edman degradation (Edman, Acta Chem. Scand. 4 (1950), 283), enzymatic in-gel digestion, analysis of peptides directly in the mixture by mass spectrometry, peptide mass fingerprinting (Pappin, Curr. Biol. 3, (1993), 327), PSD-MALDI-MS (Spengler, Rapid Commun. Mass Spectrom. 6, (1992), 105), ESI-MS (electrospray-ionization-MS) and/or (after separation) by micro-HPLC. HPLC separated peptides may be further analysed, inter alia, by Edman degradation, PSD-MALDI-MS, MS/MS (Wilm, Nature 379, (1996), 466) or ladder sequencing (Thiede, FEBS Lett. 357, (1995), 65) in order to obtain a peptide sequence. Proteins immobilized on membranes allow the identification by immunostaining (Towbin, Proc. Natl. Acad. Sci. USA 76, (1979), 4350), N-terminal sequencing (either directly or after deblocking) (Hirano, Electrophoresis 14, (1993), 839), determination of the protein mass (Eckerskorn, Electrophoresis 13, (1992), 664), amino acid analysis (Jungblut, J. Prot. Chem. 11, (1992), 603) and/or enzymatic digestion with the same proteinchemical techniques as described for in-gel digestions. Results of such analysis are mass fingerprints.

The resulting peptide masses are searched by search programs (e.g. prospector.ucsf.edu/ucsfhtm13.2/msfit.htm; www.expasy.ch/tools/peptident.html) in sequence databases (EMBL, PIR, NCBI, MIPS, Swiss-Prot, OWL). By use of such mass fingerprints amino acid sequences can be deduced and sequenced. From these sequenced amino acid fragments degenerative oligonucleotides may be deduced and synthesized that may be used to screen, for example, genomic or cDNA libraries to identify and clone the corresponding GENE/cDNA.

Identified proteins may be produced by, for example, recombinant techniques or by biochemical or synthetic techniques which are known to the skilled artisan (Sambrook et al., "Molecular Cloning, A Laboratory Manual", Cold Spring Harbor Laboratory, N.Y. (1989); Ausubel, "Current Protocols in Molecular Biology", Green Publishing Associates and Wiley Interscience, N.Y. (1989)).

Other methods for the elucidation of differentially expressed proteins include, but are not limited to, enzyme activity, receptor activity measurements, immunostainings, immunohistochemical methods.

As shown in the appended examples, differential protein expression can be detected by preparation of microorganisms or, less preferred, compartment/fragments thereof, 2-DE, subtractive analysis and identification of proteins by peptide mass fingerprinting (PMF) with or without confirmation by further methods.

Identification of protein species from 2-DE patterns by only one of the above-described methods, peptide mass fingerprinting or amino acid analysis, was described to lead to false identification (Cordwell, Electrophoresis 16 (1995), 438; Mortz, Biol. Mass. Spec. 23 (1993), 249). However, the present invention, surprisingly showed that differentially expressed proteins may be identified by peptide mass fingerprinting without confirmation by a further method. As examplified in the appended examples, improvements in the sample preparation, e.g. reduction of volumes and surface contacts, use of volatile buffers and improvements in mass spectrometry, introduction of delayed extraction, results in improved mass accuracy, resolution, and sensitivity, leading to high sequence coverage of at least 30%. This sequence coverage is sufficient for identification and needs no further confirmation. Thus, the present invention also concerns a method for identification of differentially expressed proteins as discussed above and illustrated in examples 2, 4 and 8.

The term "virulent strain", in accordance with the present invention, denotes the capacity of a pathogenic strain of the genus Mycobacterium to infect a host and/or to cause disease—defined broadly in terms of severity of symptoms in a host. Thus, a "virulent strain" might cause symptoms in a susceptible host, whereas another host might be unaffected by this strain, which can be therefore considered as being an "avirulent strain" in this second host. As used in accordance with the present invention, the term "avirulent strain" denotes strains of a Mycobacteria which is not capable of inducing infection and/or causing disease in a specific host or in a host species. The term "avirulent strains" denotes furthermore attenuated strains of microorganisms.

The terms "virulent" and "avirulent" strains not only relate to laboratory strains but also comprise wildtype strains. The virulency of a strain is known in the art and described, inter alia, in Brandis et al., "Lehrbuch der medizinischen Mikrobiologie", Gustav Fischer Verlag, 7. Auflage (1994), Zinsser Microbiology, ed Joklik, Willett, Amos, Wilten 20$^{th}$ edition, Appleton & Lange, 1992.

In a preferred embodiment of the composition of the present invention said strains are selected from the group consisting of M. tuberculosis, M. bovis, M. avium, M. africanum, M. kanasasii, M. intracellulare, M. ulcerans, M. paratuberculosis, M. simiae, M. scrofulaceam, M. szulgai, M. xenopi, M. fortuitum, M. chelonei M. leprae and M. marinum.

In a more preferred embodiment of the composition of the present invention said protein is differentially expressed in M. tuberculosis and in M. bovis.

In a particularly preferred embodiment the present invention relates to a composition wherein said virulent strain is M. tuberculosis H37Rv or M. tuberculosis Erdman and said avirulent strain is M. bovis BCG. Furthermore, the present invention relates to a composition wherein said protein is differentially expressed in M. tuberculosis H37Rv and M. tuberculosis Erdman as compared to M. bovis BCG.

In an even more preferred embodiment of the composition of the present invention said differentially expressed protein is 2-isopropyl malate synthase (Rv3710), s-adenosylmethionine synthase (metK, RV1392), succinyl-CoA synthase a-chain (sucD, RV0952), oxidoreductase of aldo/keto reductase family (Rv2971), oxidoreductase (Rv0068), elongation factor G (FusA2, Rv0120c), uridylate kinase (PyrH, Rv2883c), ABC-type transporter (Rv1463), short chain dehydrogenase/reductase family (RV1856C), hydrolase (LinB, Rv2579), phosphoribosylamino-imidazole carboxylase catalytic subunit (PurE, Rv3275c), hypothetical protein (Rv2557), hypothetical protein (Rv3407), hypothetical protein (Rv3881c), hypothetical protein (Rv2449c), hypothetical protein (Rv0036c), hypothetical protein (Rv2005c) or transcriptional regulator (Crp/Fr family) (Rv 3676). As shown in the appended examples, whereas 2-isopropyl malate synthase (Rv3710) is expressed in M. tuberculosis H37Rv, it is not detected and identified in M. bovis BCG. Furthermore, s-adenosylmethionine synthase (metK, RV1392), succinyl-CoA synthase a-chain (SUCD, Rv0952), oxidoreductase of aldo/keto reductase family (Rv2971) or oxidoreductase (Rv0068), represent protein species which are differentially expressed in M. tuberculosis H37Rv and M. bovis BCG and represent mobility variants. As intensity variants may be considered proteins corresponding to the Rv numbers Rv0652, Rv2429, Rv2428, RV0569, Rv0475, Rv3463, Rv3054c. As +/−-variants may be considered Rv2883c, Rv0120c, Rv1463, Rv2579, Rv3275c, Rv3407, Rv3881c, Rv2449c, Rv0036c, Rv2005c or Rv3676. As shown in the appended examples, whereas elongation factor G (Rv0120c), uridylate kinase (Rv2883c), ABC-type transporter (Rv1463), short chain dehydrogenase/reductase family protein (Rv 1856c), 1,3,4,6-tetracholoro-1,4,-cyclohexadiene hydrolase (Rv2579), phosphoribosylaminoimidazole carboxylase catalytic subunit (Rv3275c), hypothetical protein (Rv2557), and hypothetical protein (Rv3407) are expressed in M. tuberculosis H37Rv and M. tuberculosis Erdman, they are not detected in M. bovis BCG Chicago and M. bovis BCG Copenhagen. Furthermore, protein spot A607 in M. tuberculosis H37Rv and the corresponding spot A148 in M. tuberculosis Erdman have no counterparts in M. bovis BCG Chicago and M. bovis BCG Copenhagen. This protein was identified herein as the hypothetical protein Rv3881c. Furthermore, spots C434 from M. tuberculosis H37Rv and the corresponding spot C508 from M. tuberculosis Erdman have no counterparts in M. bovis BCG Chicago and M. bovis Copenhagen. They were identified as a hypothetical protein (Rv2005c). Rv2005c occurs at the 2-DE pattern in another form at a different position in all four strains. Additionally, the spots B69, C176, D12 and D115 of M. tuberculosis H37Rv with their counterparts in M. tuberculosis Erdman, B54, C404, D115 and D130, respectively, have no counterparts in M. bovis BCG Chicago and M. bovis BCG Copenhagen. B69 was identified as a hypothetical protein (Rv2449c). C176 was identified as a hypothetical protein (Rv0036c). D12 and D115 of M. tuberculosis H37Rv were identified as transcriptional regulator (Crp/Fnr family) (Rv3676). As will be described herein below these proteins/protein species might serve, inter alia, in pharmaceutical and diagnostic compositions. Cole (Nature 393 (1998), 537) published the complete sequence of the M. tuberculosis H37Rv genome and identified a total of 3924 individual genes which were classified according to the classification of Riley (Microbiol. Rev. 57 (1993), 862). Identifications of this putative genes were performed by homology searches of deduced open reading frames from other microorganisms. Therefore, the term "Rv numbers" as employed herein corresponds to clearly defined nucleic acid sequences (deduced open reading frames) as describes in Cole et al., (loc. cit.). However, for most of the identified putative genes of M. tuberculosis, it is not clearly shown that they are actually expressed additional sequence information on mycobacterial genes is also available from the Sanger Centre, U. K. Under www.sanger.ac.uk/Projects/M_tuberculosis/ information on the genomic sequence of M. tuberculosis is available. Therefore, the "Rv-numbers" not only refer to nucleic acid sequences but also to protein sequences as deposited in the Sanger database. Further information on M. tuberculosis sequence is available from the Institut Pasteur, Paris under bioweb.pasteur.fr/GenoList/TubercuList/.

The invention also relates to a composition comprising an antigenic fragment of the protein as defined herein.

The term "antigenic fragment", as used herein, refers to the ability of said fragment to elicit an immune response (e.g. humoral or cellular) in a subject, such as a human, and/or in a biological sample. These fragments may consist entirely of the antigenic and/or immunogenic portion of the protein or may contain additional sequences. The additional sequences may be derived from said protein or may be heterologous, and such additional sequences may (but need not) be antigenic and/or immunogenic. The antigenicity of an amino acid sequence can be deduced/predicted by methods known to the person skilled in the art as for example described in Parker, J. Immunol. 152 (1994), 163 (bimas.dcrt.nih.gov:80/molbio/hla_bind/), Meister, Vaccine 13 (1995), 581-591 or Bull, Biochem. Biophys. 161 (1974), 665-670. Furthermore, computer predictions may be employed to elucidate hydrophilicity and/or antigenicity of amino acid sequences and stretches. Such computer programs may be Garnier analysis of the on the plot v. 2.5e package, the GCG-software derived from HGMP resource Center Cambridge (Rice (1995) Programme Manual for the EGCG package, Cambridge (B10 IKQ, England) or the programme based on Kyte/Dolittle, J. Mol. Biol. 157 (1982), 105-132 (see also www.expasy.ch/cgi-bin/protscale.pl).

Antigenic fragment may be produced recombinantly using a polynucleotide sequence that encodes the antigenic fragment or may be produced by biochemical or synthetic techniques. Those methods are known to those of ordinary skill in the art (see, e.g. Sambrook et al., loc. cit.; Harlow and Lane "Antibodies, A Laboratory Manual", CSH Press, Cold Spring Harbor, N.Y. (1988); Merrifield, J. Am. Chem. Soc. 85 (1963), 2149-2146; Stewart, "Solid Phase Peptide Synthesis", WH Freeman Co, San Francisco (1969); Scopes, "Protein Purification", Springer Verlag, New York, Heidelberg, Berlin (1987); Janson, "Protein Purification, Principles, High Resolution Methods and Applications", VCH Publishers, New York, Weinheim, Cambridge (1989); Wrede, "Concepts in Protein Engineering and Design", Walter de Gruyter, Berlin, N.Y. (1994); Wittmann-Liebold, Jungblut "Analysis and Characterization of Proteins", 47-107).

Additionally, the invention relates to a fusion protein comprising a protein and/or an antigenic fragment as defined in the above.

The protein and/or the antigenic fragment of the present invention can comprise a further domain, said domain being linked by covalent or non-covalent bonds. The linkage can be based on genetic fusion according to the methods known in the art (Sambrook et al., loc. cit.; Ausubel, loc. cit.) or can be performed by, e.g., chemical cross-linking as described in, e.g., WO 94/04686. The additional domain present in the fusion protein comprising the protein of the invention may be joined directly (i.e. with no intervening amino acids) or may be linked by a flexible linker, advantageously a polypeptide linker, wherein said polypeptide linker comprises plural, hydrophilic, peptide-bonded amino acids of a length sufficient to span the distance between the C-terminal end of said further domain and the N-terminal end of the protein or vice versa. The above described fusion protein may further comprise a cleavable linker or cleavage site, which, for example, is specifically recognized and cleaved by proteinases or chemical agents. Cleavable linker sequences include, but are not limited to, Factor XA or enterokinase (Invitrogen, San Diego, Calif., USA).

Additionally, said further domain may be of a predefined specificity or function. In this context, it is understood that the protein of the invention may be further modified by conventional methods known in the art. This allows for the construction of fusion proteins comprising the protein of the invention and other functional amino acid sequences, e.g., immunologically relevant proteins like cytokines, lymphocytes, interferones, or protein tags (GST, GFP, h-myc peptide, FLAG, HA peptide) which may be derived from heterologous proteins.

In yet another preferred embodiment the present invention relates to a composition comprising at least one differentially expressed protein as defined herein above wherein said differentially expressed protein is biochemically, biophysically and/or recombinantly modified. Such modifications may comprise amino acid substitutions, deletions, insertions, additions and/or duplications wherein said modified differentially expressed protein should still comprise at least one antigenic fragment or epitope which is specifically recognized by an antibody directed to, raised to and/or engineered to detect the non-modified differentially expressed protein as defined herein above. The non-modified amino acid sequence of a differentially expressed protein is deducible for the person skilled in the art as described herein above, inter alia, by employing biochemical and recombinant methods and sequence databases. Additionally, the non-modified amino acid sequence of a differentially expressed protein as defined herein above may be deduced from nucleic acid sequences and/or proposed open reading frames as known to the person skilled in the art. For example, the complete genome sequence of *M. tuberculosis* H37Rv is published in Cole et al. (1998, loc. cit.).

In addition, the invention relates to a fusion protein comprising at least two proteins as defined herein and/or (an) antigenic fragment(s) as defined herein.

In a further embodiment the fusion protein of the present invention comprises an immunostimulatory molecule.

The term "immunostimulatory molecule" denotes in accordance with the present invention molecules or fragments thereof which, inter alia, activate and/or stimulate the humoral and cellular response of an immune system. They might, e.g. activate antigen-presenting cells, stimulate natural killer cells, enhance the production of antibodies directed against an antigen and/or a pathogen or induce the proliferation of cells of the immune system. These molecules are known in the art and comprise, inter alia, cytokines, lymphokines, immunoglobulins, interleukins and/or complement factors (see, e.g. Paul, "Fundamental Immunology", Raven Press (1989); Schaible, Adv. In Immunology 71 (1999), 261-377).

In one further preferred embodiment of the fusion protein of the present invention said fusion protein comprises a molecule capable of optimizing antigen processing.

Cellular immune recognition is mediated by a special class of lymphoid cells, T-cells. These cells do not recognize whole antigens but instead they respond to degraded peptide fragments thereof which appear on the surface of the target cell bound to proteins called major histocompatibility complex (MHC) molecules (antigen processing). Essentially all nucleated cells have MHC class I molecules, whereas MHC II are restricted to immune cells with special presenting qualities. Molecules which are capable of optimizing antigen processing are known in the art and comprise, inter alia, listeriolysin, which improves MHC class I restricted immune responses (see, e.g., Hess, PNAS 95 (1998), 5299-5304).

The term "fusion protein" as employed hereinabove also relates to chimeric proteins wherein said chimeric protein comprises at least one differentially expressed protein and/or (a), preferably antigenic, fragment(s) thereof in combination with at least one other protein, peptide or fragment(s) thereof. Furthermore, said chimeric protein may comprise at least two modified differentially expressed proteins as defined herein above.

The invention also relates to a composition comprising at least one fusion protein as defined hereinabove.

The invention further relates to a nucleic acid molecule coding for a modified differentially expressed protein as defined herein, the antigenic fragment as defined herein and/or a fusion protein as defined herein.

The nucleic acid molecule of the invention or employed in methods or compositions of the invention may be DNA such as cDNA or RNA such as mRNA. Additionally, the nucleic acid molecule of the invention may be PNA. Its origin may be natural, synthetic or semisynthetic or it may be a derivative, such as said peptide nucleic acid (Nielsen, Science 254 (1991), 1497-1500). Furthermore, said nucleic acid molecule may be a recombinantly produced chimeric nucleic acid molecule comprising any of the aforementioned nucleic acid molecules either alone or in combination. Preferably, said nucleic acid molecule is part of a vector.

Such vectors may be, e.g., a plasmid, cosmid, virus, bacteriophage or another vector used e.g. conventionally in genetic engineering, and may comprise further genes such as marker genes which allow for the selection of said vector in a suitable host cell and under suitable conditions.

Furthermore, the vectors may, in addition to the nucleic acid sequences of the invention, comprise expression control elements, allowing proper expression of the coding regions in suitable hosts. Such control elements are known to the artisan and may include a promoter, translation initiation codon, translation and insertion site for introducing an insert into the vector. Preferably, the nucleic acid molecule of the invention is operatively linked to said expression control sequences allowing expression in eukaryotic or prokaryotic cells.

Control elements ensuring expression in eukaryotic and prokaryotic cells are well known to those skilled in the art. As mentioned above, they usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions. Possible regulatory elements permitting expression in for example mammalian host cells comprise the CMV-HSV thymiakine kinase promoter, SV40, RSV-promoter (Rous sarcome virus), human elongaticn factor 1α-promoter, CMV enhancer or SV40-enhancer. For the expression in prokaryotic cells, a multitude of promoters including, for example, the tac-lac-promoter or the trp promoter, has been described. Beside elements which are responsible for the initiation of transcription such regulatory elements may also comprise transcription termination signals, such as SV40-poly-A site or the tk-poly-A site, downstream of the polynucleotide. In this context, suitable expression vectors are known in the art such as Okayama-Berg cDNA expression vector pcDV1 (Pharmacia), pRc/CMV, pcDNA1, pcDNA3 (In-vitrogene), pSPORTI (GIBCO BRL), or prokaryotic expression vectors, such as lambda gt11. Beside the nucleic acid molecules of the present invention, the vector may further comprise nucleic acid sequences encoding for secretion signals. Such sequences are well known to the person skilled in the art. Furthermore, depending on the expression system used leader sequences capable of directing the protein/(poly) peptide to a cellular compartment may be added to the coding sequence of the nucleic acid molecules of the invention and are well known in the art. The leader sequence(s) is (are) assembled in appropriate phase with translation, initiation and termination sequences, and preferably, a leader sequence capable of directing secretion of translated protein, or a protein thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. Once the vector has been incorporated into the appropriate host, the host is maintained under conditions suitable for high level expression of the nucleotide sequences, and, as desired, the collection and purification of the proteins, antigenic fragments or fusion proteins of the invention may follow. Of course, the vector can also comprise regulatory regions from pathogenic organisms.

Furthermore, said vector may also be a gene transfer or targeting vector. Gene therapy, which is based on introducing therapeutic genes (for example for vaccination) into cells by ex-vivo or in-vivo techniques is one of the most important applications of gene transfer. Suitable vectors, vector systems and methods for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Wang, Nature Medicine 2 (1996), 714-716; WO 94/29469; WO 97/00957, Schaper, Current Opinion in Biotechnology 7 (1996), 635-640 or Verma, Nature 389 (1997), 239-242 and references cited therein. The nucleic acid molecules of the invention and vectors as described herein above may be designed for direct introduction or for introduction via liposomes, or viral vectors (e.g. adenoviral, retroviral) into the cell. Additionally, a baculoviral system can be used as eukaryotic expression system for the nucleic acid molecules of the invention. In addition to recombinant production, fragments of the protein, the fusion protein or antigenic fragments of the invention may be produced by direct peptide synthesis using solid-phase techniques (cf Stewart et al. (1969) Solid Phase Peptide Synthesis, WH Freeman Co, San Francisco; Merrifield, J. Am. Chem. Soc. 85 (1963), 2149-2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments may be chemically synthesized separately and combined using chemical methods to produce the full length molecule.

The invention in addition relates to a composition comprising at least one nucleic acid molecule as defined herein and/or at least one nucleic acid molecule coding for any of the differentially expressed proteins as defined herein. Said nucleic acid molecule coding for a differentially expressed protein, codes preferably for Rv3710, Rv1392, Rv0952, Rv2971, Rv0068, Rv0120c, Rv2883c, Rv1463, Rv1856c, Rv2579, Rv3275c, Rv2557, Rv3407, Rv3881c, Rv2449c, Rv0036c, Rv2005c or Rv3676.

Most preferably said nucleic acid molecule is the nucleic acid molecule as disclosed under said Rv-number under www.sanger.ac.uk/Projects/M_tuberculosis or bioweb.pasteur.fr/GenoList/TubercuList. However, the present invention relates also to compositions comprising at least one Nucliec acid molecule which hybridizes under stringent conditions to the complementary strand of the nucleic acid molecule of any of the above cited Rv-numbers. "Stringent conditions" are preferably conditions as described in Sambrook (Molecular Cloning, A Laboratory Manual, 2nd edition (1989), Cold Spring Harbor Laboratory Press, Cold Spring Harbor, N.Y.).

Such hybridizing sequences show preferably an identity of at least 50%, more preferably of at least 70% and most preferably of at least 90% on the nucleic acid level to the sequences described above. The molecules hybridizing to the nucleic acid molecules as disclosed under the above cited Rv-numbers or to the nucleic acid molecules of the invention thus also comprise fragments, derivatives and allelic variants of the above-described nucleic acid molecules which encode a differentially expressed protein (or a fragment thereof) as described in the present invention. In this regard, fragments are defined as parts of the nucleic acid molecules, which are long enough in order to encode the at least one epitope/ antigenic fragment which is specifically recognized by an antibody directed to, raised to and/or engineered to detect a differentially expressed protein as defined herein. The term derivatives means that the sequences of these hybridizing molecules differ from the sequences of the above-mentioned nucleic acid molecules at one or more positions and that they exhibit a high degree of homology to these sequences. Hereby, homology means a sequence identity of at least 50%, in particular an identity of at least 60%, preferably of more than 70% and still more preferably a sequence identity of more than 90%. The deviations occurring when comparing with the above-described nucleic acid molecules might have been caused by deletion, substitution, insertion or recombination.

Said composition is useful, inter alia, for medical and diagnostic purposes, in particular, for pharmaceutic and vaccination purposes.

Moreover, the invention relates to an antibody or a fragment or a derivative thereof directed against the protein as defined herein, the antigenic fragment of the invention, the nucleic acid molecule of the invention or the fusion protein as defined herein. Such antibodies may include, but are not limited to, polyclonal, monoclonal, chimeric or single chain antibodies or fragments or derivatives of such antibodies.

The general methodology for producing antibodies is well-known and has been described in, for example, Köhler and Milstein, Nature 256 (1975), 494 and reviewed in J. G. R. Hurrel, ed., "Monoclonal Hybridoma Antibodies: Techniques and Applications", CRC Press Inc., Boco Raron, Fla. (1982), as well as that taught by L. T. Mimms et al., Virology 176 (1990), 604-619. As stated above, in accordance with the present invention the term "antibody" relates to monoclonal or polyclonal antibodies. Antibody fragments or derivatives comprise F(ab')$_2$, Fab, Fv or scFv fragments; see, for example, Har'ow and Lane, "Antibodies, A Laboratory Manual", CSH Press 1988, Cold Spring Harbor, N.Y. Preferably the antibody of the invention is a monoclonal antibody. Furthermore, in accordance with the present invention, the derivatives can be produced by peptidomimetics. Such production methods are well known in the art and can be applied by the person skilled in the art without further ado.

Furthermore, the invention relates to a composition comprising at least one antibody, a fragment or a derivative thereof as defined above. Such antibodies, fragments or derivatives can be used for diagnostic or for pharmaceutical purposes, i.e. for the treatment of *Mycobacteria*-induced diseases or the vaccination against these pathogens.

The invention also relates to a composition as defined above which is a pharmaceutical composition further comprising, optionally, a pharmaceutically acceptable carrier.

The pharmaceutical composition may comprise the proteins of the present invention, the fusion proteins of the present invention, antigenic fragments of the invention and/or antibodies (or their fragments or derivatives) of the invention, either alone or in combination. The pharmaceutical composition of the present invention may be used for effective therapy of infected humans and animals and/or for vaccination purposes.

The pharmaceutical composition of the present invention may further comprise a pharmaceutically acceptable carrier, excipient and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg per dose; however, doses below or above this exemplary range are envisioned, especially considering the aforementioned factors. Administration of the suitable compositions may be effected by different ways, e.g., by intravenous, intraperitoneal, subcutaneous, intramuscular, topical or intradermal administration. If the regimen is a continuous infusion, it should also be in the range of 1 μg to 10 mg units per kilogram of body weight per minute, respectively. Progress can be monitored by periodic assessment. The compositions of the invention may be administered locally or systemically. Administration will generally be parenterally, e.g., intravenously. The compositions of the invention may also be administered directly to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents such as interleukins, interferons and/or CpG-containing DNA stretches, depending on the intended use of the pharmaceutical composition.

In a preferred embodiment of the present invention the pharmaceutical composition as defined herein is a vaccine.

Vaccines may be prepared, inter alia, from one or more proteins, derivatives of the proteins, nucleic acid molecules, fusion proteins, antigenic fragments or antibodies, fragments of said antibodies or derivatives of the antibodies of the invention.

For example, nucleic acid molecules of the invention may be used for gene vaccination or as DNA vaccines. Routes for administration of gene/DNA vaccines are well known in the art and DNA vaccination has been successfully used to elicit alloimmune, anti-tumor and antiidiotype immune responses (Tighe M. et al., Immunology Today 19 (1998), 89-97). Moreover, inoculation with nucleic acid molecules/DNA has been found to be protective in different modes of disease (Fynan, Proc. Natl. Acad. Sci. U.S.A. 90 (1993), 11478-11482; Boyer, Nat. Med. 3 (1997), 526-532; Webster, Vaccine 12 (1994), 1495-1498; Montgomery et al., DNA Cell Biol. 12 (1993), 777-783; Barry, Nature 311 (1995), 632-635; Xu and Liew, Immunology 84 (1995), 173-176; Zhoug, Eur. J. Immunol. 26 (1996), 2749-2757; Luke, J. Inf. Dis. 175 (1997), 91-97; Mor, Biochem. Pharmacology 55 (1998), 1151-1153; Donelly, Annu. Rev. Immun. 15 (1997), 617-648; MacGregor, J. Infect. Dis. 178 (1998), 92-100).

The proteins, nucleic acid molecules, fusion proteins, antigenic fragments or antibodies, fragments or derivatives of said antibodies of the invention used in a pharmaceutical composition as a vaccine may be formulated e.g. as neutral or salt forms. Pharmaceutically acceptable salts, such as acid addition salts, and others, are known in the art. Vaccines can be, inter alia, used for the treatment and/or the prevention of an infection with pathogens and are administered in dosages compatible with the method of formulation, and in such amounts that will be pharmacologically effective for prophylactic or therapeutic treatments.

Proteins, protein fragments and/or protein derivatives used as vaccines are well known in the art (see, e.g. Cryz, "Immunotherapy and Vaccines", VCH Weinheim (1991); Paul (1989), loc. cit.). Furthermore, it has been shown that even intracellular enzymes of bacterial pathogens can act as antigenic entities which provide immunological protection (Michetti, Gastroenterology 107 (1994), 1002; Radcliff, Infect. Immun. 65 (1997), 4668; Lowrie, Springer Semin. Immunopathol. 19 (1997), 161)

A vaccination protocol can comprise active or passive immunization, whereby active immunization entails the administration of an antigen or antigens (like the compositions of the present invention or proteins, nucleic acid molecules, fusion proteins, antigenic fragments or antibodies, fragments of said antibodies or derivatives of the antibodies of the present invention) to the host/patient in an attempt to elicit a protective immune response. Passive immunization entails the transfer of preformed immunoglobulins or derivatives or fragments thereof (e.g., the antibodies, the derivatives or fragments thereof of the present invention) to a host/patient. Principles and practice of vaccination and vaccines are known to the skilled artisan, see, for example, in Paul, "Fundamental Immunology" Raven Press, New York (1989) or Morein, "Concepts in Vaccine Development", ed: S. H. E. Kaufmann, Walter de Gruyter, Berlin, N.Y. (1996), 243-264. Typically, vaccines are prepared as injectables, either as liquid solutions or suspensions; solid forms suitable for solution in or suspension in liquid prior to injection also may be prepared. The preparation may be emulsified or the protein may be encapsulated in liposomes. The active immunogenic ingredients often are mixed with pharmacologically acceptable excipients which are compatible with the active ingredient. Suitable excipients include but are not limited to water, saline, dextrose, glycerol, ethanol and the like; combinations of these excipients in various amounts also may be used. The vaccine also may contain small amounts of auxiliary substances such as wetting or emulsifying reagents, pH buffering agents, and/or adjuvants which enhance the effectiveness of the vaccine. For example, such adjuvants can include aluminum compositions, like aluminumhydroxide, aluminumphosphate or aluminumphospho-hydroxide (as used in "Gen H-B-Vax®" or "DPT-Impfstoff Behring"), N-acetyl-muramyl-L-th reonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphaosphoryloxy)-ethylamine (CGP 19835A, also referred to as MTP-PE), MF59 and RIBI (MPL+TDM+CWS) in a 2% squalene/Tween-80® emulsion. Further adjuvants may comprise DNA or oligonucleotides, like, inter alia, CpG-containing motifs (CpG-oligonucleotides; Krieg, Nature 374 (1995), 546-549; Pisetsky, An. Internal. Med. 126 (1997), 169-171).

The vaccines usually are administered by intravenous or intramuscular injection. Additional formulations which are suitable for other modes of administration include suppositories and, in some cases, oral formulations. For suppositories, traditional binders and carriers may include but are not limited to polyalkylene glycols or triglycerides. Oral formulation include such normally employed excipients as, for example, pharmaceutical grades of mannitol, lactose, starch, magnesium stearate, sodium saccharine, cellulose, magnesium carbonate and the like. These compositions may take the form of solutions, suspensions, tables, pills, capsules, sustained release formulations or powders and contain about 10% to about 95% of active ingredient, preferably about 25% to about 70%.

Vaccines are administered in a way compatible with the dosage formulation, and in such amounts as will be prophylactically and/or therapeutically effective. The quantity to be adminstered generally is in the range of about 5 micrograms to about 250 micrograms of antigen per dose, and depends upon the subject to be dosed, the capacity of the subject's immune system to synthesize antibodies, and the degree of protection sought. Precise amounts of active ingredient required to be administered also may depend upon the judgment of the practitioner and may be unique to each subject. The vaccine may be given in a single or multiple dose schedule. A multiple dose is one in which a primary course of vaccination may be with one to ten separate doses, followed by other doses given at subsequent time intervals required to maintain and/or to reinforce the immune response, for example, at one to four months for a second dose, and if required by the individual, a subsequent dose(s) after several months. The dosage regimen also will be determined, at least in part, by the need of the individual, and be dependent upon the practitioner's judgment. It is contemplated that the vaccine containing the immunogenic compounds of the invention may be administered in conjunction with other immunoregulatory agents, for example, with immunoglobulins, with cytokines or with molecules which optimize antigen processing, like listeriolysin.

In a preferred embodiment, the composition of the present invention is a diagnostic composition further comprising, optionally, suitable means for detection.

For diagnosis and quantification of pathogens like *Mycobacteria*, pathogenic fragments, their derivatives, their (poly) peptides (proteins), their polynucleotides, etc. in clinical and/or scientific specimens, a variety of immunological methods, as well as molecular biological methods, like nucleic acid hybridization assays, PCR assays or DNA Enzyme Immuno Assays (DEIA; Mantero et al., Clinical Chemistry 37 (1991), 422-429) have been developed and are well known in the art. In this context, it should be noted that the nucleic acid molecules of the invention may also comprise PNAs, modified DNA analogs containing amide backbone linkages. Such PNAs are useful, inter alia, as probes for DNA/RNA hybridization. The proteins of the invention may be, inter alia, useful for the detection of anti-pathogenic (like, e.g., anti-bacterial or anti-viral) antibodies in biological test samples of infected individuals. It is also contemplated that antibodies and compositions comprising such antibodies of the invention may be useful in discriminating acute from non-acute infections.

The diagnostic composition optionally comprises suitable means for detection. The proteins, antigenic fragments, fusion proteins and antibodies or fragments or derivatives thereof described above are, for example, suitable for use in immunoassays in which they can be utilized in liquid phase or bound to a solid phase carrier. Solid phase carriers are known to those in the art and may comprise polystyrene beads, latex beads, magnetic beads, colloid metal particles, glass and/or silicon chips and surfaces, nitrocellulose strips, membranes, sheets, animal red blood cells, or red blood cell ghosts, duracytes and the walls of wells of a reaction tray, plastic tubes or other test tubes. Suitable methods of immobilizing nucleic acids, (poly)peptides, proteins, antibodies, microorganisms etc. on solid phases include but are not limited to ionic, hydrophobic, covalent interactions and the like. Examples of immunoassays which can utilize said proteins, antigenic fragments, fusion proteins, antibodies or fragments or derivatives of said antibodies of the invention are competitive and non-competitive immunoassays in either a direct or indirect format. Commonly used detection assays can comprise radioisotopic or non-radioisotopic methods. Examples of such immunoassays are the radioimmunoassay (RIA), the sandwich (immunometric assay) and the Western blot assay. Furthermore, these detection methods comprise, inter alia, IRMA (Immune Radioimmunometric Assay), EIA (Enzym Immuno Assay), ELISA (Enzyme Linked Immuno Assay), FIA (Fluorescent Immuno. Assay), and CLIA (Chemiluminescent Immune Assay). Other detection methods that are used in the art are those that do not utilize tracer molecules. One prototype of these methods is the agglutination assay, based on the property of a given molecule to bridge at least two particles.

The proteins, antigenic fragments, antibodies, nucleic acid molecules and/or fusion proteins of the invention can be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention.

Appropriate labels and methods for labeling are known to those of ordinary skill in the art. Examples of the types of labels which can be used in the present invention include inter alia, fluorochromes (like fluorescein, rhodamine, Texas Red, etc.), enzymes (like horse radish peroxidase, β-galactosidase, alkaline phosphatase), radioactive isotopes (like $^{32}$P or $^{125}$I), biotin, digoxygenin, colloidal metals, chemi- or bioluminescent compounds (like dioxetanes, luminol or acridiniums).

A variety of techniques are available for labeling biomolecules, are well known to the person skilled in the art and are considered to be within the scope of the present invention and comprise, inter alia, covalent coupling of enzymes or biotinyl groups, iodinations, phosphorylations, biotinylations, random priming, nick-translations, tailing (using terminal transferases). Such techniques are, e.g., described in Tijssen, "Practice and theory of enzyme immuno assays", Burden, RH and von Knippenburg (Eds), Volume 15 (1985), "Basic methods in molecular biology"; Davis L G, Dibmer M D; Battey Elsevier (1990), Mayer et al., (Eds) "Immunochemical methods in cell and molecular biology" Academic Press, London (1987), or in the series "Methods in Enzymology", Academic Press, Inc.

Detection methods comprise, but are not limited to, autoradiography, fluorescence microscopy, direct and indirect enzymatic reactions, etc.

Said diagnostic composition may be used for methods for detecting a pathogenic organism in a biological and/or medical sample and/or for detecting expression of a protein or a nucleic acid molecule of the invention by detecting the presence of mRNA coding for a protein of the invention which comprises, for example, obtaining mRNA from pathogen preparations (like bacterial or viral preparations) and contacting the mRNA so obtained with a probe/primer comprising a nucleic acid molecule capable of specifically hybridizing with a nucleic acid molecule of the invention under suitable conditions and detecting the presence of mRNA hybridized to the probe/primer. Further diagnostic methods leading to the detection of nucleic acid molecules in a sample comprise, e.g., polymerase chain reaction (PCR), ligase chain reaction (LCR), Southern blotting in combination with nucleic acid hybridization, comparative genome hybridization (CGH) or representative difference analysis (RDA). These methods for assaying for the presence of nucleic acid molecules are known in the art and can be carried out without any undue experimentation.

The invention relates further to a method for the production of a vaccine against a virulent strain of the genus *Mycobacterium* comprising the steps of (a) recombinant expression of a differentially expressed protein as defined above, an antigenic fragment as defined above or the fusion protein of the invention, and (b) combining said recombinantly expressed differentially expressed protein, antigenic fragment or fusion protein with a pharmaceutically acceptable carrier.

Furthermore, the invention relates to a method for the production of a vaccine against a virulent strain of the genus *Mycobacterium* by combining a vector comprising a nucleic acid molecule encoding a differentially expressed protein, an antigenic fragment or the fusion protein of the invention with a biologically acceptable carrier, wherein said nucleic acid molecule in said vector is placed under the control of an expression control sequence.

Moreover, the invention relates to the use of a nucleic acid molecule encoding a differentially expressed protein, an antigenic fragment as defined above or the fusion protein of the invention for the methods as described herein.

The invention further relates to the use of at least one of the proteins, an antigenic fragment, a nucleic acid molecule, a fusion protein or the antibody or fragments or derivatives thereof as defined herein for the preparation of a composition for the treatment of a *Mycobacteria*-induced disease.

The invention further relates to the use of at least one of the proteins, an antigenic fragment, a nucleic acid molecule, a fusion protein or the antibody or fragments or derivatives thereof as defined herein for the preparation of a vaccine for vaccination against a *Mycobacteria*-induced disease.

In a preferred embodiment of the use of the present invention said *Mycobacteria* induced disease is selected from the group consisting of tuberculosis, leprosy, tropical skin ulcer, ulceration, abscess, pulmonary disease, granulomatous (skin) disease, opportunistic infections with non-tuberculous mycobacteria as well as from diseases elicited by atypical mycobacteria such as *M. avium* including pulmonary disease, lymphadenitis, cutaneous and disseminated diseases, e.g. in immunocompromised patients. The use is not restricted to *Mycobacteria*-induced diseases in humans but comprises also the use of the present invention in animal diseases, like bovine tuberculosis.

Figure 1B:
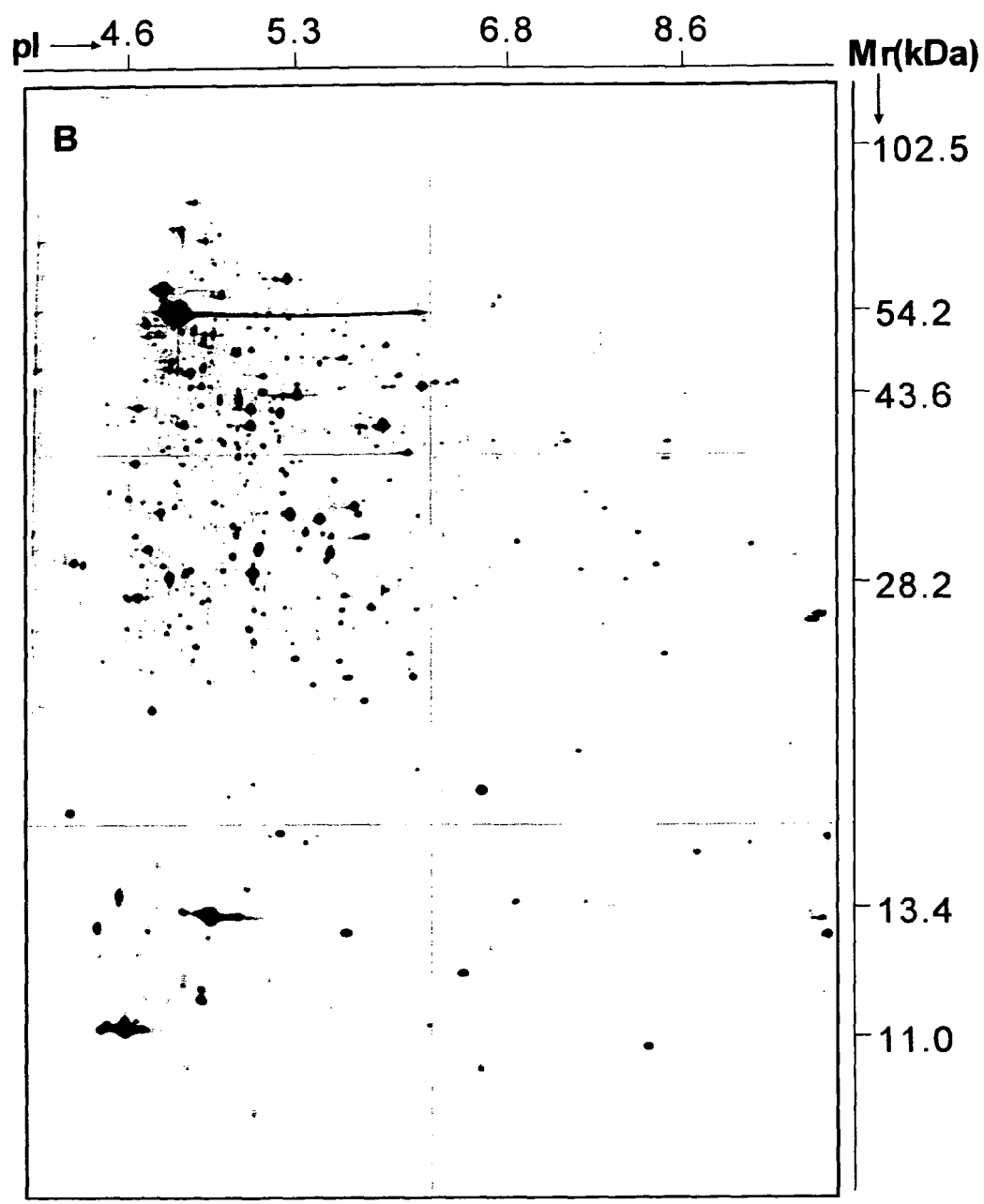

The figures show:

FIG. 1: 2-DE gel of total cell protein of (A) *M. bovis* BCG, (B) *M. tuberculosis* H37Rv and (C) culture supernatant of H37Rv.

FIG. 2: 2-DE pattern of *M. bovis* BCG Chicago cell proteins in 6 sectors (2a-2f). Identified proteins are marked with accession numbers corresponding to the accession numbers in Table 1.

FIG. 3: 2-DE pattern of *M. tuberculosis* H37Rv culture supernatant in 6 sectors (3a-3f). Identified proteins are marked with accession numbers corresponding to the accession numbers in Table 1.

FIG. 4: Pattern sectors showing differences in intensity or position between cell proteins of different mycobacterial strains.

a) Comparison between A, C, E, *M. bovis* BCG Chicago and B, D, F, *M. tuberculosis* H37Rv. C645 is a mobility variant of C527. Both spots were identified as succinyl-CoA synthase α- chain (Rv 0952). C126 and C125 are mobility variants, both identified as oxidoreductases of aldo/keto reductase family (Rv2971). C31 is increased in intensity in BCG Chicago as compared with C53 of H37Rv. This protein was identified as alkyl hydroperoxide reductase chain C(Rv2428). C71 is absent in BCG Chicago and was identified as MPT64 (Rv1980c).

b) Comparison of A and C, *M. tuberculosis* H37Rv with B and D, Erdman. Proteins of the glutamate family are increased in intensity in the Erdman pattern: A511 and A195 and their corresponding spots in H37Rv A386 and B17 are acetylornithine amino transferases ArgD (Rv1655) and D20 is N-acetyl-glutamylphosphate reductase (Rv1652). Two spots in A and B are shifted to a more acidic position in the Erdman pattern. A473 and A267 were identified as transcriptional regulator MoxR(Rv1479). The region shown in C and D reveals 3 intensity differences: D59 was identified as Rv 3213c; D153 as Rv1996; and D10 as haloalkane dehalogenase Rv2296.

Figure 5:
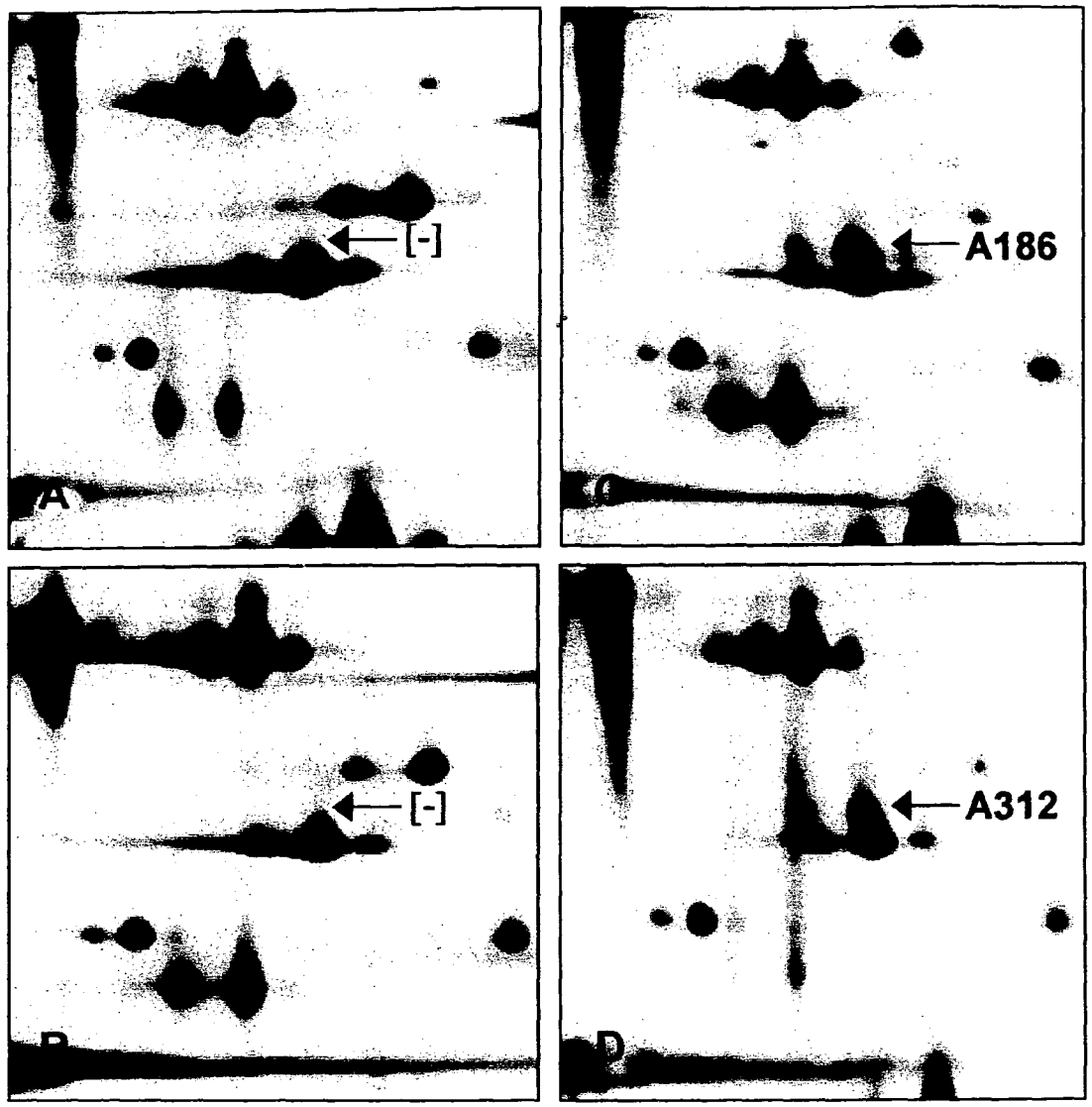
Figure 5:
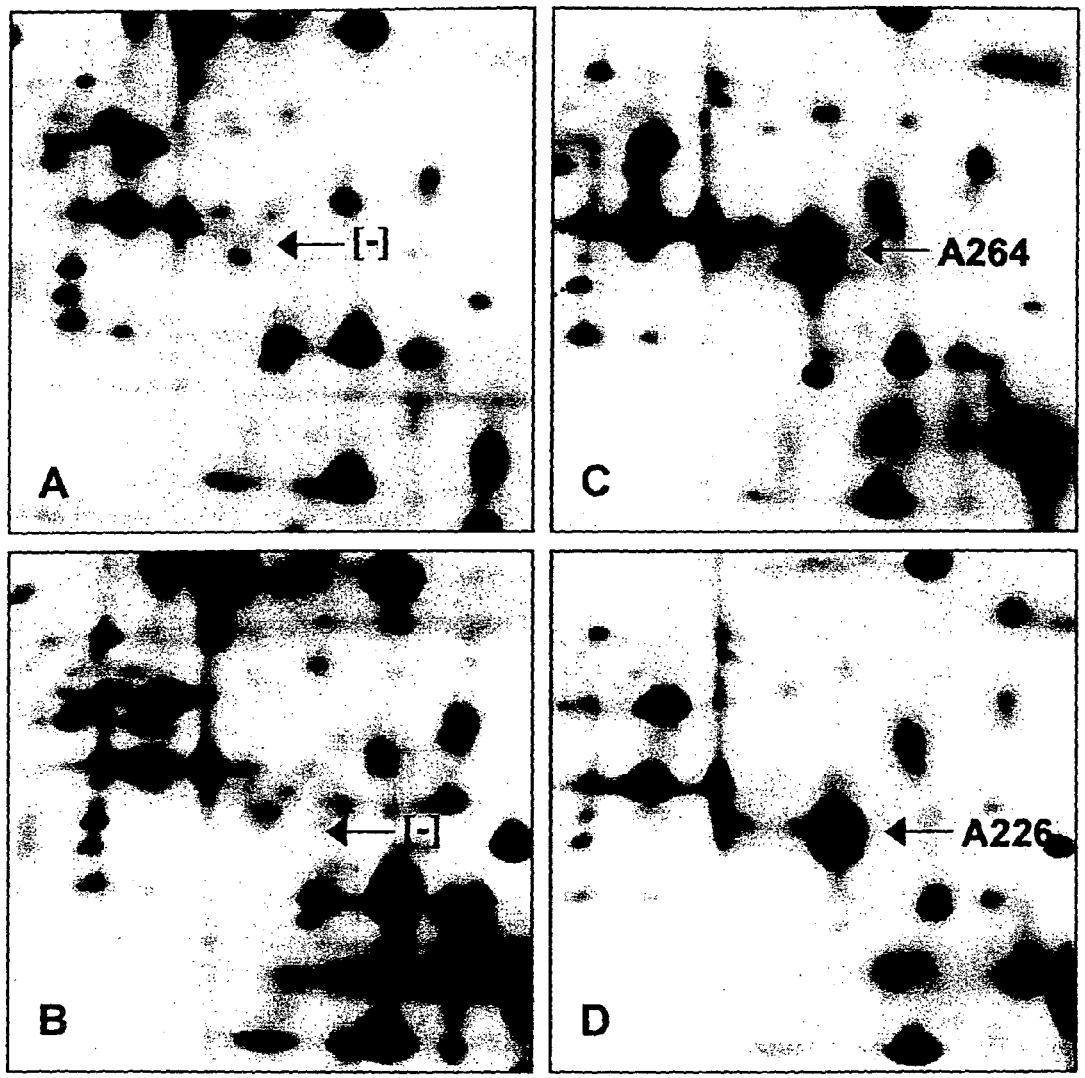
Figure 5:
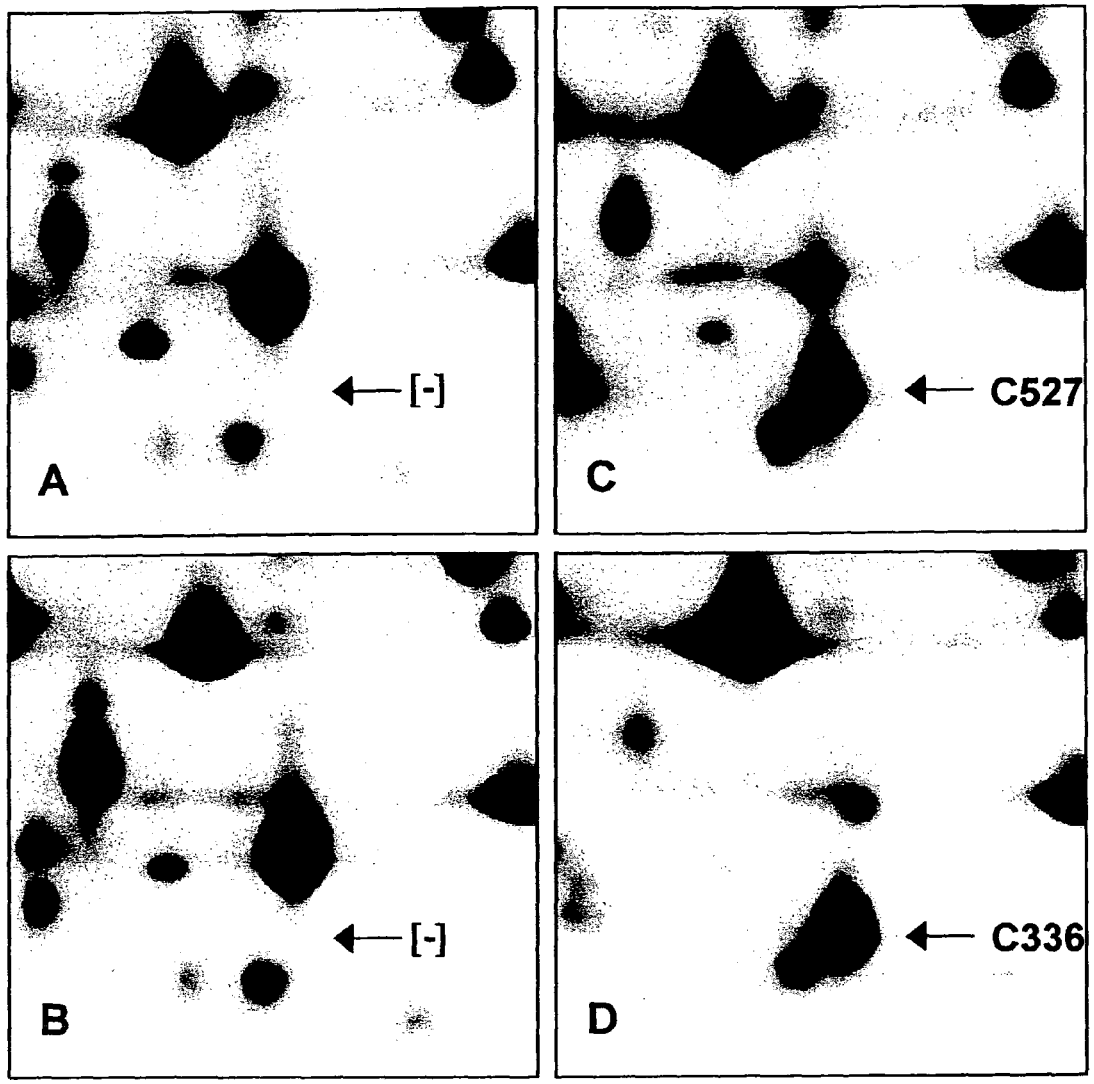
Figure 5:
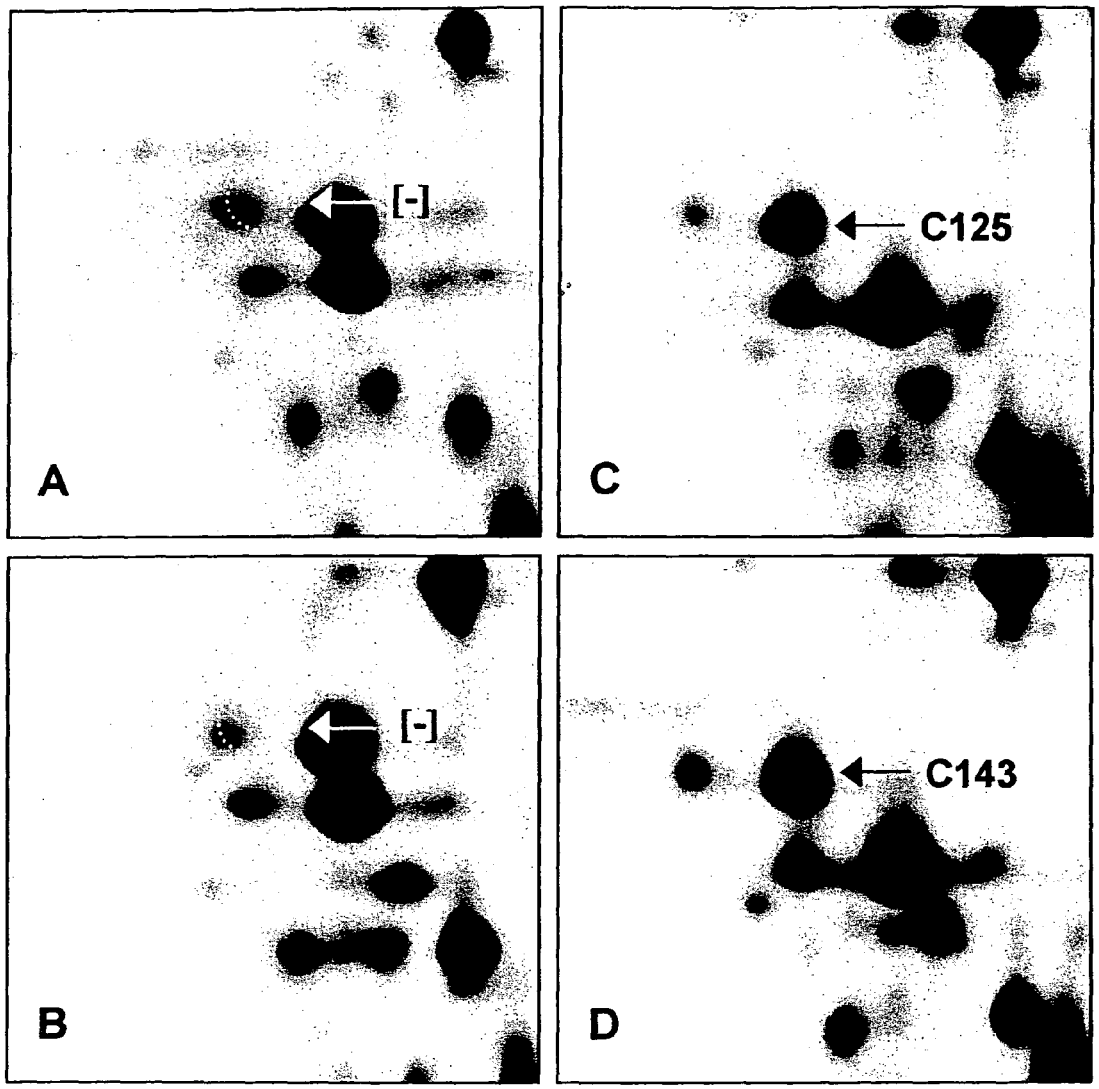
Figure 5:
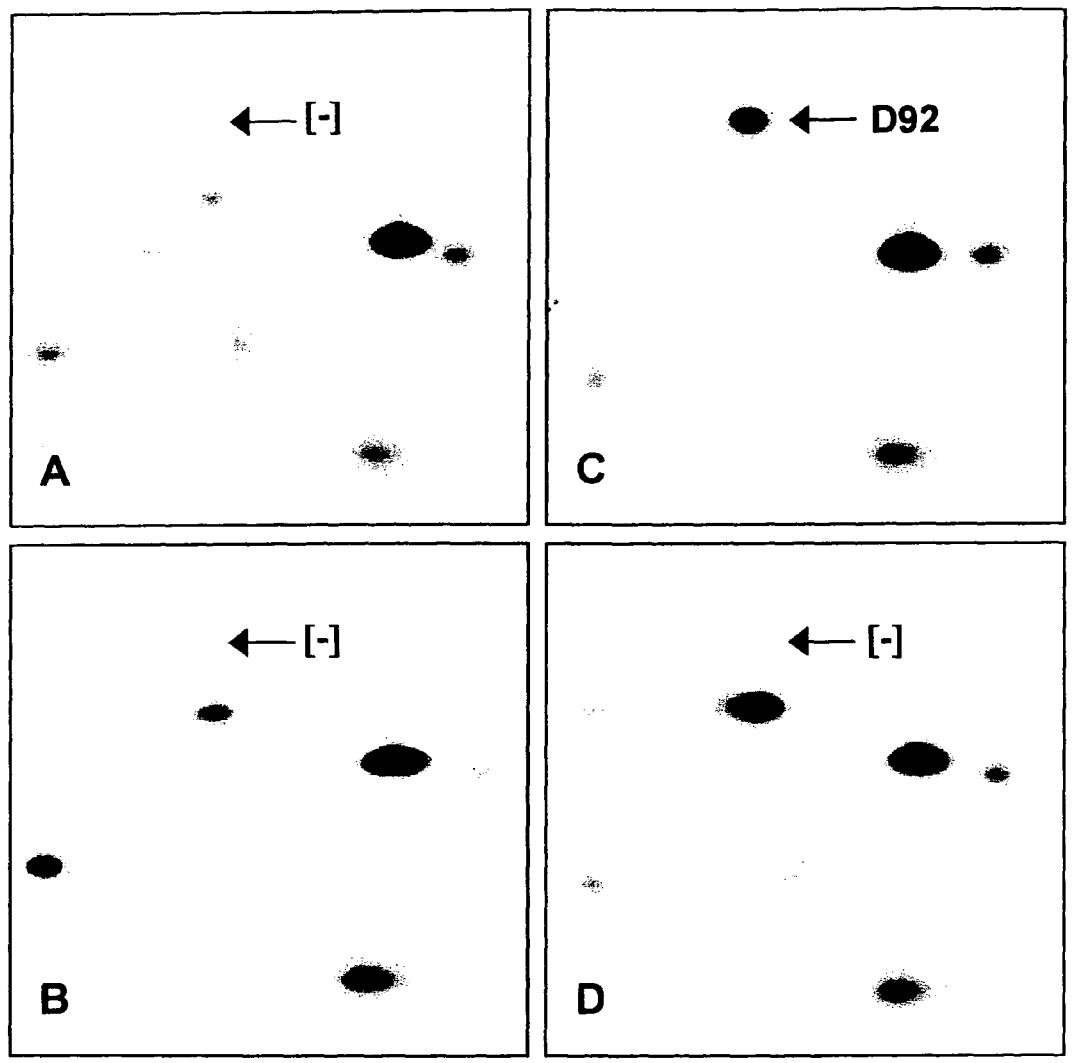
Figure 5:
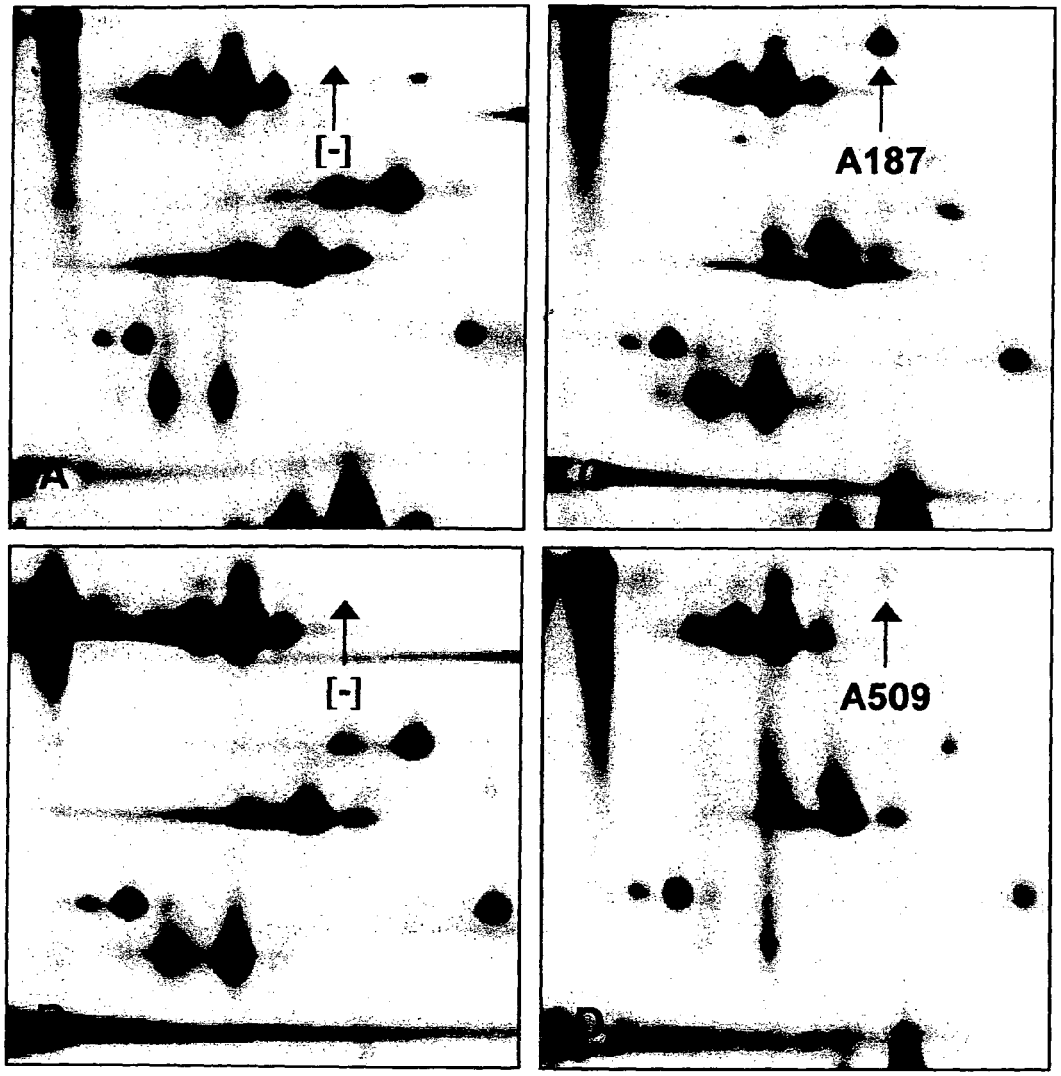
Figure 5:
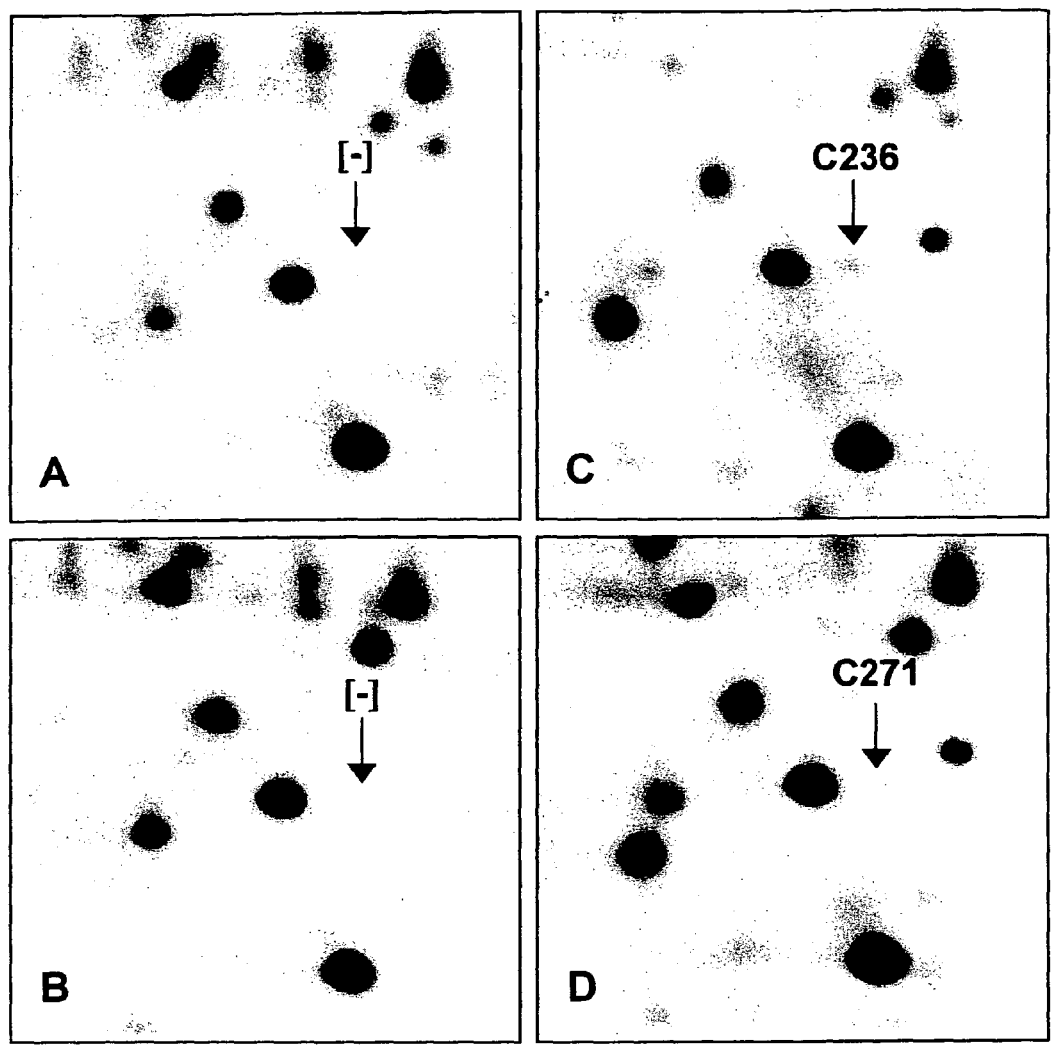
Figure 5:
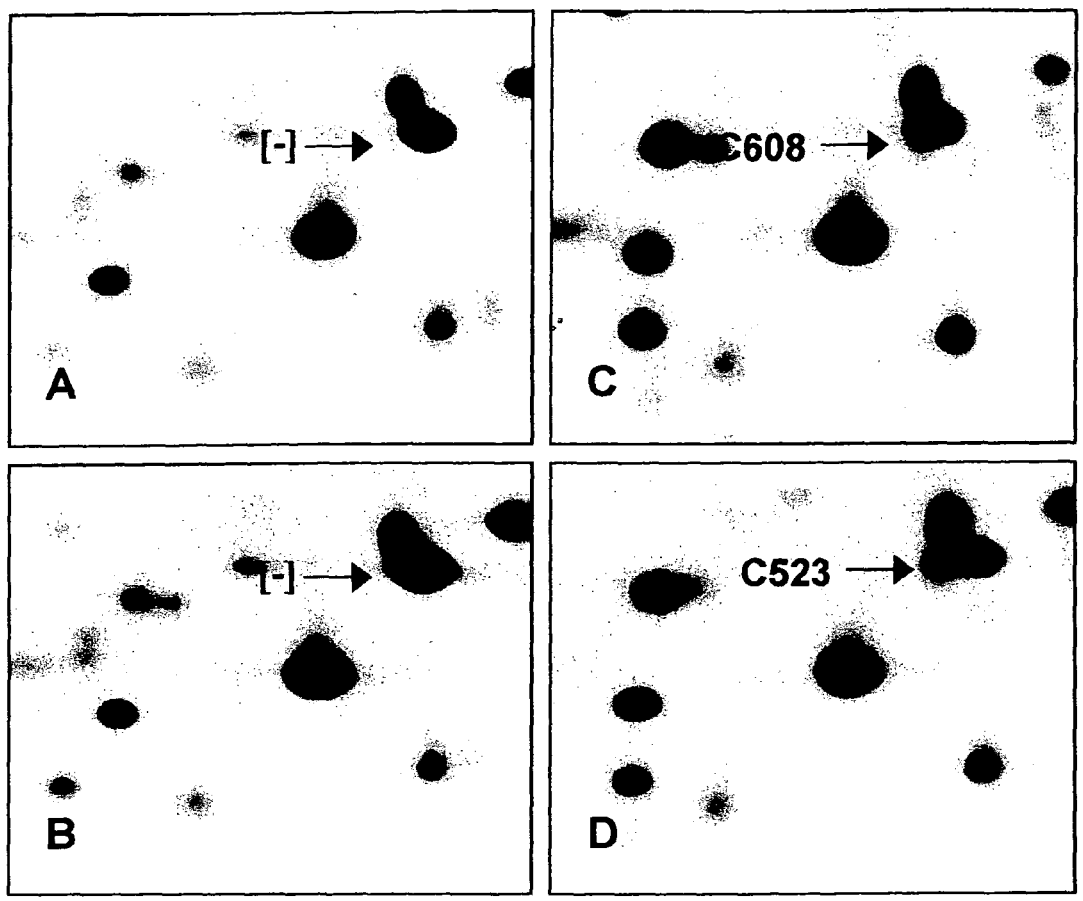
Figure 5:
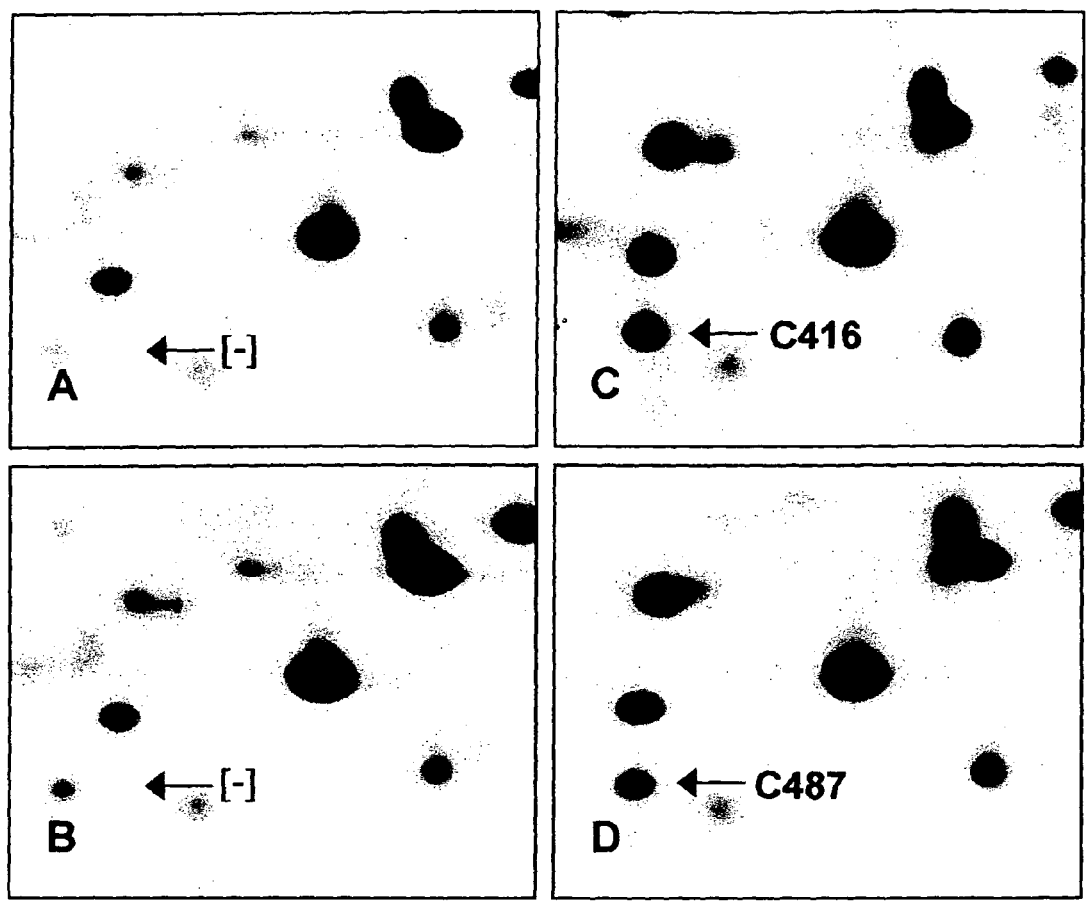
Figure 5:
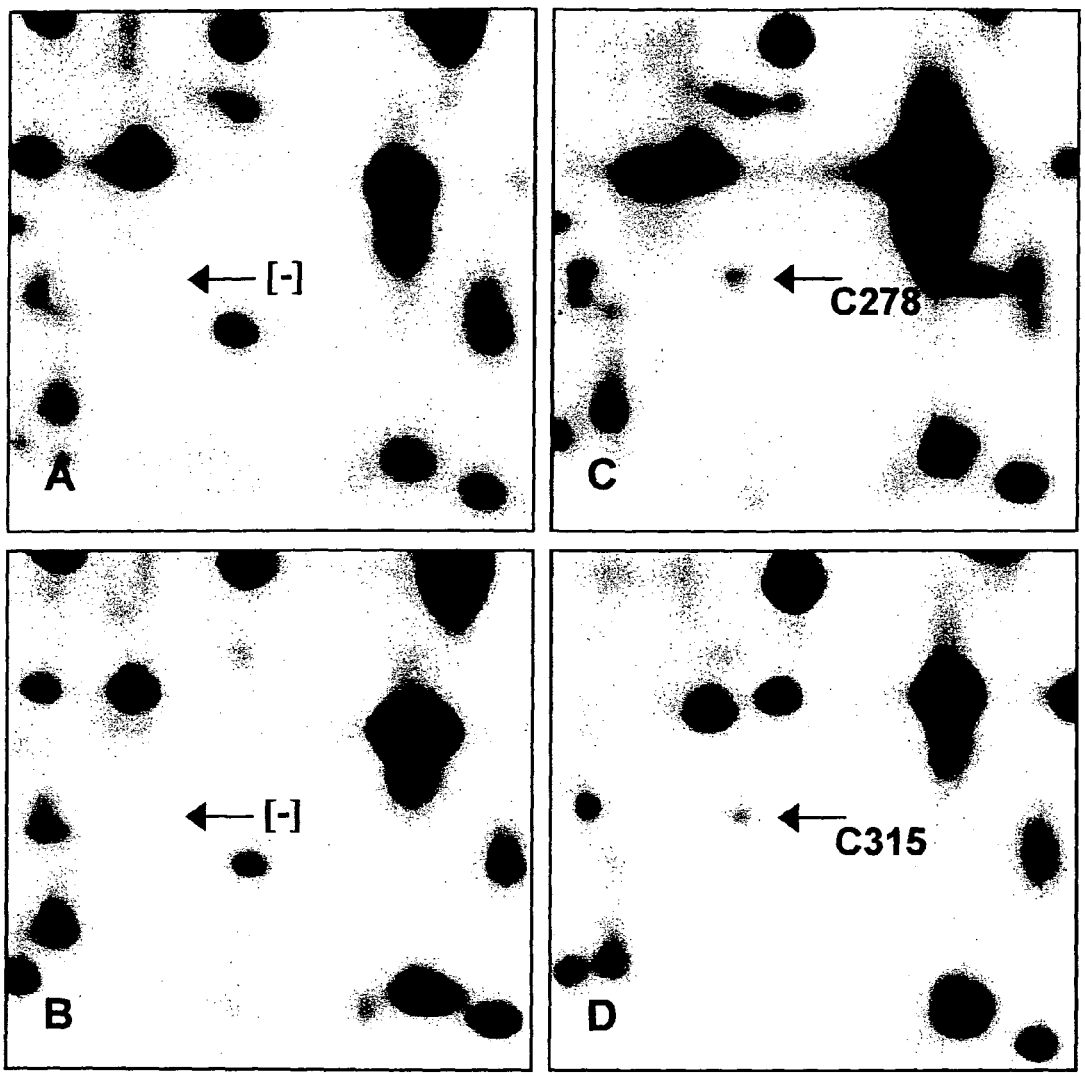
Figure 5:
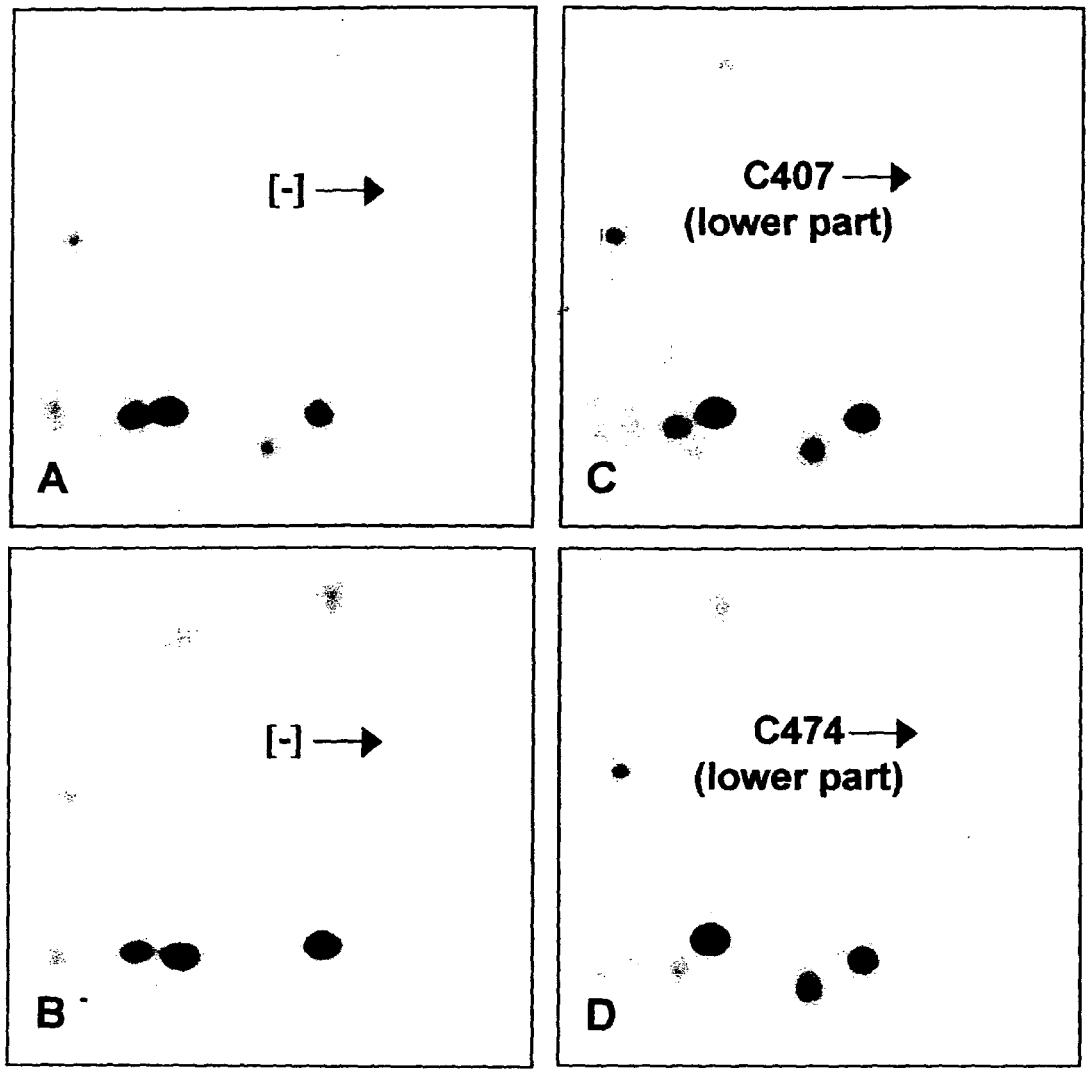
Figure 5:
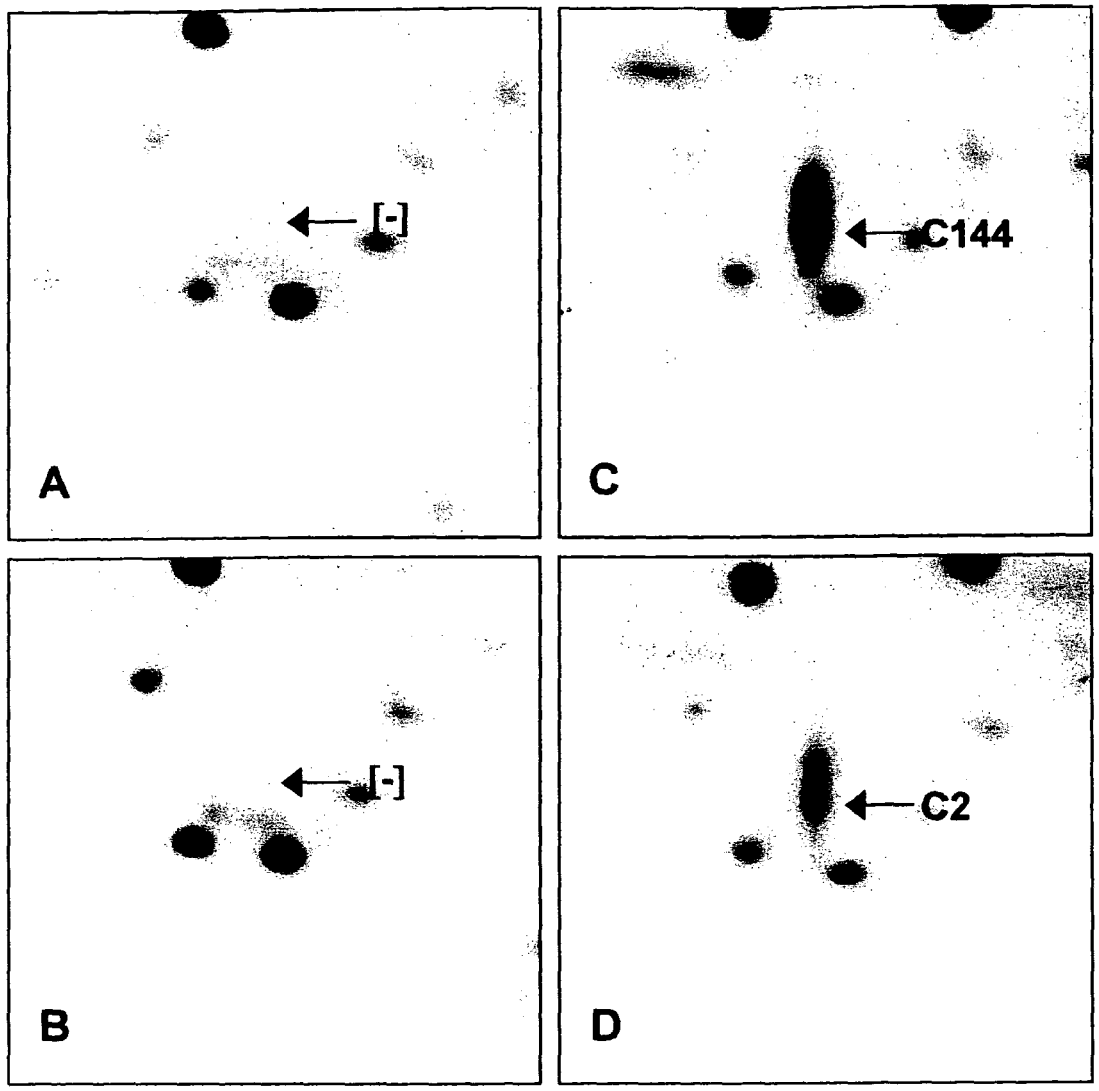
Figure 5:
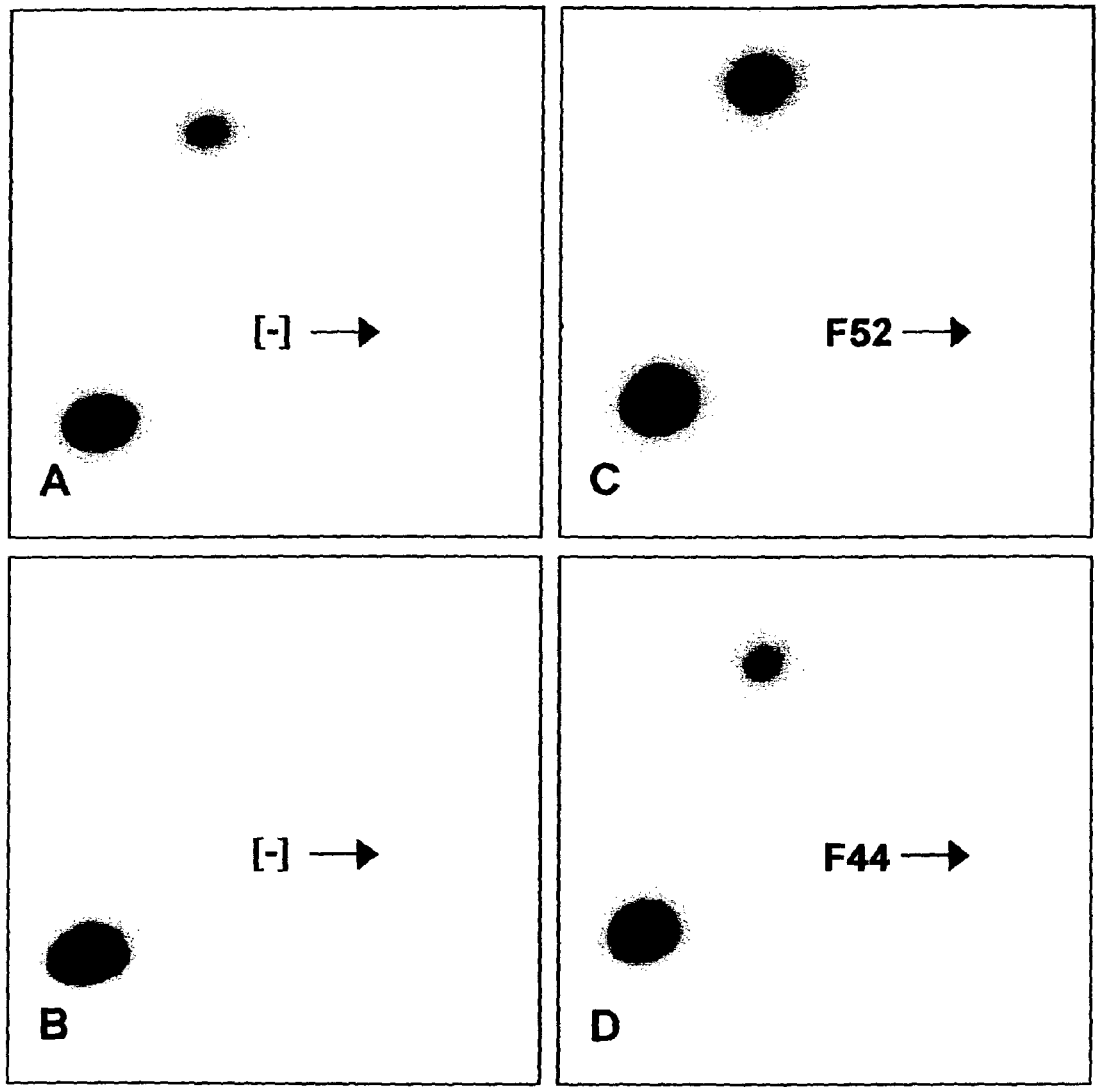
Figure 5:
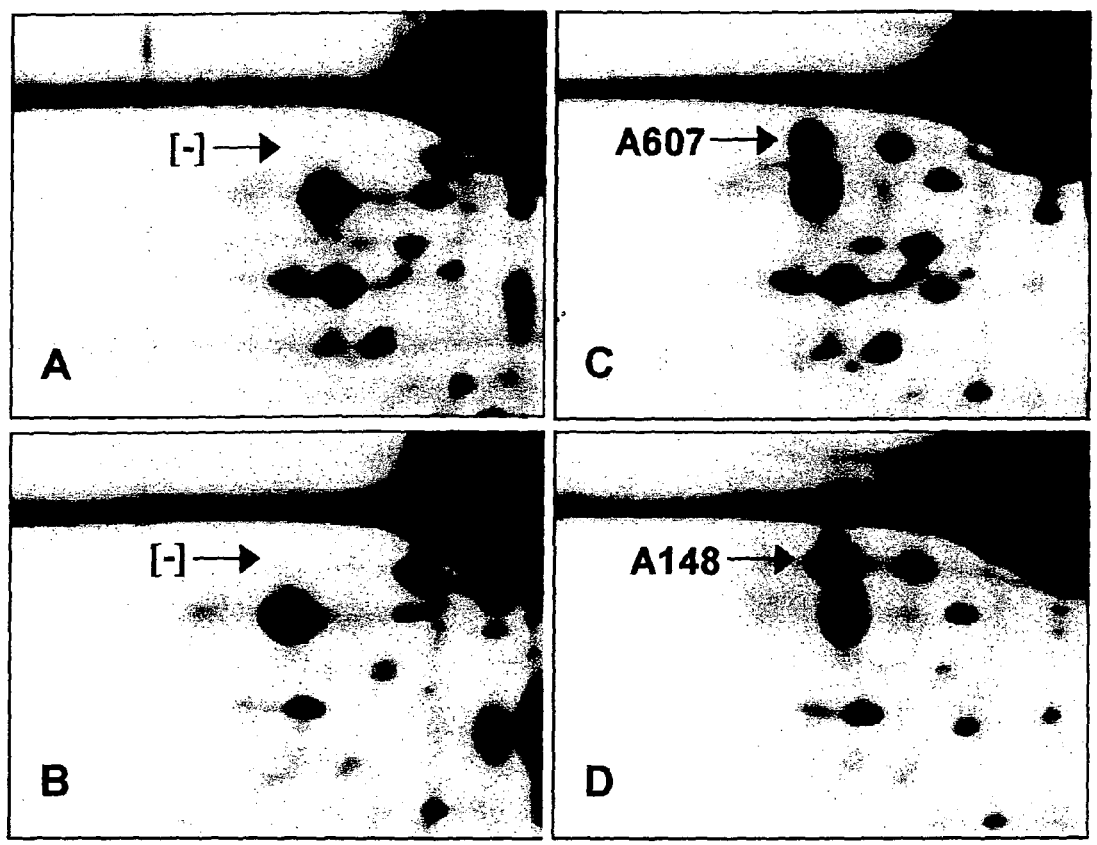
Figure 5:
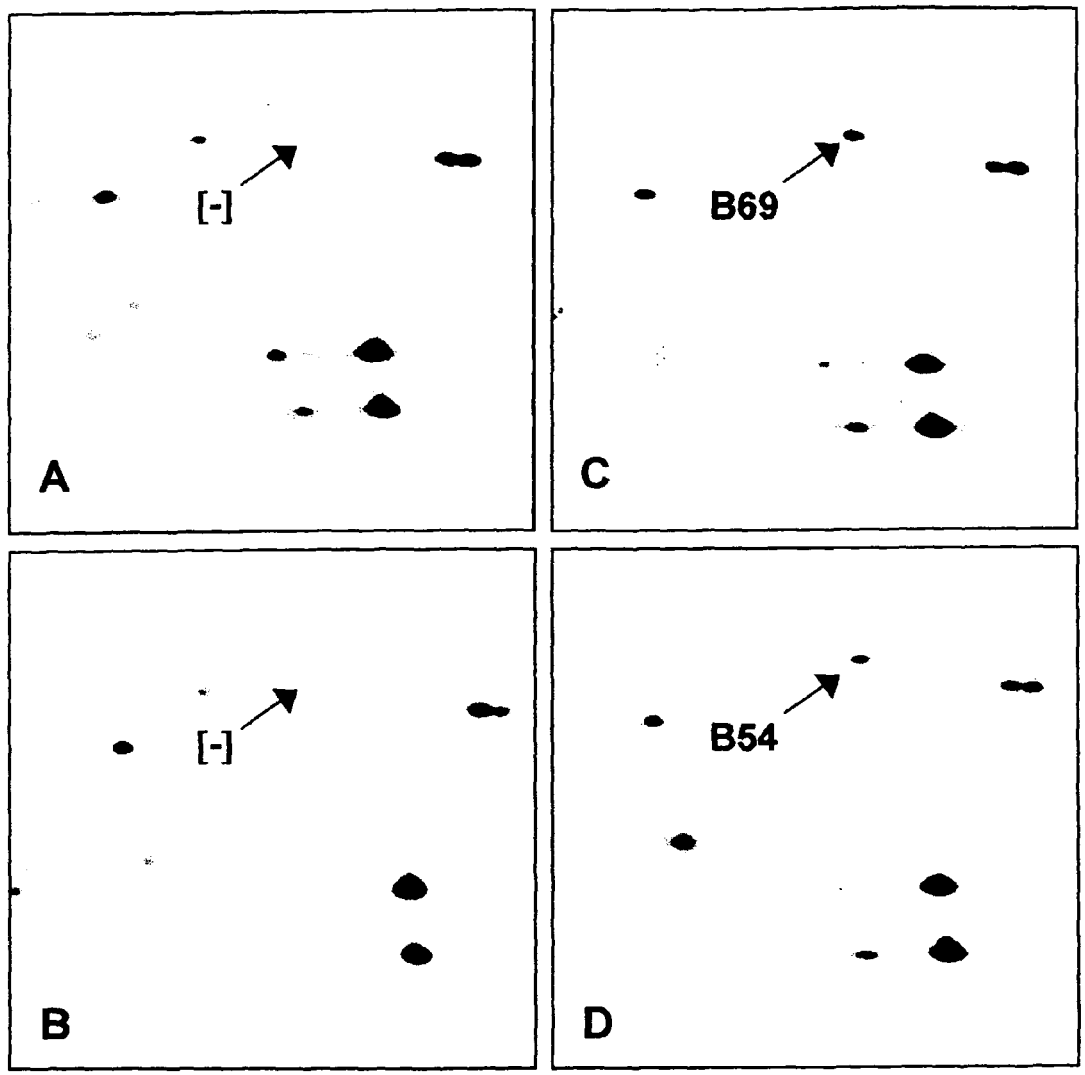
Figure 5:
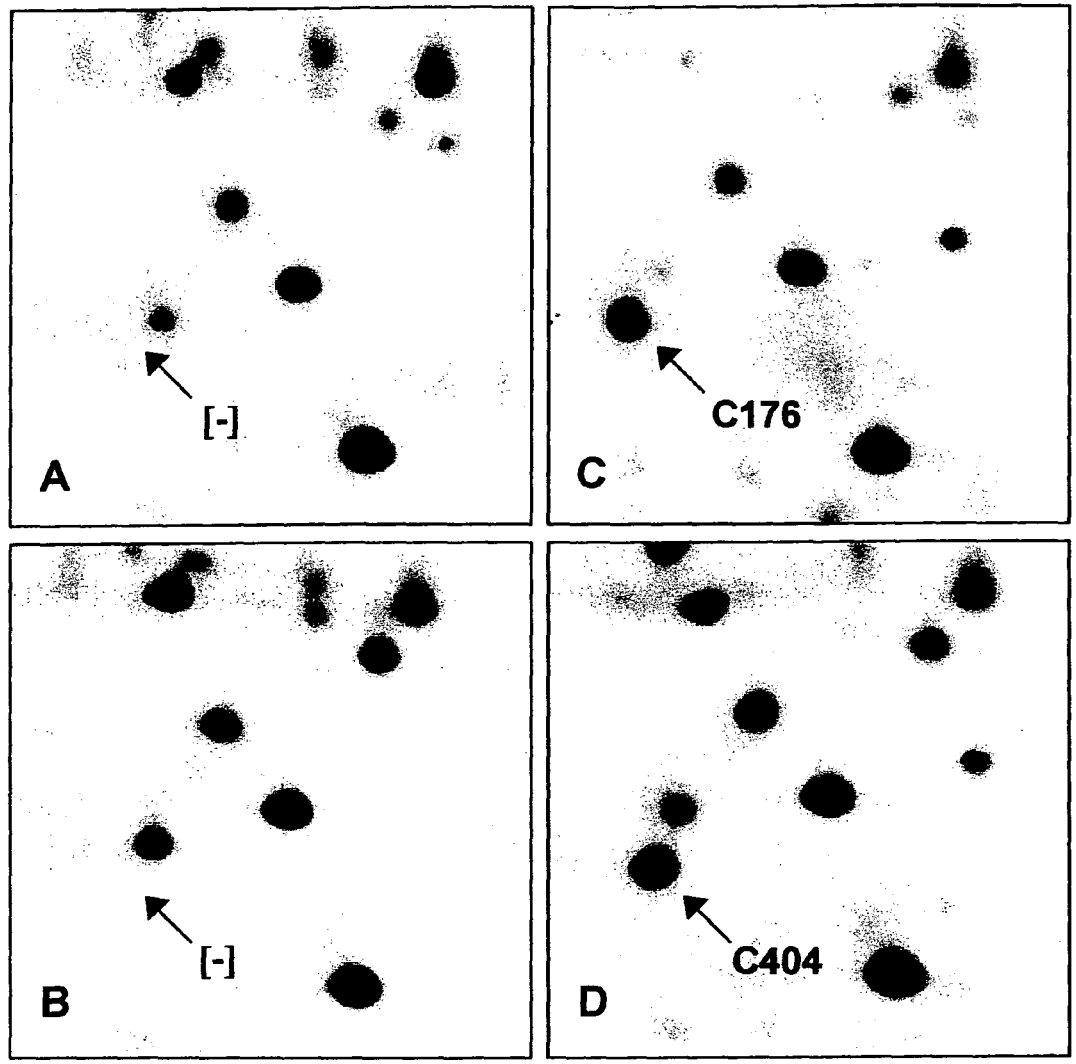
Figure 5:
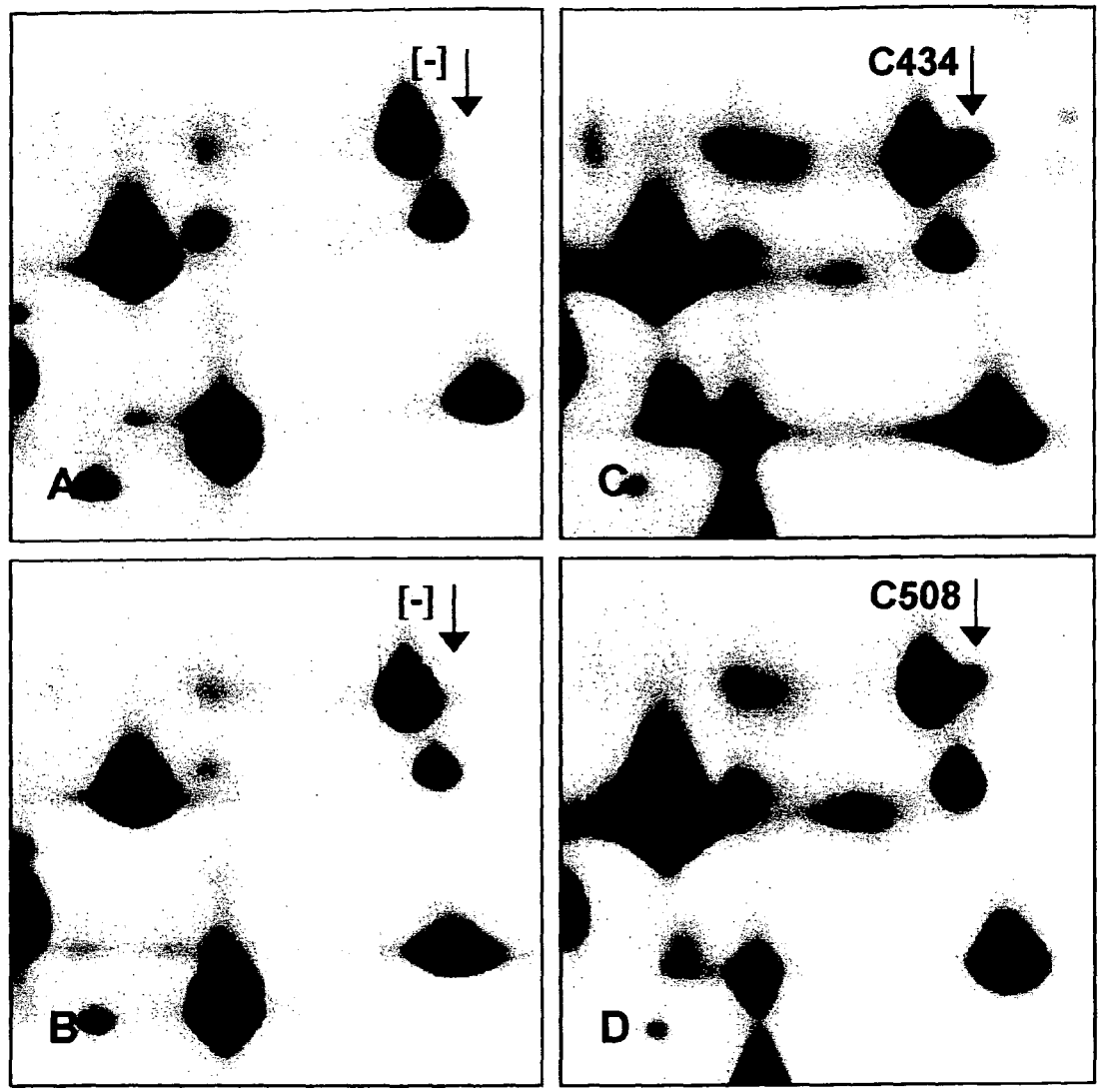
Figure 5:
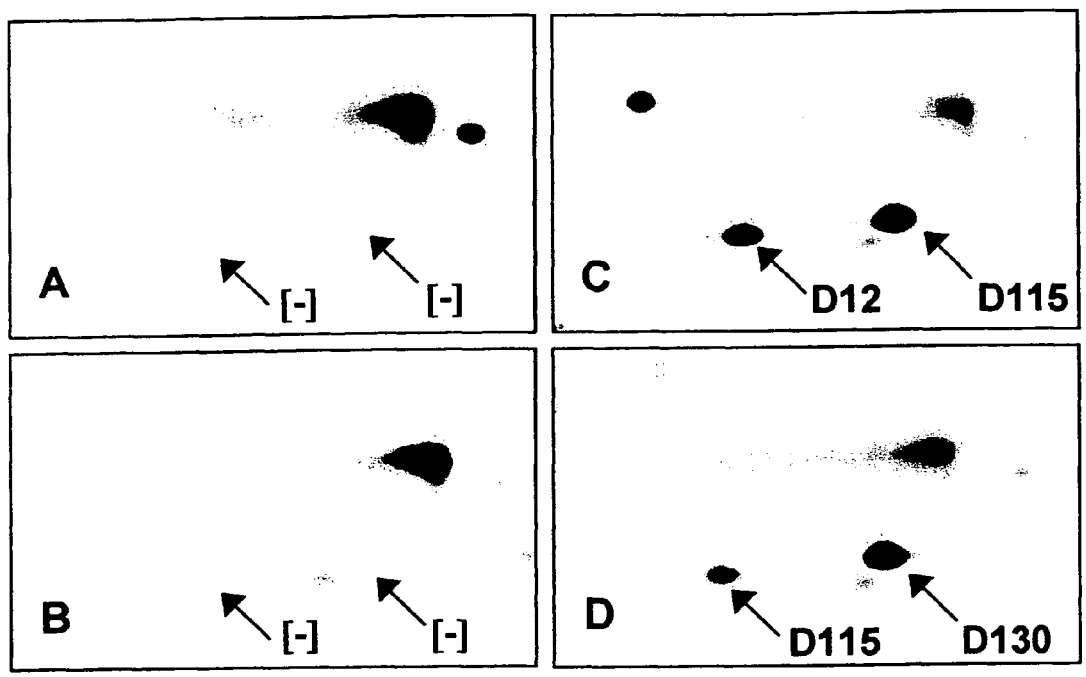

FIG. 5: Pattern areas showing +/− differences or mobility variants between cell proteins of different mycobacterial strains. A, *M. bovis* BCG Chicago; B, *M. bovis* BCG Copenhagen; C, *M. tuberculosis* H37Rv; D, *M. tuberculosis* Erdman. The spots indicated by arrows were only detected on the patterns of the virulent strains *Mycobacterium tuberculosis* H37Rv and *Mycobacterium tuberculosis* Erdman.

a) The proteins A186 of *M. tuberculosis* H37Rv and A312 of *M. tuberculosis* Erdman were identified as 2-isopropylmalate synthase (LeuA) expressed from the gene Rv3710.

b) The proteins A264 of *M. tuberculosis* H37Rv and A226 of *M. tuberculosis* Erdman were identified as s-adenosylmethionine synthase (MetK) expressed from the gene Rv1392.

c) The proteins C527 of *M. tuberculosis* H37Rv and C336 of *M. tuberculosis* Erdman were identified as succinyl CoA synthase alpha chain (SucD) expressed from the gene Rv0952.

d) The proteins C125 of *M. tuberculosis* H37Rv and C143 of *M. tuberculosis* Erdman were identified as oxidoreductase of aldo/keto reductase family expressed from the gene Rv2971.

e) The protein D92 of *M. tuberculosis* H37Rv was identified as oxireductase expressed from the gene Rv0068.

f) The proteins A187 of *M. tuberculosis* H37Rv and A509 of *M. tuberculosis* Erdman were identified as elongation factor G (FusA2) expressed from the gene Rv0120c.

g) The proteins C236 of *M. tuberculosis* H37Rv and C271 of *M. tuberculosis* Erdman were identified as uridylate kinase (PyrH) expressed from the gene Rv2883c.

h) The proteins C608 of *M. tuberculosis* H37Rv and C523 of *M. tuberculosis* Erdman were identified as ABC-type transporter expressed from the gene Rv1463.

i) The proteins C416 of *M. tuberculosis* H37Rv and C487 of *M. tuberculosis* Erdman were identified as short-chain dehydrogenase/reductase family expressed from the gene Rv1856c.

j) The proteins C278 of *M. tuberculosis* H37Rv and C315 of *M. tuberculosis* Erdman were identified as 1,3,4,6-tetrachloro-1,4-cyclohexadiene hydrolase (LinB) expressed from the gene Rv2579.

k) The proteins C407 (lower part) of *M. tuberculosis* H37Rv and C474 (lower part) of *M. tuberculosis* Erdman were identified as phosphoribosylaminoimidazole carboxylase catalytic subunit (PurE) expressed from the gene Rv3275c.

l) The proteins C144 of *M. tuberculosis* H37Rv and C2 of *M. tuberculosis* Erdman were identified as hypothetical protein expressed from the gene Rv2557.

m) The proteins F52 of *M. tuberculosis* H37Rv and F44 of *M. tuberculosis* Erdman were identified as hypothetical protein expressed from the gene Rv3407.

n) The proteins A607 of *M. tuberculosis* H37Rv and A148 of *M. tuberculosis* Erdman were identified as hypothetical protein expressed from the gene Rv3881c.

o) The proteins B69 of *M. tuberculosis* H37Rv and B54 of *M. tuberculosis* Erdman were identified as hypothetical protein expressed from the gene Rv2449c.

p) The proteins C176 of *M. tuberculosis* H37Rv and C404 of *M. tuberculosis* Erdman were identified as hypothetical protein expressed from the gene Rv0036c.

q) The proteins C434 of *M. tuberculosis* H37Rv and C508 of *M. tuberculosis* Erdman were identified as hypothetical protein expressed from the gene Rv2005c.

r) The proteins D12 of *M. tuberculosis* H37Rv, D115 of *M. tuberculosis* H37Rv, D115 of *M. tuberculosis* Erdman and D130 of *M. tuberculosis* Erdman were identified as transcriptional regulator (Crp/Fnr family) expressed from the gene Rv3676.

The invention will now be illustrated by reference to the following examples which are merely illustrative and are not to be construed as being a limitation of the scope of the present invention.

EXAMPLE 1

Mycobacterial Strains and their Culturing Conditions

*M. tuberculosis* H37Rv and Erdman as well as *M. bovis* BCG Chicago and Copenhagen (*M. tub*. H37Rv and Erdman, BCG Chicago from: Stammsammlung MPI für Infektionsbiologie, Berlin, BCG Copenhagen from: Statensernen Instittutet, Kopenhagen) were grown in Middlebrook medium (900 ml Difco 0713-01-7+100 ml ADC enrichment 0714-64-0) for 6-8 days at 37° C.; to a cell density of $10^8$ cells per ml. For the preparation of culture supernatant proteins (CSN), mycobacterial strains were grown in Sauton medium (per 4 l of Sauton medium enriched with pyruvic acid sodium salt glucose: 16.00 g asparagine, 2.00 g magnesiumsulphate-heptahydrate p.A., 8.00 g citric acid monohydrate, 2.00 g dipotassium hydrogenphosphate, 0.20 g ferri-ammoniumcitrate, 19.28 g D(+)-glucose monohydrate, 19.28 g pyruvic acid sodium salt, 240 ml glycerol (86-88%)) under permanent shaking for 10 to 15 days at 37° C. or without shaking for 30 days at 37° C. until a cell density of $1-2\times10^8$ cells per ml was reached.

EXAMPLE 2

Protein Separation and Identification Strategy for Differentially Expressed Proteins (Proteome Analysis)

Proteome analysis of a biological entity depends on separation methods appropriate for the complexity of the system. Whereas proteomes of ribosomes containing about 50-100 protein species can be investigated by small 2-DE systems (Kaltschmidt (1970), *Anal. Biochem.* 36: 401) or high-performance liquid chromatography (Kamp (1984), *J. Chro-* matogr. 317: 181), proteome analysis of bacterial and higher organisms requires high-resolution techniques. The combination of isoelectric focusing and SDS-PAGE, both per se high-resolution methods (Vesterberg(1966), *Acta Chem. Scand.* 20: 820; Laemmli (1970), *Nature* 227: 680), and the use of large-sized gels (at least 20 cm×30 cm) results in a resolution power of 5,000-10,000 protein species with sufficient quality to allow the comparison of gels between different laboratories (Jungblut (1994), *Electrophoresis* 15: 685; Klose (1995), *Electrophoresis* 16: 1034).

Two virulent strains of *M. tuberculosis*, H37Rv and Erdman, and two vaccine strains, *M. bovis* BCG Chicago and Copenhagen, were analyzed. In order to prepare a cell protein fraction (CP), mycobacteria were as described in Example 1. The cells were washed in PBS and sonicated in the presence of proteinase inhibitors (TLCK: 100 µg/ml, E64: 25 µg/ml, Leupeptin: 50 µg/ml, Pepstatin A: 50 µg/ml), and the proteins were treated with 9 M urea, 70 mM DTT 2% ampholytes pH 2-4 (Serva Biochemicals, Germany) and 2% Triton X-100 to obtain completely denatured and reduced proteins. Culture supernatant proteins (CSN) were prepared from mycobacterial cultures grown in Sauton medium as described in Example 1. CSNs were collected by filtration and precipitation in 10% trichloroacetic acid. Samples were prepared according to standard methods and applied onto 2-DE gel systems (Klose, (1995), loc. cit., Jungblut (1999), loc. cit.).

For the resolution of the mycobacterial proteome, a 2-DE gel system in a 23 cm×30 cm version was applied and a resolution power of about 5,000 protein species was achieved. For subtractive analyses (as described in Aebersold (1990), *Electrophoresis* 11: 517) and database construction, 0.75 mm thick gels in the second dimension were used and silver staining was applied on these gels (Jungblut (1990), *J. Biochem. Biophys. Meth.* 21: 47). In order to identify proteins 1.5 mm thick gels were produced and the proteins were detected by Coomassie Brilliant Blue R250 (Eckerskorn (1988), *Electrophoresis* 9: 830) or G250 (Doherty (1998), *Electrophoresis* 19: 355), or negative staining (Fernandez-Patron (1995), *Anal. Biochem.* 224: 203).

The 2-DE pattern of all strains investigated are highly similar and since many landmark spots are known, these patterns are easily comparable. Only obvious differences readily recognizable by visual evaluation were employed to detect protein species from different mycobacterial strains with regard to intensity or position. Each comparison was repeated at least three times with different sample preparations of the same strains. Only differences confirmed in all preparations were accepted as strain specific.

Identification of proteins separated by 2-DE has been reviewed (Patterson (1995), Electrophoresis 16: 1791; P. Jungblut (1996), Electrophoresis 17: 839; Jungblut (1997), Mass Spectrometry Reviews 16: 145) 2-DE combines iso-electric focusing in the first dimension with SDS-PAGE (Sodiumdodecyl sulfate polyacrylamide gel electrophoresis) in the second dimension. The proteins are separated by two independent parameters, charge and molecular mass. Single amino acid changes may be detected. The resolution power of the used technique (gel size 23 cm×30 cm) is about 5000 protein species, which should be sufficient for a microorganism with about 3700 genes like *Mycobacterium tuberculosis* or *bovis*. The term protein species is defined as the smallest unit of a protein classification, defined by its chemical structure. In-gel tryptic digestion (Otto (1996), Electrophoresis 17: 1643) and MALDI-MS peptide mass fingerprinting (Henzel (1993), Proc. Natl. Acad. Sci. U.S.A. 90: 5011; Pappin (1993), Current Biology 3: 327; Mann (1993), Biol. Mass Spectrom. 22: 338; James (1993), Biochem. Biophys. Res. Commun. 195: 58) with the possibility of sequencing by post-source decay MALDI-MS (Spengler (1992), Rapid Commun. Mass Spectrom. 6: 105) were chosen in order to identify the first 263 proteins, with a priority for high intensity proteins and for variants between the investigated mycobacteriai strains. Peptide mass fingerprints were searched using the program MS-FIT (prospector.ucsfedu/ucsfhtml/ms-fit.htm) reducing the proteins of the NCBI database to the mycobacteriai proteins and to a molecular mass range estimated from 2-DE+/−20%, allowing a mass accuracy of 0.1 Da for the peptide mass. In the absence of matches the MOLECULAR mass window was extended. Partial enzymatic cleavages leaving two cleavage sites, oxidation of methionine, pyro-glutamic acid formation at N-terminal glutamine and modification of cysteine by acrylamide were considered in these searches.

The employed 2-DE methodology led to a resolution of the mycobacterial proteome into 1,800 distinct protein species. The composition of cellular as well as culture filtrate proteins of two strains of *M. tuberculosis* and of *M. bovis* BCG was compared. Hereby, 263 proteins have already been identified, 157 and 53 in the cell protein (CP) fraction of *M. bovis* BCG Chicago and *M. tuberculosis* (H37Rv and Erdman), respectively, as well as 53 proteins from H37Rv culture filtrate (CSN). From the CP patterns 8 proteins were unique for BCG, and 13 for *M. tuberculosis* H37Rv. Identification was performed by peptide mass fingerprinting (PMF) using matrix-assisted laser desorption/ionization (MALDI)-mass spectrometry and if necessary by confirmation with post-source decay (PSD) sequencing.

EXAMPLE 3

Format of Mycobacterial 2-DE Databases for Electronic Access

Data obtained as described in Example 2 and 8 are shown in FIGS. 1 to 5 and illustrated in Tables 1 to 4. Further information is available via internet (www.mpiib-berlin.mpg.de/2DPAGE/). The 2D-PAGE database complies with all rules according to the World 2D-PAGE guidelines for building a federated database (Appel (1996), Electrophoresis 17: 540). To navigate through the database, a Java compatible browser is required (e.g. Netscape 4.0 or internet Explorer 4.0). The program consists of common gateway interface (CGI) scripts written in PERL. One set of data comprises three files. The link between the image file, the map file and the rational data file is built by their names. The image file is a high density scan of the 2-D gel. The map file describes the location and the size of the spots as polygons. The rational data file is a document in Microsoft Access format that is connected to the WWW server by an Open Database Connectivity (ODBC) driver from MySQL. This connection ensures that after a single transfer of all data, no further maintenance and administration work is required. The rational data file is located on a micro-computer with IP address at any location of choice. The Hyper Text Markup Language (HTML) documents displayed via internet are dynamically generated on the basis of the available data for each individual session. Properties of proteins are presented in annotation spot windows. An example for such an annotation is: Spot ID: C191, Mr (2-DE): 27100, Mr (theoretical) 28160, pi (2-DE) 4.7, Identification Method PMF/PSD, Sequence coverage 35%, Protein name electron transfer flavoprotein beta sub-unit, short name fixA, Rv-No Rv3029c, EMBL: Z99263, NCBI: 2414529, Ident. No MLCB637, Gene No MLCB637.03. The EMBL and NCBI Nos have hyperlinks to obtain easily more information.

EXAMPLE 4

Analysis of the Mycobacterial Protein Composition by Detailed Proteome Analysis

Whole cell preparations of mycobacteria resulted in 2-DE patterns containing 1,500-2,000 distinct protein spots depending on silver-staining conditions and the amount of sample applied to the gels. Standard patterns of *M. bovis* BCG Chicago and *M. tuberculosis* H37Rv chosen for the construction of the mycobacterial 2-DE database are shown in FIGS. 1a and b. Molecular mass and isoelectric point calibrations were obtained by internal mycobacterial marker proteins identified during this approach. Some marker proteins for calibration are: Spot A540, tuf, Rv0685, pI 5.3, Mr 43594; Spot A543, acn, Rv1475c, pI 4.9, Mr 102500; Spot A10, tig, Rv2462c, pI 4.4, Mr 50616; Spot B5, probable fatty acid-acyl CoA reductase, Rv1543, pI 9.1, Mr 36821, Spot C342, nuoC, pI 5.4, Mr 26932; Spot E54, rplL, Rv0652, pI 4.6, Mr 13441; Spot F58, probable heat-shock protein, pI 6.8, Mr 10269. Both mycobacterial species comprise patterns with a high density of spots in the acidic range, whereas in the basic range, spot density is clearly reduced. The patterns of the 4 strains investigated are highly similar and can be compared easily. They were divided into 6 sectors to promote data handling for visual inspection and personal computer evaluation (FIG. 2).

Selected proteins from the 6 sectors were identified by peptide mass fingerprinting (Pappin, Curr. Biology 3 (1993), 327) using MALDI-MS. Selected proteins from the 6 sectors were identified by peptide mass fingerprinting using MALDI-MS. Starting with the procedure as described in Otto (*Electrophoresis* 17 (1996), 1643) sensitivity was improved during the course of identification of 270 protein species by minimization. Identification starting from 1 spot per protein species was successful. Gel spots were washed in 500 µl 100 mM Tris/HCl pH 8.5 in 50% acetonitrile for 20 min at 30° C. Further pH stabilization and reduction of the concentration of acetonitrile was obtained by a following equilibration in 500 µl 100 mM Tris/HCl pH 8.1 in 10% acetonitrile. The gel was now shrunken by evaporation in an Eppendorf concentrator 5301 (Eppendorf, Hamburg, Germany) to about 20% of the starting volume. Depending on the gel spot size 20 to 100 µl of a buffer containing 100 mM Tris/HCl pH 8.1, 1 mM $CaCl_2$ in 10% acetonitrile together with 0.5 pg trypsin/100 µl buffer were added. Trypsination was performed overnight at 37° C. Enzymatic digestion was stopped by 2% TFA solution. A minimized peptide collecting device, reducing the amount of reversed phase material (Octadecyl-functionalized silica gel, Aldrich, Steinheim, Germany) to about one fifth (Otto, (1996) loc. cit.) was used to wash and concentrate the sample. The salt-free bound peptides were then eluted from the column by 50 µl 60% acetonitrile in 0.1% TFA. A further improvement in sensitivity was obtained by the use of 50 mM ammoniumbicarbonat pH 7.8 in 10% acetonitrile as the digestion buffer, a volatile buffer allowing to omit the peptide collecting device and therefore reducing drastically surface contacts and therefore loss of the peptides. A protein was accepted as identified if peptides covering at least 30% of the complete sequence were detected. An assignment with a sequence coverage below 30% was only accepted, if (i) at least the 3 main peaks of the mass spectrum matched with a database sequence, (ii) the number of low intensity peaks was clearly reduced and the mass of the uncleaved protein fitted within 20%, or (iii) PSD confirmed a proposed protein. In particular, the method is characterized by the capability of analyzing whole pathogenic organisms (like mycobacteria) and/or fractions thereof due to the possibility of identification of differentially expressed protein(s)/protein species by peptide mass fingerprinting without confirmation by a further method. Most proteins matched with 1 database entry with a clearly higher number of common peptides as compared to the second candidate. Only 3 spots in BCG contained 2 proteins: BCG Chicago spot C100 includes a protein homologous to a conserved hypothetical *M. tuberculosis* H37Rv protein, Rv3075c, and, in addition, the transcription antitermination protein NusG, Rv0639. BCG Chicago C241 contains a probable adenylate kinase, Rv0733, and a probable transposase, Rv1041c; and C600a thioredoxin reductase, Rv3913, and 3-hydroxyacyl-CoA dehydrogenase, Rv0468. In some cases peptides of neighboring spots were detected in reduced intensity in addition to the peptides of the main protein.

Starting from Coomassie Brilliant Blue R-250 or G-250 or in some cases negatively stained gels, 312 mycobacterial protein spots were analyzed. From these spots peptide mass fingerprinting identified 263 proteins. Starting with the identification of *M. bovis* BCG strain Chicago CP, 157 proteins were identified. From *M. tuberculosis* strains H37Rv and Erdman 53 and 12 proteins were identified by PMF (peptide mass fingerprinting), respectively. Additional sequence information confirmed the PMF assignments for 34 proteins. Because all PSD results confirmed the PMF assignments, it could be shown that 30% sequence coverage is sufficient for protein identification. PSD had to be used only if the sequence coverage was <30%. As determined by PMF, all 23 H37Rv spots had the same identity as their counterparts at the same position in the BCG pattern. Proteins were identified by comparison of the spot position of these two mycobacterial species. This resulted in a total of 162 identified proteins in BCG Chicago and a total of 626 identified proteins in CP of all strains.

Identified proteins of the mycobacterial species investigated were classified according to the *M. tuberculosis* H37Rv gene classification of Cole (1998; loc. cit.) and assigned to the corresponding Rv-numbers (Tab. 1). After identification of about 3% of all predicted gene products, starting with the most common proteins, species of many categories were found. However, only within two categories, i.e. protein translation/modification and chaperones/heat shock, more than 40% of the predicted gene products were identified in the obtained 2-DE patterns. To date expression of 30 conserved hypotheticals and 6 unknowns, not described previously at the protein level, was revealed.

Figure 1C:
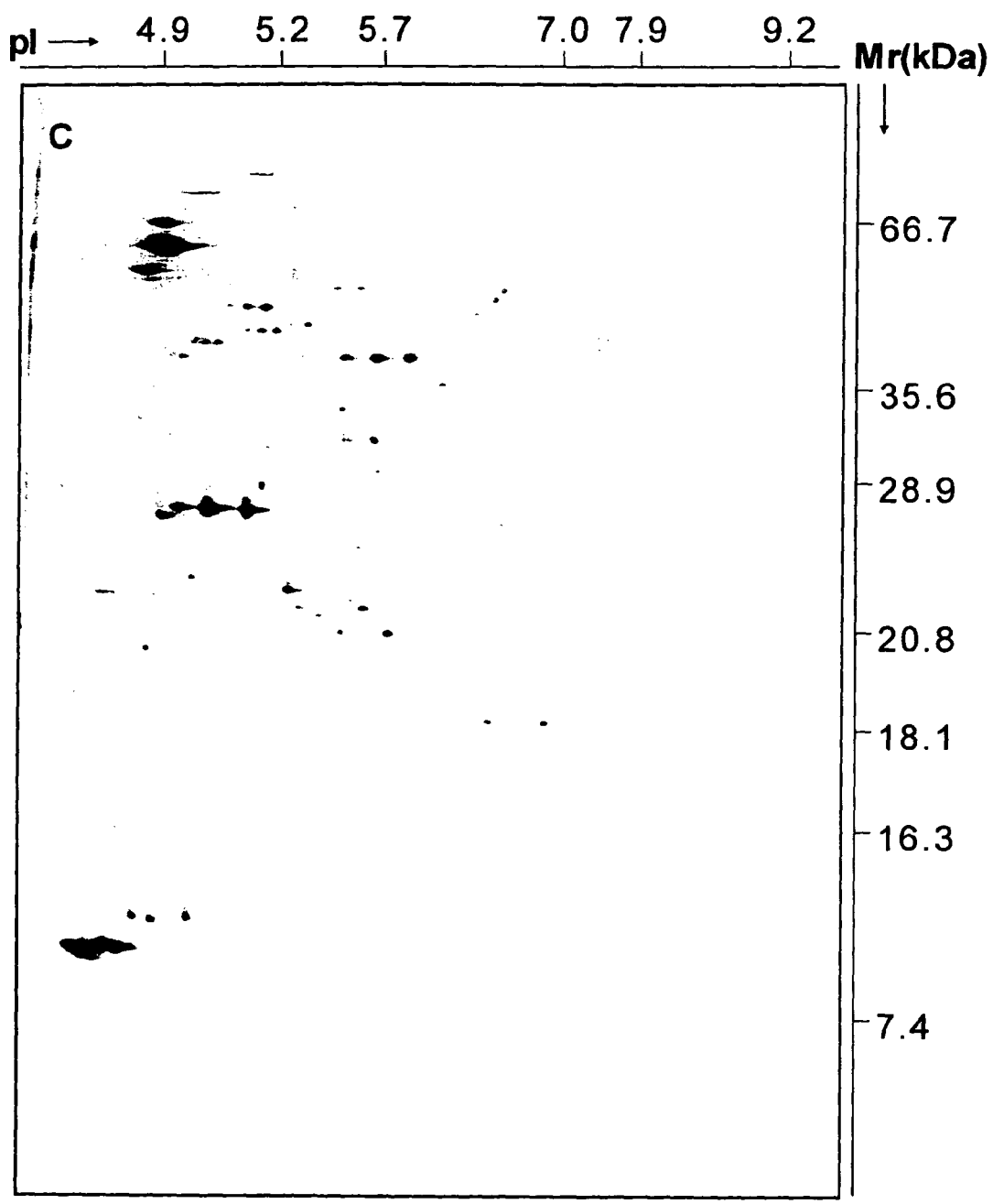
Figure 2A:
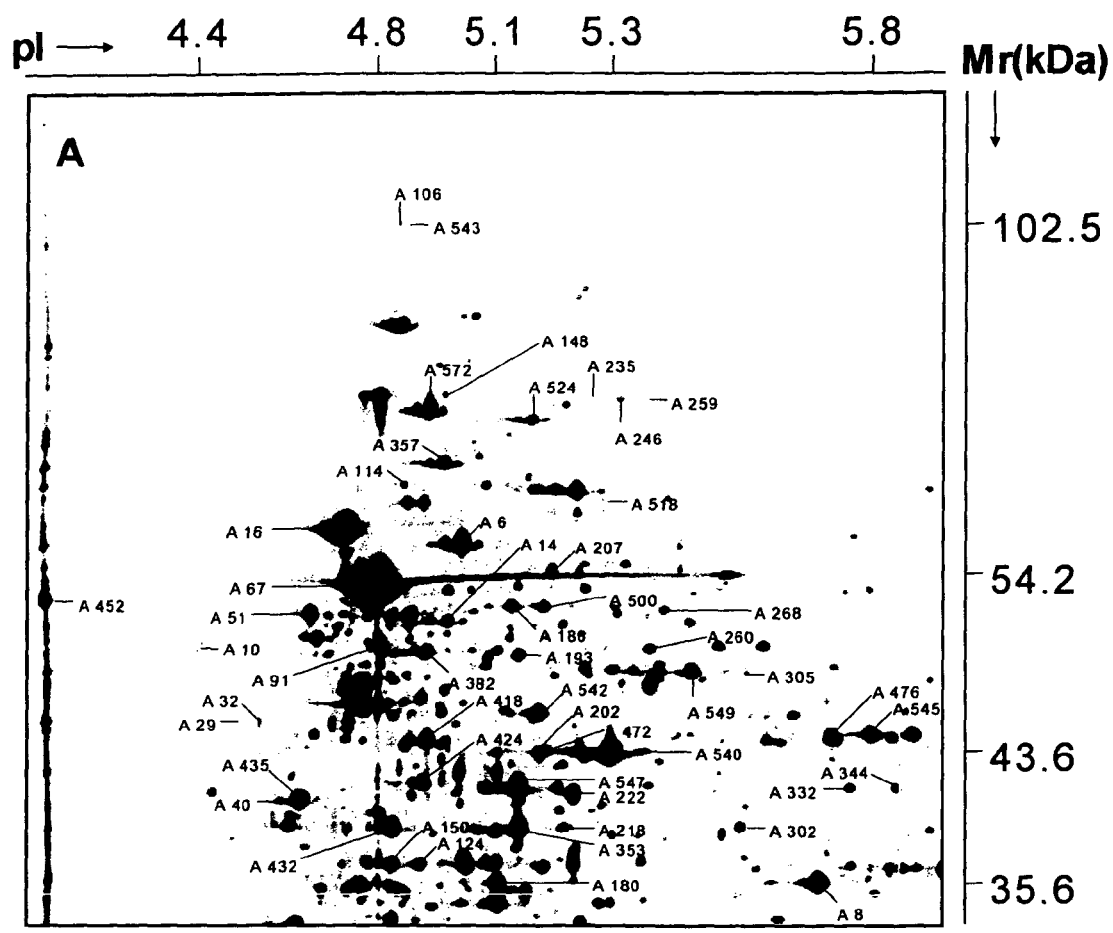
Figure 2B:
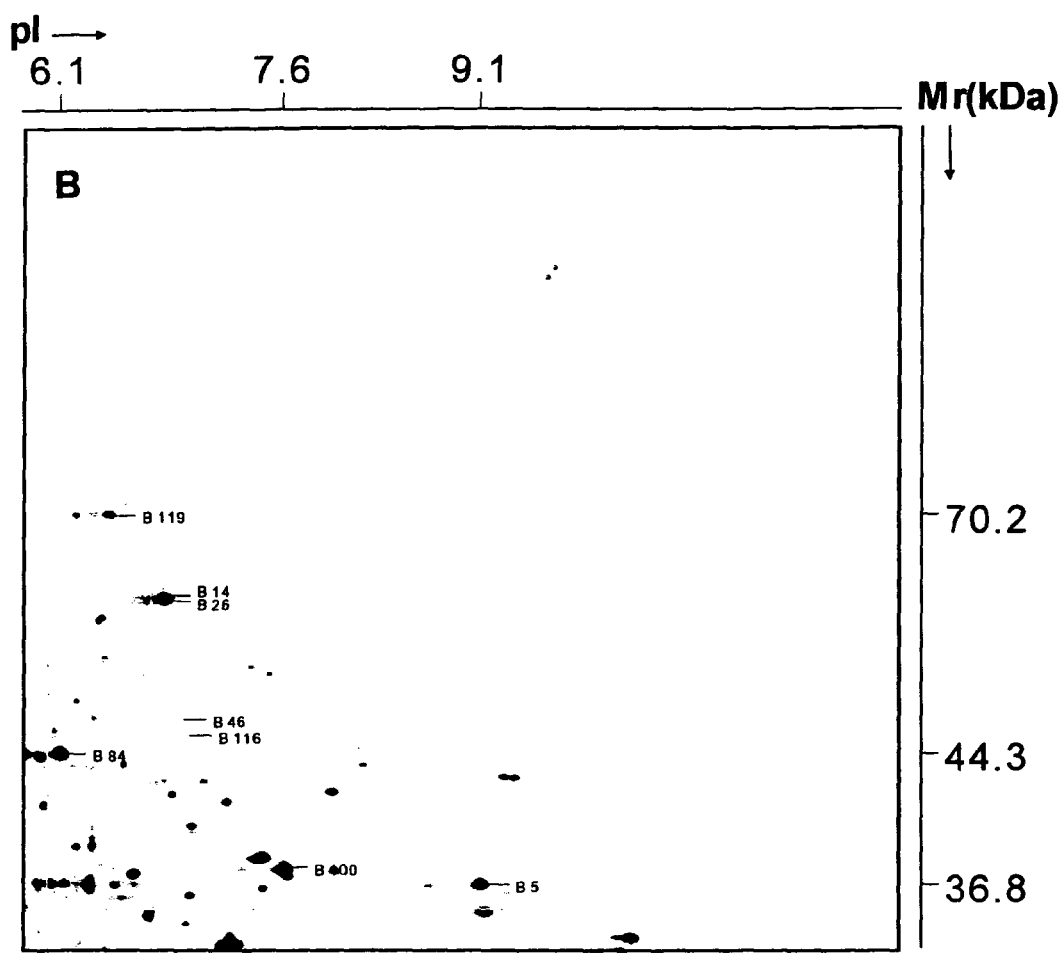
Figure 2C:
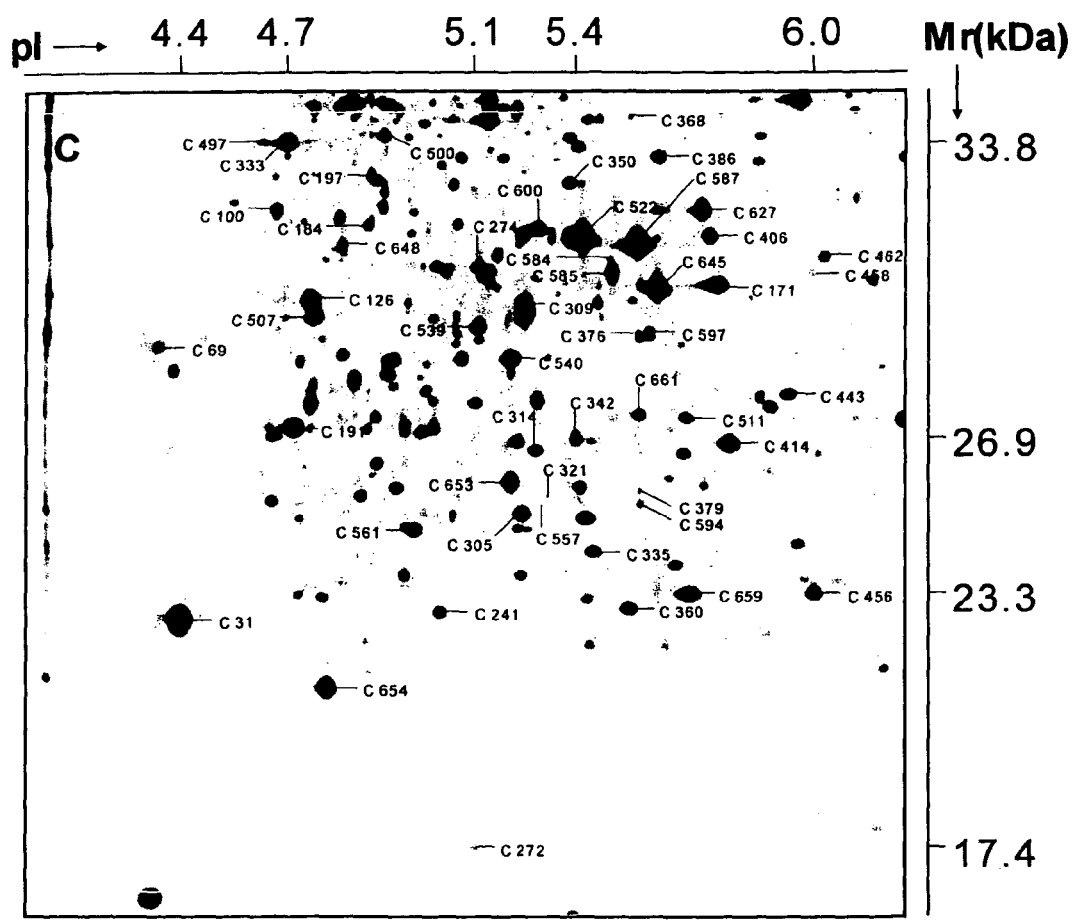
Figure 2D:
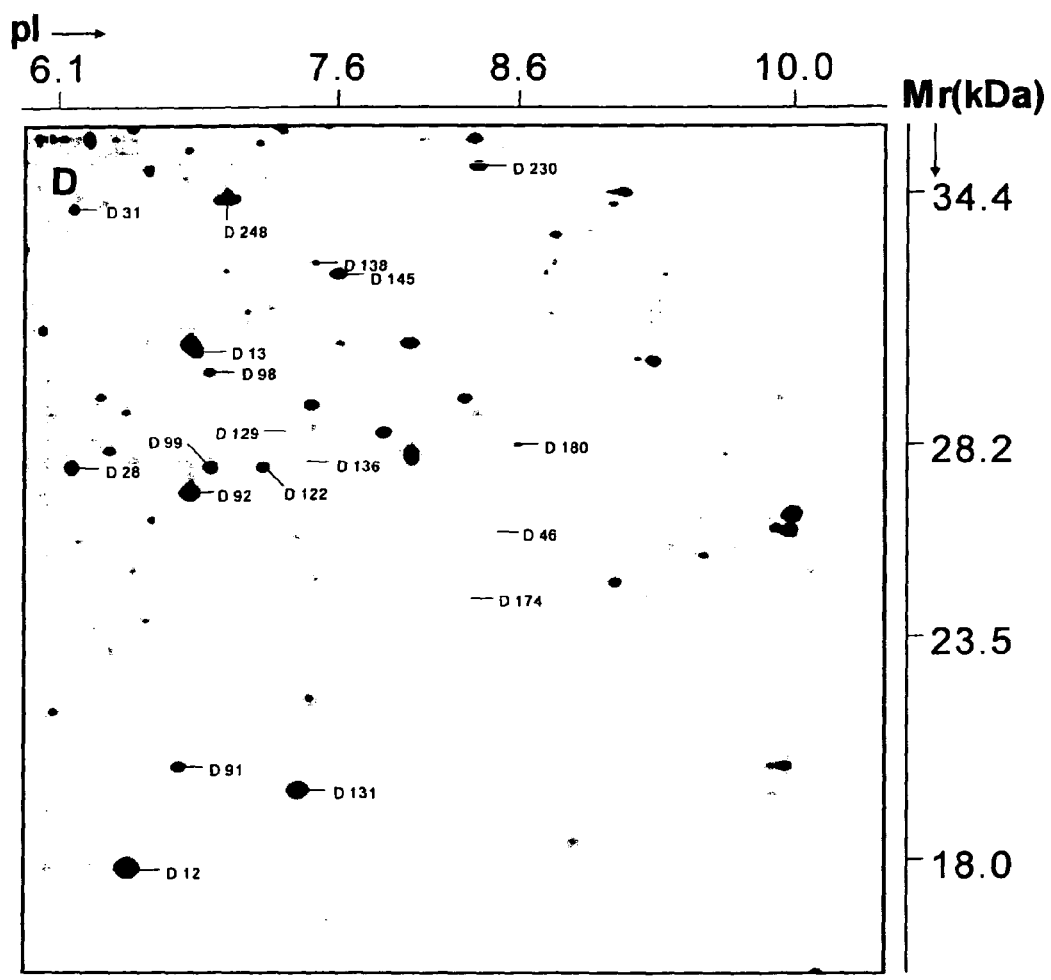
Figure 2E:
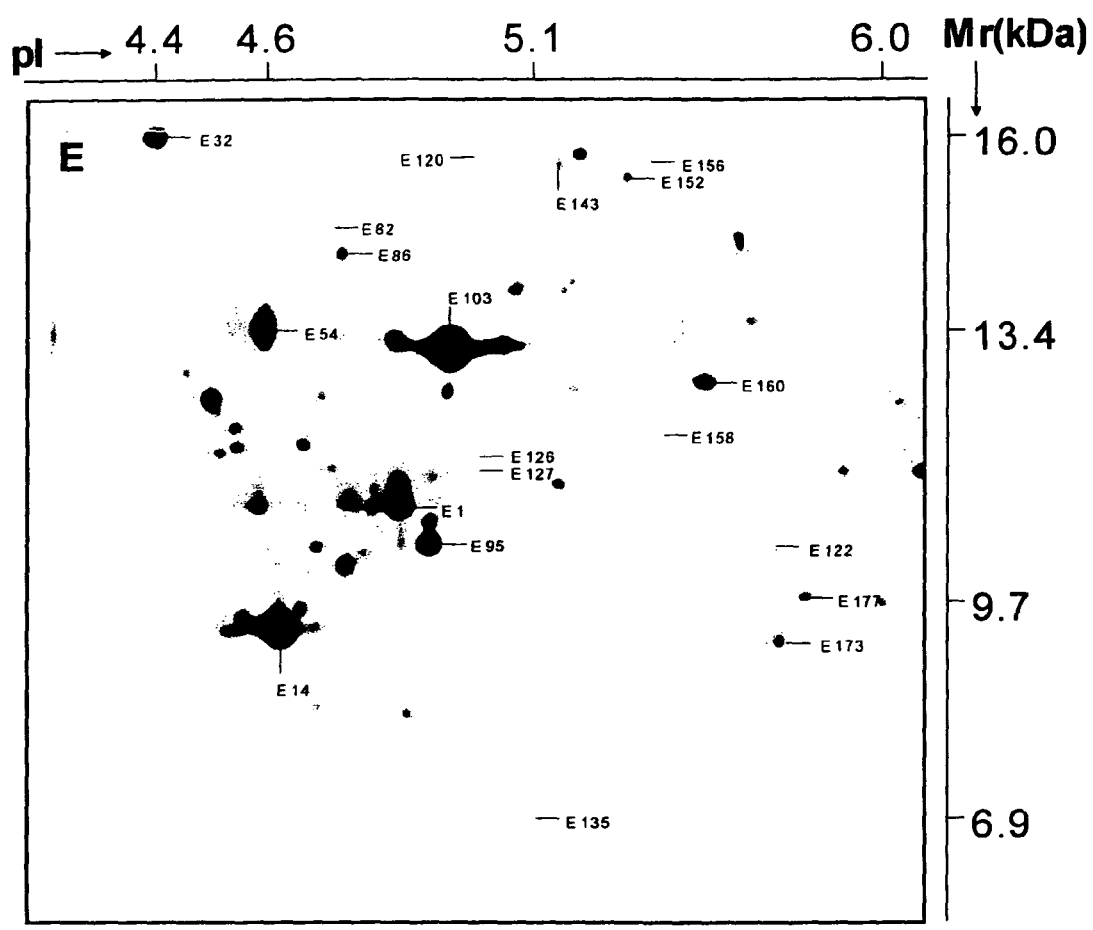
Figure 2F:
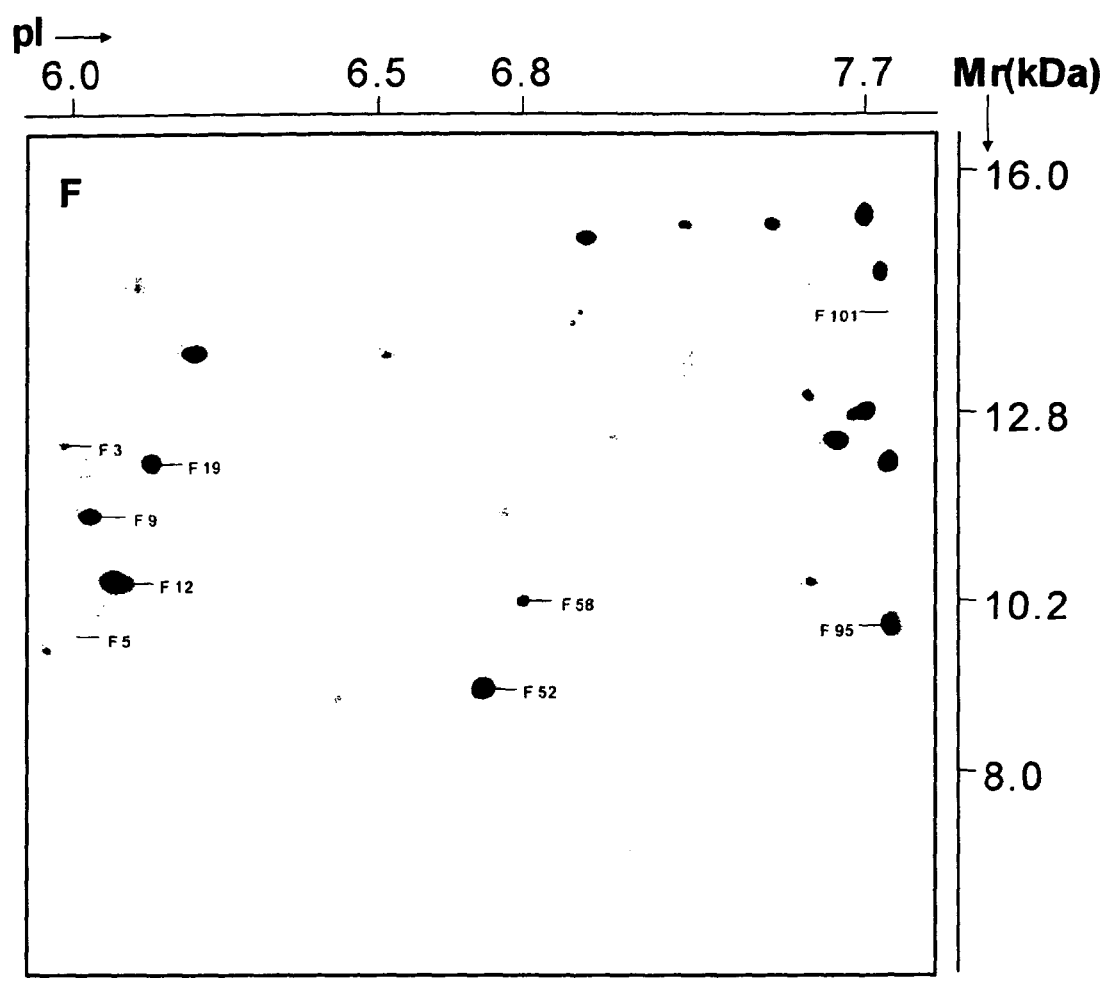
Figure 3A:
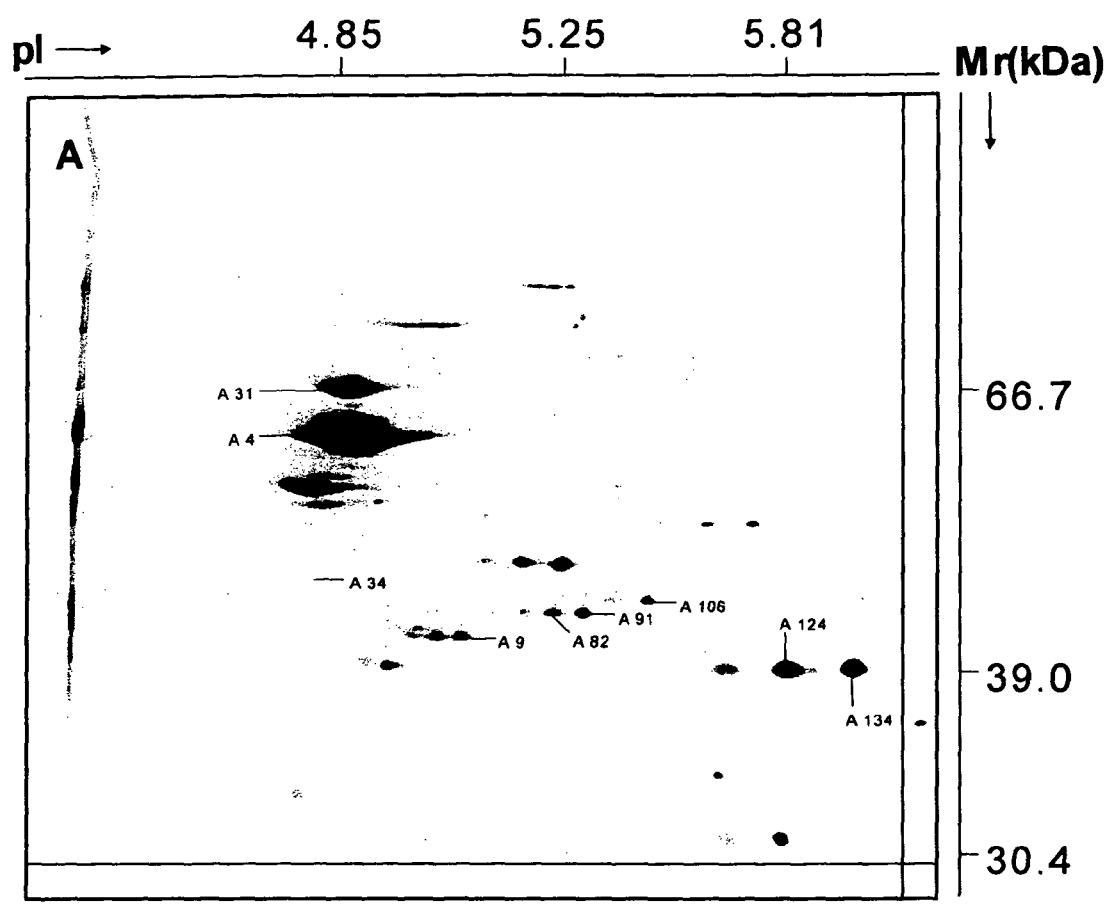
Figure 3B:
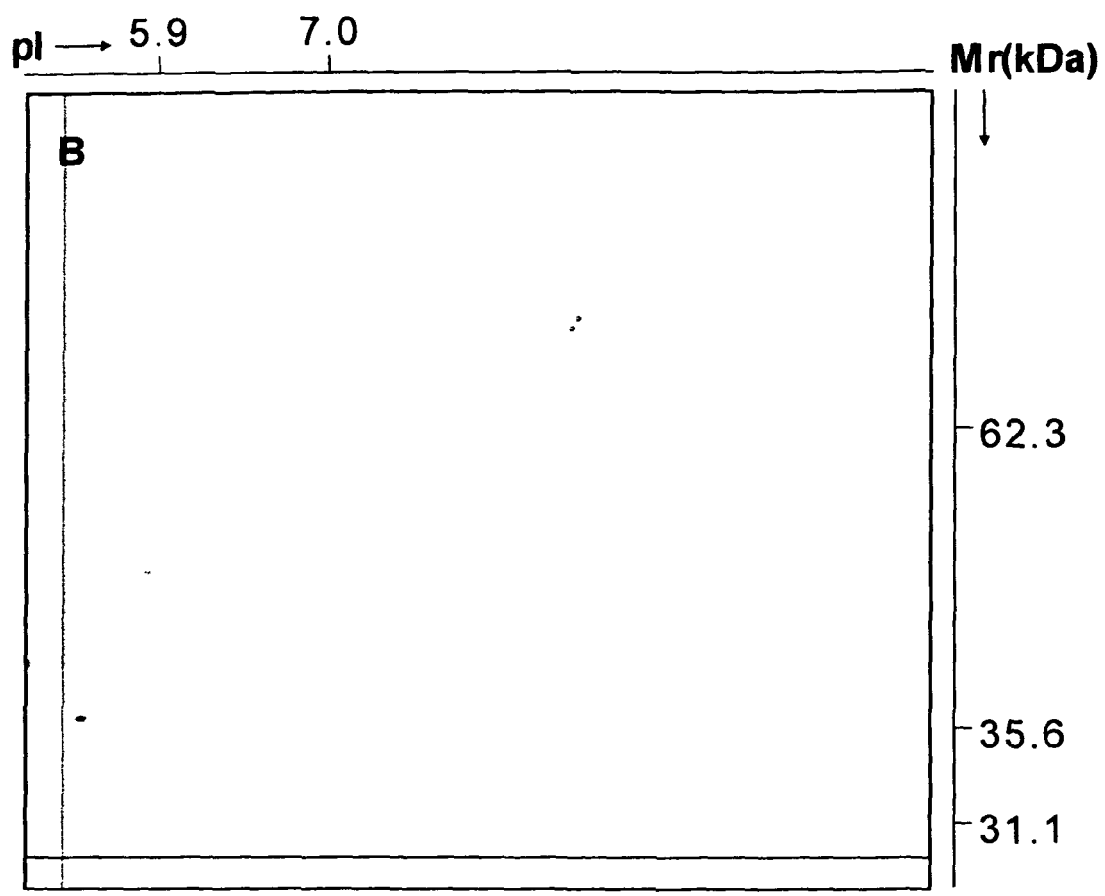
Figure 3C:
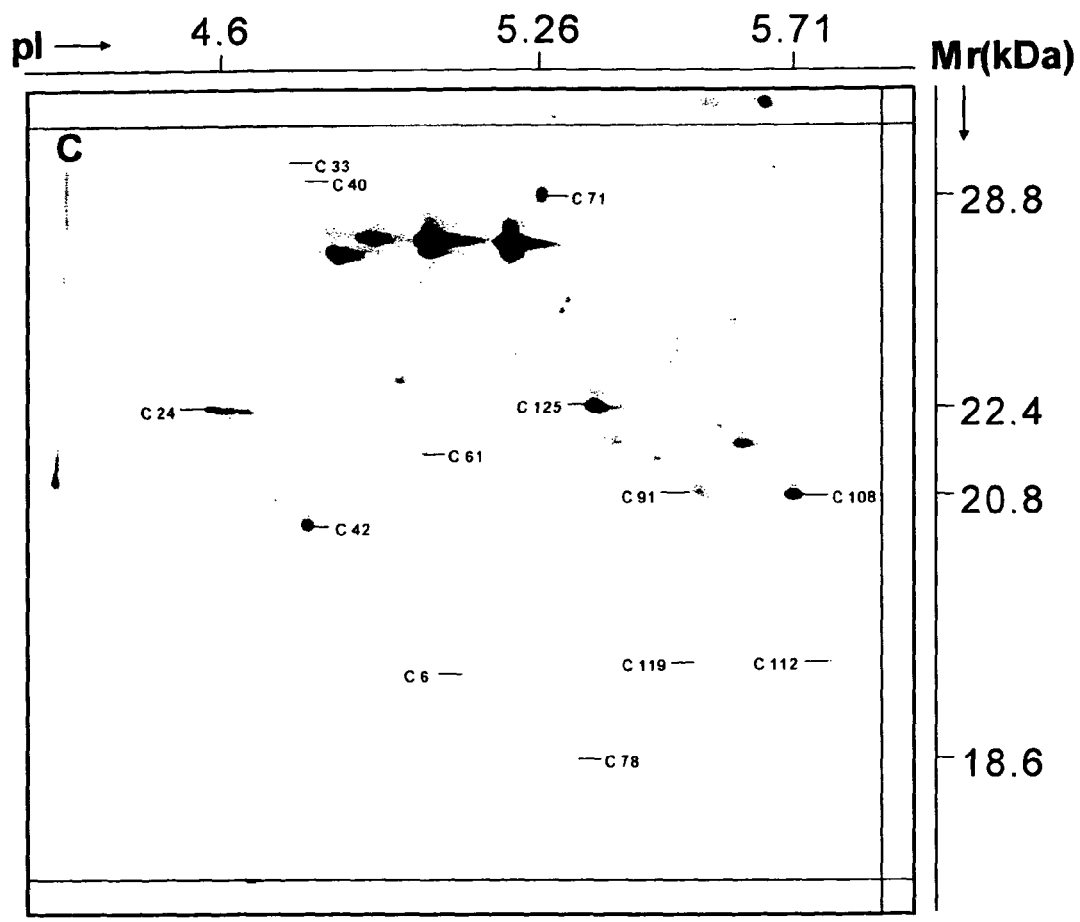
Figure 3D:
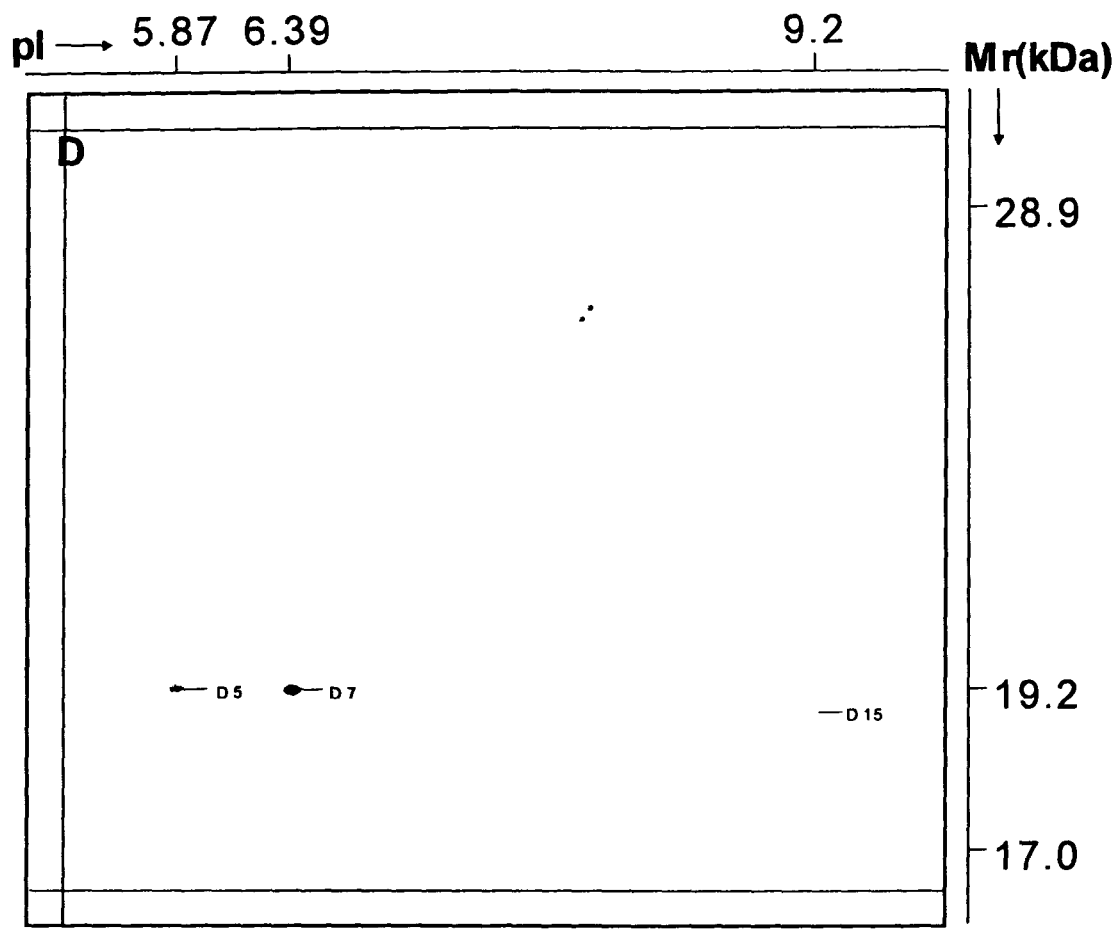
Figure 3E:
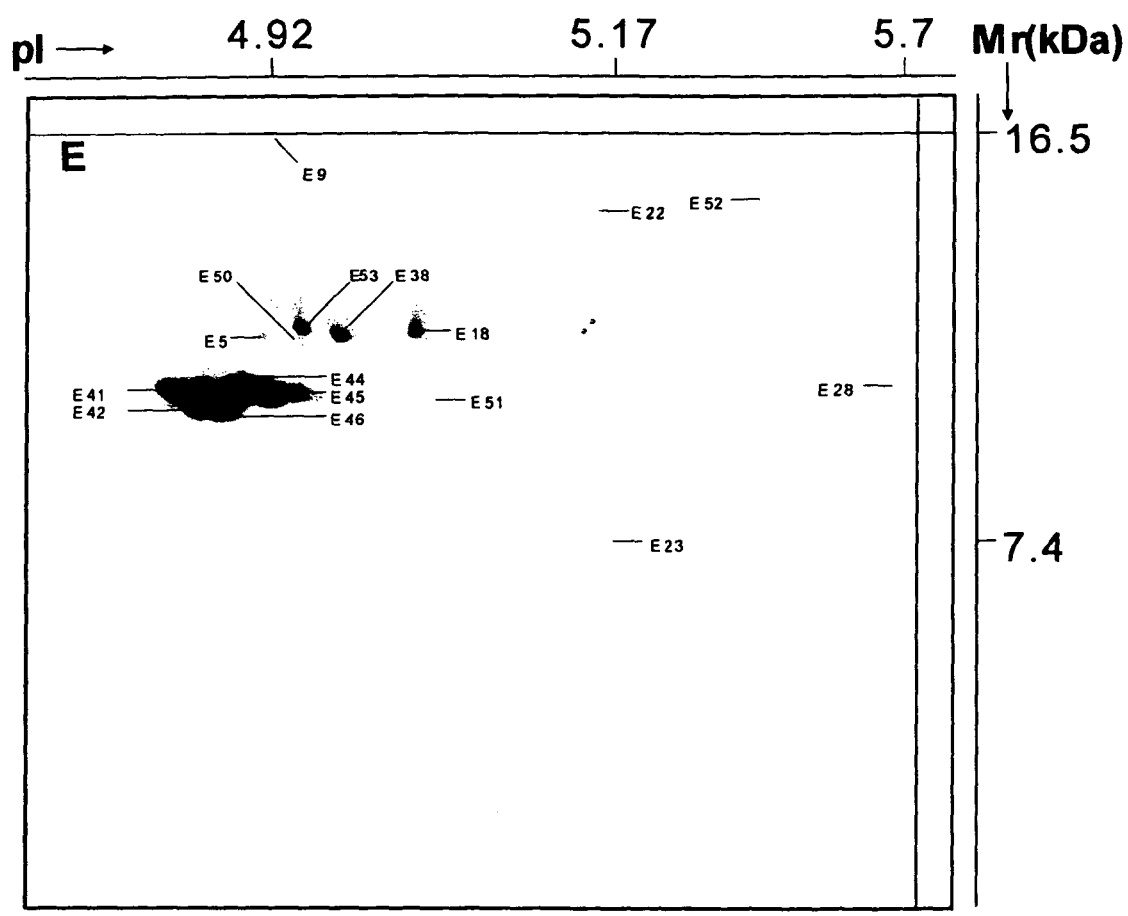
Figure 3F:
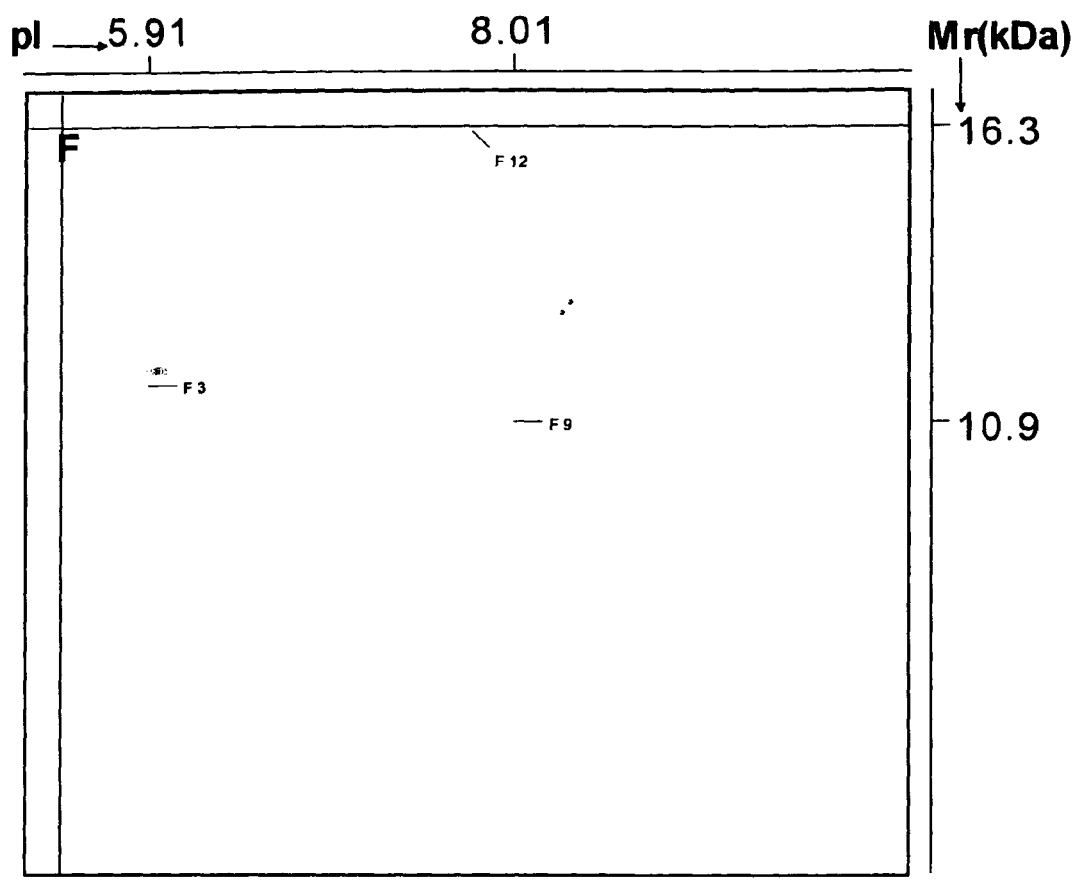

In the CSN of *M. tuberculosis* H37Rv approximately 300 proteins were resolved by 2-DE (FIGS. 1c and 3). So far, 53 protein spots were identified within the CSN of *M. tuberculosis* H37Rv (Table 1). Similar to the CP patterns, CSN patterns were highly comparable. As compared with CP, CSN proteins occurred relative to the total number of spots in more spot series (FIG. 1c). Of the 164 identified proteins in CP, 20 gene products and of 53 from CSN 12 appeared as more than 1 spot in the 2-DE patterns, suggesting their existence as different protein species, probably due to posttranslational modification, such as phosphorylation, glycosylation or acylation. The higher portion of spot series in CSN could be additionally caused by the higher load per protein on the gel, by a higher degree of posttranslational modifications of secreted proteins, or by degradation of proteins outside of the bacterial cell. For instance, in CSN three adjacent series containing 8 spots were stained. Four of these spots were identified by PMF as elongation factor Tu (tuf), Rv0685. The 14 kDa antigen (Rv2031c) and the 10 kDa chaperonin (Rv3418c) appeared as 6 and 5 spots, respectively. An example from CP, steroid dehydrogenase of BCG Chicago corresponding to Rv0148, occurred in 6 spots randomly distributed within one sector of the 2-DE pattern.

EXAMPLE 5

Figure 4A:
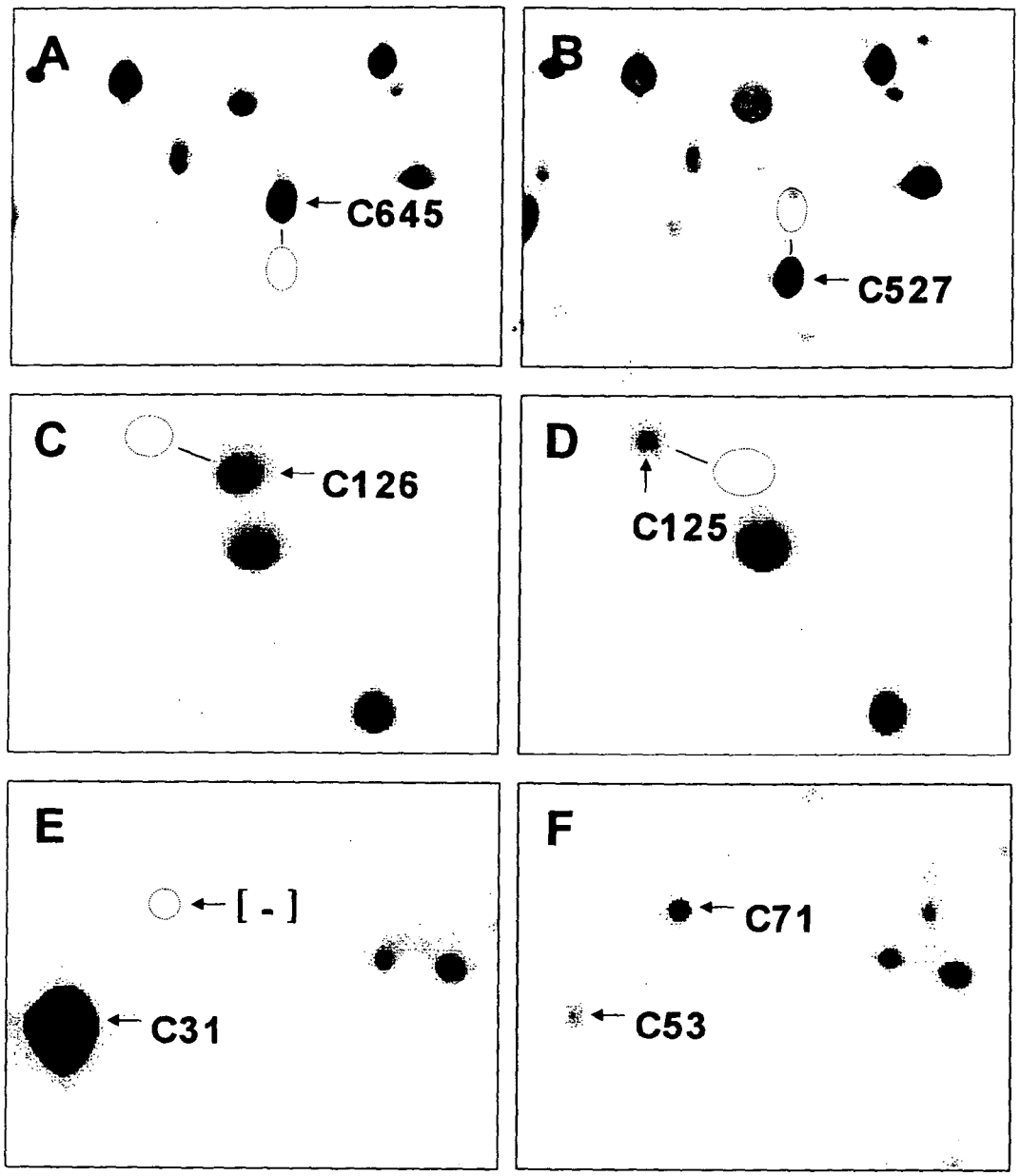

Comparison of Protein Patterns from Different M. Tuberculosis and M. bovis BCG Strains The genomes of the M. tuberculosis complex, comprising all 4 strains investigated, are highly conserved (Sreevatsan (1997), Proc. Natl. Acad. Sci. U.S.A. 94: 9869). The 2-DE patterns confirm the prediction that the vast majority of proteins have their counterparts in all strains investigated. However, clear differences in spot intensity, presence or absence, and position of the spots between these strains could be detected. Evaluation was concentrated on readily detectable spot variations, which were consistent in all obtained 2-DE patterns. The investigation was primarily aimed at the elucidation of proteins occurring exclusively in the virulent strains to detect potential virulence factors and candidate vaccine antigens (Table 2). Between BCG Chicago and H37Rv, 31 variants were detected. In comparison to BCG, H37Rv comprised 13 additional spots and lacked 8 spots; 9 spots were decreased in intensity and 1 spot was increased. Table 3 illustrates protein species which were either decreased or increased (1 spot) in intensity and denotes "intensity differences" between BCG Chicago and M. tuberculosis H37Rv. From the 31 variants, 25 were identified by PMF. Six identified proteins in H37Rv were without any counterpart in BCG: L-alanine dehydrogenase (40 kDa antigen, Rv 2780), isopropyl malate synthase (Rv 3710), nicotinate-nucleotide pyrophosphatase (Rv1596), MPT64 (Rv1980c), and 2 conserved hypotheticals (Rv2449c and Rv0036c). The absence of L-alanine dehydrogenase in BCG confirms a previous observation (Andersen (1992), Infect. Immun. 60: 2317) and shows that differentially expressed proteins can be detected by the methods described in the examples described herein. Eight of the +/−variants were shown to be mobility variants, possibly caused by amino acid exchanges or posttranslational modifications. Two obvious positional variations, 1 intensity and 1+/−variant are shown in FIG. 4a. Succinyl-CoA synthase alpha chain (Rv0952) shifted from a higher Mr variant in BCG to a lower one in H37Rv. An oxidoreductase of the aldo/keto reductase family (Rv2971) was shifted diagonally from a more basic, lower Mr form in BCG to a more acidic, higher Mr, form in H37Rv. Alkyl hydroxyperoxide reductase chain C(Rv2428) was decreased in H37Rv, and MPT64 (Rv1980c) occurred as an additional spot in H37Rv.

Comparison between M. tuberculosis Erdman and M. bovis BCG Chicago revealed 4 mobility variants, belonging to an oxidoreductase of the aldo/ketoreductase family described as Rv2971 in H37Rv, succinyl-CoA synthase α chain (Rv0952), S-adenosylmethionine synthase (Rv1392), and oxireductase (Rv0068).

Positional variants are interesting vaccine candidates, too, if the positional variation is caused by amino acid exchanges within the amino acid sequence relevant to T-cell recognition. Furthermore, if this is not the case, enzymes mediating a posttranslational modification are of interest for vaccine development or for diagnostic purposes.

Figure 4B:
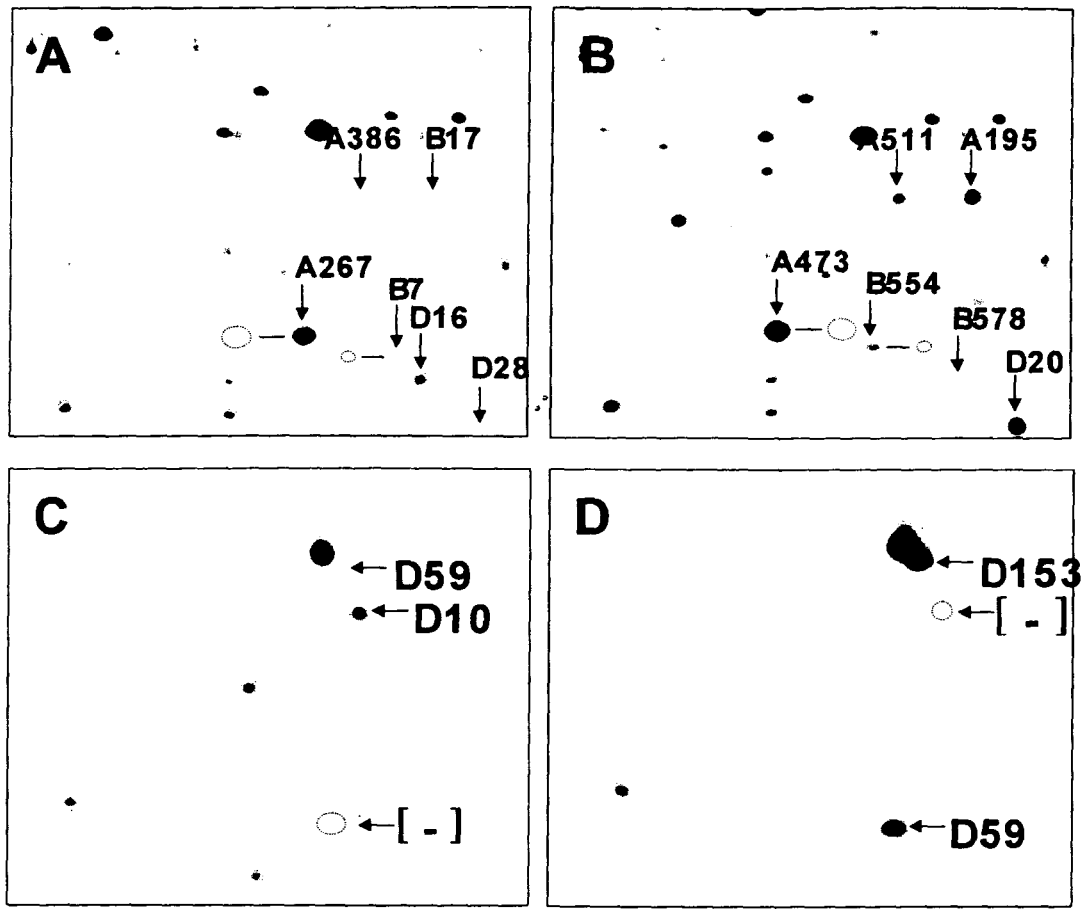

Comparison of 2-DE patterns from M. tuberculosis H37Rv versus Erdman revealed 18 variant proteins, 16 of which were identified. In the M. tuberculosis Erdman proteome 6 protein species appeared to be increased in intensity; 2 protein species newly appeared; 6 were absent; and two represented mobility variants. Some examples are shown in FIG. 4b. Two spots of the acetylornithine aminotransferase ArgD (Rv1655) were present both in H37Rv and in Erdman, but both with clearly higher intensities in Erdman. The transcriptional regulator MoxR(Rv1479) was shifted to a more acidic position in the Erdman 2-DE pattern. The haloalkane dehalogenase (Rv2296), 2 spots containing L-alanine dehydrogenase (Rv2780), and protease IV (Rv0724) were absent from the Erdman proteome, whereas the unknown protein Rv3213c, sharing similarity with a Soj protein of possible relevance to chromosome segregation, and the conserved hypothetical protein Rv2641 were absent in the H37Rv proteome.

BCG Chicago and Copenhagen expressed highly similar 2-DE patterns. Only 3 obvious variants were identified. The conserved hypothetical protein Rv0968 was absent in the Copenhagen proteome, and 2 spots of a probable neuraminidase (Rv3463) were increased in intensity in the Chicago strain.

EXAMPLE 6

Classification of Identified Proteins

Of the 263 proteins identified by 2-DE in total CP and CSN of both M. tuberculosis H37Rv/Erdman and M. bovis BCG, about one third corresponded to housekeeping proteins involved in gene regulation, biosynthesis, degradation or metabolism. Amongst housekeeping proteins involved in transcription/translation, 4 polypeptides play a role in transcription control such as the RNA polymerase A (Rv3457c) and the transcription termination protein rho (Rv1297). Four proteins are ribosomal proteins such as the 50S L7/L12 (Rv0652), and 7 proteins are involved in protein translation and modification such as the elongation factors Tu (Rv0685) and Ts (Rv2889c) and the homolog to the transcription elongation factor greA of M. leprae (Rv1080). The EF-Tu was present in the CP as well as the CSN. This factor has been localized to the cell wall of M. leprae and is associated with the membrane and periplasmic space of other bacteria such as E. coli and Neisseria gonorrhoeae but its function remains uncertain (Marques (1998), Infect. Immun. 66: 2625; Jacobson (1976), Nature 261: 23; Porcella (1987), Microbiol. 142: 2481).

There are 2 two-component response regulators (Rv1626, Rv3133c) present in the proteome. One of these proteins, Rv1626, shows strong similarities to two-component systems of Methanobacterium thermoautotrophicum, Azetobacter vinelandii and Streptomyces coelicolor indicating the usage of environmental sensor and regulation systems by mycobacteria similar to other prokaryotes (Smith (1997), J. Bacteriol. 179: 7135; Gutierrez (1995), Mol. Microbiol. 18: 579; Brian (1996), J. Bacteriol. 178: 3221). In A. vinelandii, this protein is involved in negative regulation of the nitrite-nitrate reductase system. In S. coelicolor, a member of the Actinomycetaceae closely related to Mycobacteriaceae, it is a negative regulatory element in the synthesis of antibiotics. MoxR (Rv1479), which was apparently modified in H37Rv when compared to Erdman is a putative regulatory molecule probably involved in the formation of an active methanol dehydrogenase as shown for *Paracoccus denitrificans* (Van Spanning (1991), *J. Bacteriol.* 173: 6948). Similarly, the 40 kDa antigen (Rv2780), an alanine dehydrogenase, which is unique for *M. tuberculosis* and *M. marinum* (Andersen (1992), *Infect. Immun.* 60: 2317), was upregulated in H37Rv when compared to Erdman. It is unclear yet, whether this polypeptide is exclusively expressed in virulent mycobacteria. However, it could contribute to virulence because it has been implicated as part of the cell wall synthesis machinery since L-alanine is an important constituent of the peptidoglycan layer. Consistent with this notion, this protein is also present in the mycobacterial cell wall and even the outer-most capsule (Ortalo-Magne (1995), *Microbiol.* 141: 1609).

Twenty-five protein spots were identified as putative heat shock proteins including Hsp60 (groEL2; Rv0440), Hsp70 (dnaK; Rv0350), Hsp10 (groES; Rv3418), and ClpB (38; Rv0384c). Due to the high sequence homology between mycobacterial and human Hsp60 it has been suggested that this protein is involved in infection triggered autoimmune responses. DNA vaccination experiments also indicate that Hsp60 is a potential vaccine candidate (Tascon (1996), *Nature Med.* 888). A 14 kDa protein (hspX; Rv2031c) related to the heat shock protein alpha-crystalline, is a strong inducer of antibodies in patients with pulmonary tuberculosis (Verbon (1992), *J. Bacteriol.* 174: 1352). Interestingly, both *M. bovis* BCG and *M. tuberculosis* contain a putative rotamase (peptidyl-prolyl cis trans isomerase; Rv0009) homologous to cyclophilins, the specific receptors for the immunosuppressive drug cyclosporin A.

A number of proteins identified within the mycobacterial proteome are involved in biosynthesis/degradation of fatty acids and glycolipids which are essential components of the complex acid fast cell wall. Examples are the methoxy mycolic acid synthase 4 (Rv0642c), and the three molecular targets for the commonly used drugs against tuberculosis, isoniazid and ethambutol: The enoyl (ACP) reductase (Rv1484) and β-ketoacyl (ACP) synthase (Rv2246) are central to the biosynthesis of mycolic acids, and have recently been identified as targets for isoniazid (Mdluli (1998), *Science* 280: 1607; Rozwarski (1998), *Science* 279: 98; Sacchettini (1996), *Res. Microbiol.* 147: 36). The target for ethambutol, arabinosyl transferase (Rv0020c), participates in arabinogalactan synthesis and is specific for acid fast bacteria including mycobacteria (Lety (1997), *Antimicrob. Agents Chemother.* 41: 2629). Members of the antigen 85 complex (Rv1886c, Rv3803c, Rv3804c) are also part of the enzymatic cascade of the cell wall synthesis, i.e. mycolyl transferases, but apparently have also the potential to mediate mycobacterial binding to fibronectin (Belisle (1997), *Science* 276: 1420; Abou-Zeid (1988), *Infect. Immun.* 56: 3046). In addition, they are considered as vaccine candidates (Kaufmann and Andersen (1998), in "Chemical Immunology: Immunology of Intracellular Parasitism" (Ed. F. Y. Liew): 21-59).

Amongst the proteins identified within the mycobacterial proteome, several have been suggested as mycobacterial antigens of putative value for vaccine development and/or for diagnosis: These include the alanine dehydrogenase (Rv2780), Hsp60 (Rv0440), Hsp70 (Rv0350), members of the antigen 85 complex (Rv1886c, Rv3803c, Rv3804c), α crystalline (Rv2031) and the 35 kDa antigen (Rv2744c) (Kaufmann and Andersen (1998) loc. cit.; O'Connor (1990), *Res. Microbiol.* 141, 407). The mycobacteria specific 34 kDa protein, termed antigen 84 (Rv2145c), has been identified in *M. kansasii*, *M. bovis* BCG, *M. leprae* and *M. tuberculosis* and is recognized by antibodies in 60% of lepromatous leprosy patients (Hermans (1995), *Infect. Immun.* 63: 954). MPT64 (Rv1980c) and MPT51 (Rv3803c), a homolog to Antigen 85, are both CSN proteins and MPT64 is a known inducer of delayed type hypersensitivity responses in guinea pigs (Kaufmann and Andersen (1998) loc. cit.).

Although the acid fast cell wall and its enzymatic machinery contribute to mycobacterial survival in the host and resistance to host defense mechanisms, other factors must contribute to virulence of *M. tuberculosis* although they are far from being elucidated. As yet, only 5 potential virulence genes have been described: Catalase-peroxidase and superoxide dismutase which protect against reactive oxygen intermediates (ROI); noxR1 which confers resistance against reactive nitrogen intermediates (RNI); mce and sigA which encode macrophage-colonizing factor and sigma factor, respectively (Collins (1996), *Trends Microbiol.* 4: 426; Ehrt (1997), *J. Exp. Med.* 186: 1885; Arruda (1993), *Science* 261: 1454). In addition, the *M. tuberculosis* genome contains a homolog of smpB, a gene of *Salmonella typhimurium* involved in intracellular survival (Cole (1998) loc. cit.). Interestingly, none of these proteins were identified in this analysis. Furthermore, the genome sequence revealed several genes for lipases, phospholipases C, esterases and proteases potentially contributing to mycobacterial virulence (Cole (1998) loc. cit.). So far, only two alkyl hydroperoxide reductases (ahpC Rv2428, ahpD Rv2429) have been identified within the proteome.

Pathogenic mycobacteria survive intraphagosomally in host macrophages and interfere with phagosome maturation through mechanisms virtually unknown thus far (Russell (1997), *Philos. Trans. R. Soc. Lond. B. Biol. Sci.* 352: 1303). The HspX (α-crystalline; Rv2031c) has recently been shown to be important for intracellular survival of mycobacteria in macrophages (Harth (1994), *Proc. Nat. Acad. Sci. U.S.A.* 91: 9342; Clemens (1995), *J. Bacteriol.* 177: 5644). The urease and glutamine synthase of *M. tuberculosis* have been suggested to buffer the intraphagosomal pH and therefore block fusion with lysosomes (Sturgill-Koszycki (1996), *EMBO J.* 15: 6960; Schaible (1998), *J. Immunol.* 160: 1290). The mycobacterial phagosome represents an early endosomal compartment which intersects with the iron transport pathway (Dussurget (1998), *Trends Microbiol.* 6: 354; Gobin (1995), *Proc. Nat. Acad. Sci. U.S.A.* 92: 5189). There, proteins with high iron binding affinity such as exochelins, mycobactins and ferritin-like proteins (bfrA, bfrB) compete with the host cell iron handling system (Cole (1998) loc. cit.; Dussurget (1998) loc. cit.). Under conditions where iron is limited, these proteins have been detected by 2-DE (Dussurget (1998) loc. cit.).

In summary, of all proteins analyzed 39 polypeptides are conserved hypothetical proteins and 6 are unknown proteins using the information contained in the *M. tuberculosis* genome sequence. Furthermore, six identified proteins were detected in *M. tuberculosis* H37Rv, but could not be identified in *M. bovis* BCG. These proteins comprise: L-alanine dehydrogenase (40 kDa antigen, Rv 2780), isopropyl malate synthase (Rv 3710), nicotinate-nucleotide pyrophosphatase (Rv1596), MPT64 (Rv1980c), and 2 conserved hypotheticals (Rv2449c and Rv0036c).

EXAMPLE 7

Proteome Analysis Identifies Known Differences in Virulent and Avirulent Strains As described herein above (see Example 5) two proteins could be identified which are expressed in *M. tuberculosis* H37Rv, but not in *M. bovis* BCG: L-alanine dehydrogenase (40 kDa antigen; Rv 2780) and MPT64 (Rv 1980c). The absence of alanine dehydrogenase in BCG has been described earlier (Andersen et al. Infect. Immun. 60, 2317 (1992)) and was confirmed by this approach. MPT64 (Rv1980c) is a CSN protein and is a known inducer of delayed type hypersensitivity responses in guinea pigs (S. H. K. Kaufmann and P. Andersen, in "Chemical Immunology: Immunology of Intracellular Parasitism" (Ed. F. Y. Liew), 1998: 21-59.). This protein was absent in the 2-DE patterns of BCG. This example illustrates the potential of the here described method for proteome analysis on strains of pathogenic organisms.

Furthermore, the example shows that differentially expressed proteins can be identified by this method.

EXAMPLE 8

Further Comparisons of Protein Patterns from Different *M. tuberculosis* and *M. bovis* BCG Strains The 2-DE patterns of all four strains investigated (H37Rv, Erdman, Chicago and Copenhagen) are very conservative. The evaluation of 2-DE patterns comparing four strains of microorganism is difficult and time-consuming. In a second approach, therefore, the further analysis concentrated on +/− differences between the virulent strains as compared with the non-virulent strains. This investigation confirmed the results described in the examples described herein above. However, additional proteins Rv1511 (RD6), Rv1980c (RD2), Rv0222 (RD4), Rv1512 (RD6), Rv1978 (RD2), Rv2658c (RD13), Rv3875 (RD1), and Rv2074 (RD12) were found to be differentially expressed, confirming results from a comparison of the genome of *M. tuberculosis* with *M. bovis* by DNA Microarray (Science 284 (1999), 1520), where the loss of 16 regions (RD) in *M. bovis* BCG as compared to *M. tuberculosis* was described. Additionally, proteins occurring only in *M. tuberculosis* H37Rv and *M. tuberculosis* Erdman, but absent in *Mycobacterium bovis* BCG Chicago and *Mycobacterium bovis* BCG Copenhagen could be defined. These proteins COULD not be predicted by genomic investigations and comprised elongation factor G (Rv0120c), uridylate kinase (Rv2883c), ABC-type transporter (Rv1463), short chain dehydrogenase/reductase family protein (Rv 1856c), 1,3,4,6-tetrachloro-1,4,-cyclohexadiene hydrolase (Rv2579), phosphoribosylaminoimidazole carboxylase catalytic subunit (Rv3275c), hypothetical protein (Rv2557), and hypothetical protein (Rv3407). The sectors where these proteins occur in the virulent strains are shown in FIG. 5. The assignment of these protein species to their spot numbers and the link to the NCBI sequence database (www.ncbi.nlm.nih.gov/) by their accession No. are shown in Table 4.

Table 1: Proteins identified in 2-DE patterns of mycobacterial species. Proteins of *M. tuberculosis* H37Rv (H37Rv), Erdman (Erdman) and *M. bovis* BCG Chicago (Chic) and Copenhagen (Cop) were separated by 2-DE. The most intensive protein spots were identified by PMF using MALDI-mass spectrometry. The proteins were grouped according to the protein classification described in Cole et al. (Nature 393 (1998), 537), which is deduced from the *E. coli* gene classification of Riley (Microbiol. Rev. 57 (1993), 862). The numbers in brackets after each category refer to the total number of genes of this category (3). n.d., spot was not investigated; -, spot is absent; *, identified by MALDI-MS

| Spot No | Chic CP | Cop CP | H37Rv CP | Erdman CP | Cop CSN | H37Rv CSN | NCBI AccNo. | Protein name | Short-name | Rv-name |
|---|---|---|---|---|---|---|---|---|---|---|

I Small-molecule metabolism

A Degradation (163)

1. Carbon compounds (22)

| 65 | A382* | A171 | A436 | A243 | n.d. | n.d. | 1871608 | Succinate-semialdehyde dehydrogenase | gabD2 | Rv0234c |
| 222 | B14* B26* | B41+ B65 | B47 | B30 | n.d. | n.d. | 1654033 | Succinate semialdehyde dehydrogenase | gabD1 | Rv1731 |

2. Amino acids and amines (18)

| 134 | A260* | A91 | A301 | A415 | n.d. | n.d. | 2911027 | Methylmalonate semialdehyde dehydrogenase | mmsA | Rv0753c |

-continued

| | | | | | | | | | | |
|---|---|---|---|---|---|---|---|---|---|---|
| 117 255 | — | — | A132* | — | n.d. | A134* | 231985 2624302 | L-Alanine dehydrogenase (40kD Antigen) | ald | Rv2780 |
| 196 254 | — | — | A481* | — | n.d. | A124* | 231985 2624302 | L-Alanine dehydrogenase (40kD Antigen) | ald | Rv2780 |

3. Fatty acids (119)

| | | | | | | | | | | |
|---|---|---|---|---|---|---|---|---|---|---|
| 146 | B119* | B28 | B34 | B3 | n.d. | n.d. | 1850115 | Acyl CoA synthase; similar to LCFA_ECOLI P29212 long-chain-fatty-acid-CoA ligase | fadD2 | Rv0270 |
| 208a | C600* | C337 | C523 | C384 | n.d. | n.d. | 2909544 | 3-Hydroxyacyl-CoA dehydrogenase | fadB2 | Rv0468 |
| 39 | C360* | C377 | C385 | C452 | n.d. | n.d. | 1877369 | Enoyl-CoA hydratase | echA3 | Rv0632c |
| 111 | C456* | C488 | C576 | C552 | n.d. | n.d. | 1706568 | Enoyl-CoA hydratase/ isomerase superfamily | echA6 | Rv0905 |
| 125 169 | A432* | A155 | A627* | A310 | n.d. | n.d. | 2896711 | Acetyl-CoA C-acetyltransferase | fadA3 | Rv1074c |
| 124 | A424* | A569 | A397 | A237 | n.d. | n.d. | 1729939 | Acetyl-CoA acetyltransferase | fadA4 | Rv1323 |
| 219 | A124* | A498 | A170 | A412 | n.d. | n.d. | 2916977 | Acyl-CoA dehydrogenase/ hypothetical protein MTV047.14 | fadE16 | Rv1679 |
| 128 | A547* | A487 | A566 | A635 | n.d. | n.d. | 1877329 | Acyl-CoA dehydrogenase | fadE25 | Rv3274c |
| 73 | A518* | A100 | A182 | A409 | n.d | n.d. | 2916919 | β oxidation complex, α subunit (multiple activities) | fadB | Rv0860 |
| 74 | A272* | A328 | A319 A392 | A534 | n.d | n.d. | 2916919 | β oxidation complex, α subunit (multiple activities) | fadB | Rv0860 |

4. Phosphorous compounds (4)

| | | | | | | | | | | |
|---|---|---|---|---|---|---|---|---|---|---|
| 18 264 | C654* | C528 | C230 | C171 | n.d. | C42* | 2105066 | Probable inorganic pyrophosphatase | ppa | Rv3628 |

B Energy Metabolism (292)
1. Glycolysis (12)

| | | | | | | | | | | |
|---|---|---|---|---|---|---|---|---|---|---|
| 49 182 | C627* | C416 | C59* | C615 | n.d. | n.d. | 2094844 | Fructose bisphosphate aldolase | fba | Rv0363c |
| 206 | A353* | A517 | A626 | A50 | n.d. | n.d. | 3122120 | Glyceraldehyde 3-phosphate dehydrogenase | gap | Rv1436 |
| 131 | A218* | A278 | A489 | A636 | n.d. | n.d. | 2131060 | Glyceraldehyde 3-phosphate dehydrogenase | gap | Rv1436 |
| 223 | C511* | C500 | C67 | C482 | n.d. | n.d. | 2131058 | Triosephosphate isomerase | tpi | Rv1438 |

2. Pyruvate dehydrogenase (6)

| | | | | | | | | | | |
|---|---|---|---|---|---|---|---|---|---|---|
| 151 | A305* | A255+ A301 | A243 | A532 | n.d. | n.d. | 2909538 | Probable dihydrolipoamide dehydrogenase | — | Rv0462 |
| 152 | A549* | A468 | A325 | A45 | n.d. | n.d. | 2909538 | Probable dihydrolipoamide dehydrogenase | — | Rv0462 |

3. TCA cycle (19)

| | | | | | | | | | | |
|---|---|---|---|---|---|---|---|---|---|---|
| 118 | — | C501 | C527* | C336 | n.d. | n.d. | 1524210 | Succinyl-CoA synthase alpha chain | sucD | Rv0952 |
| 100 | C597* | C402 | C404 | C473 | n.d. | n.d. | 1524210 | Succinyl-CoA synthase alpha chain | sucD | Rv0952 |
| 209 47 | C645* | C501 | — | — | n.d. | n.d. | 1524210 | Succinyl-CoA synthase alpha chain | sucD | Rv0952 |
| 127 170 | A542* | A516 | A117* | A57 | n.d. | n.d. | 2896735 | Fumarase | fum | Rv1098c |
| 63 2 | C333* | C604 | A500 | C142 | n.d. | n.d. | 2695826 | Malate dehydrogenase | mdh | Rv1240 |
| 147 | A106* | A176 | — | — | n.d. | n.d. | 2791409 | Aconitate hydratase | acn | Rv1475c |
| 148 | A543* | A423 | — | — | n.d. | n.d. | 2791409 | Aconitate hydratase | acn | Rv1475c |

4. Glyoxylate bypass (5)

| | | | | | | | | | | |
|---|---|---|---|---|---|---|---|---|---|---|
| 136 | A357* | A426 | A406 | A316 | n.d. | n.d. | 1483535 | Malate synthase | glcB | Rv1873c |

5. Pentose phosphate pathway (11)
6. Respiration (60)
a. Aerobic (30)

25

| | | | | | | | | | | |
|---|---|---|---|---|---|---|---|---|---|---|
| 101 | C342* | C361 | C356 | C416 | n.d. | n.d. | 1781221 | NADH dehydrogenase chain c | nuoC | Rv3147 | b. Anaerobic (15)
c. Electron transport (15)

| | | | | | | | | | | |
|---|---|---|---|---|---|---|---|---|---|---|
| 7 203 280 | C507* | C540 | C598* | C222 | n.d. | C40* | 2791626 | Electron transfer flavoprotein α subunit | fixB | Rv3028c |
| 281 | n.d. | n.d | n.d. | n.d. | n.d. | C33* | 2791626 | Electron transfer flavoprotein α subunit | fixB | Rv3028c |
| 20 186 | C191* | C113 | C559* | C145 | n.d. | n.d. | 2414529 | Electron transfer flavoprotein β subunit | fixA | Rv3029c |

7. Miscellaneous oxidoreductases and oxygenases (171)

| | | | | | | | | | | |
|---|---|---|---|---|---|---|---|---|---|---|
| 179 | — | — | D92* | — | n.d. | n.d. | 2808725 | Probable oxidoreductase | — | Rv0068 |
| 305 | D138 | — | — | D100* | n.d. | n.d. | 2808725 | Probable oxidoreductase | — | Rv0068 |
| 22 | C305* | C496 | C577 | C445 | n.d. | n.d. | 1877273 | Steroid dehydrogenase | — | Rv0148 |
| 23 | C321* | C340 | C338 | C394 | n.d. | n.d. | 1877273 | Steroid dehydrogenase | — | Rv0148 |
| 23 | C557* | C471 | C339 | C388 | n.d. | n.d. | 1877273 | Steroid dehydrogenase | — | Rv0148 |
| 38 | C379* | C388 | C392 | C465 | n.d. | n.d. | 1877273 | Steroid dehydrogenase | — | Rv0148 |
| 38 | C594* | C492 | C394 | C466 | n.d. | n.d. | 1877273 | Steroid dehydrogenase | — | Rv0148 |
| 230 | C653* | C308 | C303 | C353 | n.d. | n.d. | 1877273 | Steroid dehydrogenase | — | Rv0148 |
| 96 | C129* | D86 | D81 | D88 | n.d. | n.d. | 2695831 | Putative dehydrogenase | — | Rv1245c |
| 228 | C350* | C359 | C352 | C410 | n.d. | n.d. | 2791388 | Quinone oxidoreductase | qor | Rv1454c |
| 105 | D230* | D115 | B2 | B23 | n.d. | n.d. | 1694883 | Putative oxidoreductase | — | Rv2951c |
| 180 236 | — | — | C125* | C143* | n.d. | n.d. | 1694860 | Oxidoreductase of aldo/keto reductase family | — | Rv2971 |
| 210 | C126* | C134 | — | — | n.d. | n.d. | 1694860 | Oxidoreductase of aldo/keto reductase family | — | Rv2971 |
| 129 | A180* | C585 | A490 | A309 | n.d. | n.d. | 399009 | NADP-dependent alcohol | adhC | Rv3045 |

| | | | | | | | | | | |
|---|---|---|---|---|---|---|---|---|---|---|
| 51 | C522* | C2 | C41* | C310 | n.d. | n.d. | 2072661 | dehydrogenase Putative oxidoreductase | — | Rv3224 |
| 160 221 | C274* | C286 | C293 | C334 | n.d. | n.d | 886104 | Putative dehydrogenase | — | Rv3389c |
| 95 | C462* | C451 | C482 | C560 | n.d. | n.d. | 2104408 | Short-chain alcohol dehydrogenase family | — | Rv3485c |

8. ATP-proton motive force (8)

| | | | | | | | | | | |
|---|---|---|---|---|---|---|---|---|---|---|
| 112 | A6* | A247 | A425 | A116 | n.d. | n.d. | 1703652 | ATP synthetase alpha chain | atpA | Rv1308 |

C Central Intermediary Metabolism (45)
   1. General (13)

| | | | | | | | | | | |
|---|---|---|---|---|---|---|---|---|---|---|
| 10 | C500* | C578 | A496 | C235 | n.d. | n.d. | 1877280 | Pyridine transhydrogenase subunit α1 | pntAA | Rv0155 |

2. Gluconeogenesis (2)

| | | | | | | | | | | |
|---|---|---|---|---|---|---|---|---|---|---|
| 153 | A114* | A427 | A48 | A512 | n.d. | n.d. | 1871584 | Phosphoenolpyruvate carboxykinase | pckA | Rv0211 |

3. Sugar nucleotides (14)

| | | | | | | | | | | |
|---|---|---|---|---|---|---|---|---|---|---|
| 311 | C314* | C331 | C330 | C381 | n.d. | n.d. | 2496483 | Probable β-phosphoglucomutase/28.2 kD protein CY78.28C | — | Rv3400 |

4. Amino sugars (1)
   5. Sulphur metabolism (15)

| | | | | | | | | | | |
|---|---|---|---|---|---|---|---|---|---|---|
| 194 | A220* | A228 | — | — | n.d. | n.d. | 2143298 | Probable arylsulphatase | atsD | Rv0663 |

D Amino Acid Biosynthesis (95)
   1. Glutamate family (19)

| | | | | | | | | | | |
|---|---|---|---|---|---|---|---|---|---|---|
| 155 304 | D31* | D26 | D28 | D20* | n.d. | n.d. | 3023331 | N-acetyl-γ-glutamyl-phosphate reductase | argC | Rv1652 |
| 227 302 | C661* | C389 | C393 | C458* | n.d. | n.d. | 1839006 | Acetylglutamatekinase | argB | Rv1654 |
| 156 | A344* | A395 | B17* | A195* | n.d. | n.d. | 1839007 | Acetylornithine | argD | Rv1655 |

| | | | | | | | | | | |
|---|---|---|---|---|---|---|---|---|---|---|
| 198 | | | | | | | 2829813 | aminotransferase | | |
| 235 | | | | | | | | | | |
| 226 | A332* | A386 | A386* | A511* | n.d. | n.d. | 1839007 | Acetylornithine aminotransferase | argD | Rv1655 |
| 197 | | | | | | | 2829813 | | | |
| 234 | | | | | | | | | | |

2. Aspartate family (21)

| | | | | | | | | | | |
|---|---|---|---|---|---|---|---|---|---|---|
| 215 | C386* | C405 | C409 | C480 | n.d. | n.d. | 1729955 | Homoserine synthase | thrC | Rv1295 |
| 81 | A91* | A534 | — | — | n.d. | n.d. | 1542900 | S-adenosylmethionine synthase | metK | Rv1392 |
| 115 | — | — | A264* | A226 | n.d. | n.d. | 1542900 | S-adenosylmethionine synthase | metK | Rv1392 |
| 225 | C398* | C410 | C417 | C486 | n.d. | n.d. | 2498290 | Dihydrodipicolinate reductase | dapB | Rv2773c |

3. Serine family (15)

| | | | | | | | | | | |
|---|---|---|---|---|---|---|---|---|---|---|
| 229 | C539* | C287 | C286 | C332 | n.d. | n.d. | 2076692 | Thiosulfate sulfurtransferase | cysA2 | Rv0815c |
| 154 | A193* | A241 | A224 | A328 | n.d. | n.d. | 2896714 | Cystathionine β-synthase | cysM2 | Rv1077 |
| 12 | A545* | A391 | B13 | A520 | n.d. | n.d. | 2896730 | Serine hydroxymethyltransferase | glyA | Rv1093 |
| 13 | B84* | B15 | B60 | A530 | n.d. | n.d. | 2896730 | Serine hydroxymethyltransferase | glyA | Rv1093 |

4. Aromatic amino acid family (15)
5. Histidine (11)
6. Pyruvate family (1)
7. Branched amino acid family (13)

| | | | | | | | | | | |
|---|---|---|---|---|---|---|---|---|---|---|
| 212 | A51* | A542 | A608 | A141 | n.d. | n.d. | 2924446 | Probable acetohydroxyacid synthase I large subunit | ilvX | Rv3509c |
| 174 | — | — | A186* | A312 | n.d. | n.d. | 2960134 | 2-Isopropylmalate synthase | leuA | Rv3710 |

E Polyamine synthesis (1)

F Purines, Pyrimidines, Nucleosides and Nucleotides (60)
  1. Purine ribonucleotide biosynthesis (20)
  2. Pyrimidine ribonucleotide biosynthesis (9)
  3. 2'-deoxyribonucleotide metabolism (12)
  4. Salvage of nucleosides and nucleotides (10)

| | | | | | | | | | | |
|---|---|---|---|---|---|---|---|---|---|---|
| 94 | C458* | C445 | C472 | C549 | n.d. | n.d. | 1870011 | Ribose-phosphate-pyrophosphokinase | prsA | Rv1017c |
| 137 | A186* | A237 | A233 | A320 | n.d. | n.d. | 1449391 | GMP synthase | guaA | Rv3396c |
| 138 | A500* | A463 | A247 | A352 | n.d. | n.d. | 1449391 | GMP synthase | guaA | Rv3396c |

5. Miscellaneous nucleoside/nucleotide reactions (9)

| | | | | | | | | | | |
|---|---|---|---|---|---|---|---|---|---|---|
| 21a | C241* | C248 | C254 | C289 | n.d. | C61* | 2911007 | Adenylate kinase | adk | Rv0733 |
| 265 | | | | | | | | | | |

G Biosynthesis of cofactors, prosthetic groups and carriers (117)
1. Biotin (8)
2. folic acid (11)
3. Lipoate (2)
4. Molybdopterin (20)
5. Panthotenate (4)
6. Pyridoxine (1)
7. Pyridine nucleotide (4)

| 116 | — | — | C266* | C298 | n.d. | n.d. | 2117241 | Nicotinate-nucleotide pyrophosphatase | nadC | Rv1596 |
|---|---|---|---|---|---|---|---|---|---|---|

8. Thiamine (4)
9. Riboflavine (8)
10. Thioredoxin, glutaredoxin and mycothiol (8)

| 208b | C600* | C337 | C523 | C384 | n.d. | n.d. | 2808698 | Thioredoxin reductase | trxB2 | Rv3913 |
|---|---|---|---|---|---|---|---|---|---|---|
| 213 | C584* | C564 | — | C338 | n.d. | n.d. | 2808698 | Thioredoxin reductase | trxB2 | Rv3913 |
| 80 | E95* | E124 | E82 | E143 | n.d. | n.d. | 1729947 | Thioredoxin | trxC | Rv3914 |

11. Menaquinone, PQQ, ubiquinone, and other terpenoids (15)
12. Heme and porphyrin (9)
13. Cobalamin (17)
14. Iron utilization (6)

H Lipid Biosynthesis (65)
1. Synthesis of fatty and mycolic acids (26)

| 217 224 | A476* | A387 | A610* | A503 | n.d. | n.d. | 2909446 | 3-Oxoacyl-[ACP] reductase | fabG4 | Rv0242c |
|---|---|---|---|---|---|---|---|---|---|---|
| 59 | B116* | — | — | — | n.d. | n.d. | 2909446 | 3-Oxoacyl-[ACP] reductase | fabG4 | Rv0242c |
| 59 | B46* | — | — | — | n.d. | n.d. | 2909446 | 3-Oxoacyl-[ACP] reductase | fabG4 | Rv0242c |
| 25 | C414* | C429 | C443 | C515 | n.d. | n.d. | 1170564 | Enoyl[ACP]reductase | inhA | Rv1484 |
| 107 | D145* | D103 | D100 | D107 | n.d. | n.d. | 1155269 | Enoyl[ACP]reductase | inhA | Rv1484 |
| 132 | A222* | A485 | A266 | A371 | n.d. | n.d. | 1706747 | β-ketoacyl-ACP synthase | kasB | Rv2246 |
| 141 | A207* | A675 | A199 | A345 | n.d. | n.d. | 1877335 | Acetyl/propionyl CoA carboxylase β subunit | accD5 | Rv3280 |

2. Modification of fatty and mycolic acids (14)

| 214 | C585* | C502 | C50 | C340 | n.d. | n.d. | 1575549 | Methoxy mycolic acid synthase 4 | mmaA4 | Rv0642c |
|---|---|---|---|---|---|---|---|---|---|---|

3. Acyltransferases, mycoltransferases and phospholipid synthesis (25)

| 104 | B5* | D113 | B14 | B2 | n.d. | n.d. | 1723008 | Probable fattyacid-acyl CoA reductase | — | Rv1543 |
|---|---|---|---|---|---|---|---|---|---|---|
| 251 | n.d. | n.d. | n.d. | n.d. | n.d. | C45* | 393879 | Antigen 85B precursor | fbpB | Rv1886c |

-continued

| | | | | | | | | | | |
|---|---|---|---|---|---|---|---|---|---|---|
| 37 267 | C335* | C372 | C363 | C425 | n.d. | C125* | 804884 2578420 | Antigen MPT51, mycolyl transferase, MPB51 precursor | fbpD | Rv3803c |
| 102 184 | C540* | C319 | C159* | C361 | n.d. | n.d. | 112764 | Antigen 85A precursor | fbpA | Rv3804c |
| 249 | n.d. | n.d. | n.d. | n.d. | n.d. | C58* | 112765 | Antigen 85A precursor | fbpA | Rv3804c |
| 250 | n.d. | n.d. | n.d. | n.d. | n.d. | C14* | 112765 | Antigen 85A precursor | fbpA | Rv3804c |

I Polyketide and Non-Ribosomal Peptide Synthesis (41)

| | | | | | | | | | | |
|---|---|---|---|---|---|---|---|---|---|---|
| 98 | D180* | D118 | — | — | n.d. | n.d. | 1403498 | Probable ketoacyl reductase | — | Rv1544 |

J Broad regulatory functions (187)
   1. Repressors/activators (143)

| | | | | | | | | | | |
|---|---|---|---|---|---|---|---|---|---|---|
| 11 199 | A8* | A726 | A267* | — | n.d. | n.d. | 2791413 | Transcriptional regulator MoxR homologue | moxR | Rv1479 |
| 232 | — | — | — | A473* | n.d. | n.d. | 2791413 | Transcriptional regulator, MoxR homologue | moxR | Rv1479 |
| 120 | — | — | D12* | D115 | n.d. | n.d. | 2960100 | Transcriptional regulator (Crp/Fnr family) | — | Rv3676 |
| 121 | D174 | D111* | D115 | D130 | n.d. | n.d. | 2960100 | Transcriptional regulator (Crp/Fnr family) | — | Rv3676 |

2. Two component systems (30)

| | | | | | | | | | | |
|---|---|---|---|---|---|---|---|---|---|---|
| 24 | C561* | C227 | C222 | C266 | n.d. | n.d. | 2113910 | Two-component response regulator; similar also to chemotaxis proteins | — | Rv1626 |
| 36 | C659* | C415 | C214 | C493 | n.d. | n.d. | 1781234 | Two-component response regulator | — | Rv3133c |

3. Serine-threonine protein kinases and phosphoprotein phosphatases (14)

II Macromolecule Metabolism

A Synthesis and Modification of Macromolecules (215)
   1. Ribosomal protein synthesis and modification (58)

| | | | | | | | | | | |
|---|---|---|---|---|---|---|---|---|---|---|
| 70 294 | F52* | F28 | F45 | F47 | n.d. | F9* | 1568592 2829551 | 30 S Ribosomal protein S6 | rpsF | Rv0053 |
| 309 | D131* | D154 | D84 | D93 | n.d. | n.d. | 1877389 | 50 S Ribosomal protein L10 | rplJ | Rv0651 |
| 28 16 164 | E54* | E42 | E42* | E77 | n.d. | n.d. | 585892 | 50 S Ribosomal protein L7/L12 | rplL | Rv0652 |
| 82 | E173* | — | E138 | E206 | n.d. | n.d. | 1806177 | 50 S Ribosomal protein L29 | rpmC | Rv0709 |

2. Ribosome modification and maturation (3)
3. Aminoacyl tRNA synthases and their modification (26)
4. Nucleoproteins (4)

| 72 | F95* | — | — | — | n.d. | n.d. | 1857251 1542896 | Integration host factor | mIHF | Rv1388 |
|---|---|---|---|---|---|---|---|---|---|---|

5. DNA replication, repair, recombination and restriction/modification (69)

| 19 256 | C272* | C277 | C226 | C318 | n.d. | C6* | 1568593 | Single strand binding protein | ssb | Rv0054 |
|---|---|---|---|---|---|---|---|---|---|---|

6. Protein translation and modification (15)

| 34 167 237 | D12* | D41 | D39* | D35 | n.d. | D7* | 1552563 2829514 | Peptidyl-prolyl cis-trans isomerase (rotamase) | ppiA | Rv0009 |
|---|---|---|---|---|---|---|---|---|---|---|
| 238 | n.d. | n.d. | n.d. | n.d. | n.d. | D5* | 2829514 | Peptidyl-prolyl cis-trans isomerase | ppiA | Rv0009 |
| 239 | n.d. | n.d. | n.d. | n.d. | n.d. | C112* | 2829514 | Peptidyl-prolyl cis-trans isomerase | ppiA | Rv0009 |
| 299 | n.d. | n.d. | n.d. | n.d. | n.d. | C119* | 2829514 | Peptidyl-prolyl cis-trans isomerase | ppiA | Rv0009 |
| 135 172 | A572* | A452 | A349* | A339 | n.d. | n.d. | 3261535 | Elongation factor G | fusA | Rv0684 |
| 173 | A148 | — | A187* | A509 | n.d. | n.d. | 2181962 | Elongation factor G | fusA2 | Rv0120c |
| 3 159 268 | A540* | A579 | A587* | A601 | n.d. | A106* | 399422 1333784 | Elongation Factor EF-Tu | tuf | Rv0685 |
| 269 | n.d. | n.d. | n.d. | n.d. | n.d. | A91* | 399422 1333784 | Elongation Factor EF-Tu | tuf | Rv0685 |
| 279 | n.d. | n.d. | n.d. | n.d. | n.d. | A9* | 399422 1333784 | Elongation Factor EF-Tu | tuf | Rv0685 |
| 296 | n.d. | n.d. | n.d. | n.d. | n.d. | A82* | 399422 1333784 | Elongation Factor EF-Tu | tuf | Rv0685 |
| 33 | E86* | E65 | E61 | E110 | n.d. | n.d. | 2896717 | Transcription elongation factor G | greA | Rv1080c |
| 240 | n.d. | n.d. | n.d. | n.d. | n.d. | C108* | 1710712 | Ribosome recycling factor | frr | Rv2882c |
| 241 | n.d. | n.d. | n.d. | n.d. | n.d. | C91* | 1710712 | Ribosome recycling factor | frr | Rv2882c |
| 103 185 263 | C309* | C329 | C324* | C377 | n.d. | C71* | 1706595 | Elongation factor Ts (EF-Ts) | tsf | Rv2889c |

7. RNA synthesis, RNA modification and DNA transcription (32)

| 1b | C100* | C601 | C199 | C522 | n.d. | n.d. | 1877377 | Transcription antitermination protein | nusG | Rv0639 |
|---|---|---|---|---|---|---|---|---|---|---|
| 56 144 | A235* | A298 | A285 | A527 | n.d. | n.d. | 1710260 | Transcription termination factor Rho | rho | Rv1297 |
| 57 145 | A246* | A309 | A297 | A236 | n.d. | n.d. | 1710260 | Transcription termination factor Rho | rho | Rv1297 |
| 58 | A259* | A317 | A312 | A238 | n.d. | n.d. | 1710260 | Transcription termination factor Rho | rho | Rv1297 |
| 4 | A435* | A324 | A616 | A621 | n.d. | n.d. | 2104380 | α Subunit of RNA polymerase | rpoA | Rv3457c |
| 61 | A40* | A330 | A615 | A622 | n.d. | n.d. | 2104380 | α Subunit of RNA polymerase | rpoA | Rv3457c |

8. Polysaccharides (8)

B Degradation of Macromolecules (87)
   1. RNA (6)
   2. DNA (3)
   3. Proteins, peptides and glycopeptides (34)

| 195 | A268 | A332 | A320* | — | n.d. | n.d. | 1806192 | Protein IV, signal peptide peptidase | sppA | Rv0724 |
|---|---|---|---|---|---|---|---|---|---|---|

4. Polysaccharides, lipopolysaccharides and phospholipids (8)

| 97 | D136* | D82 | — | D96 | n.d. | n.d. | 2104386 | Probable neuraminidase | — | Rv3463 |
|---|---|---|---|---|---|---|---|---|---|---|
| 191 | D99* | D3 | D64 | D67 | n.d. | n.d. | 2104386 | Probable neuraminidase | — | Rv3463 |
| 192 | D122* | D82 | D78 | D84 | n.d. | n.d. | 2104386 | Probable neuraminidase | — | Rv3463 |

5. Esterases and lipases (27)
   6. Aromatic hydrocarbons (9)

C Cell Envelope (366)
   1. Lipoproteins (65)
   2. Surface polysaccharides (39)

III Cell processes

A Transport/Binding Proteins (124)
   1. Amino acids (18)
   2. Cations (31)
   3. Carbohydrates, organic acids and alcohols (19)

| 270 566 | — | — | C71 | C84* | n.d. | C24* | 127271 | Secreted immunogenic protein MPB64/MPT64 | mpt64 | Rv1980c |
|---|---|---|---|---|---|---|---|---|---|---|
| 9 | C648* | C156 | C221 | C187 | n.d. | n.d. | 1168374 | Antigen 84 | wag31 | Rv2145c |

3. Murein sacculus and peptidoglucan (28)
   4. Conserved membrane proteins (23)
   5. Other membrane proteins (211)

4. Anions (34)
   5. Fatty acid transport (2)
   6. Efflux proteins (20)

| 89 | D46* | D116 + D156 | D9 | D7 | n.d. | n.d. | 1731190 | possible exported protein | — | Rv0475 |
|---|---|---|---|---|---|---|---|---|---|---|

B Chaperones/Heat shock (16)

| 6 157 | A16* | A132 | A368* | A212 | n.d. | n.d. | 416908 2094929 | 70 kD Heat shock protein | dnaK | Rv0350 |
|---|---|---|---|---|---|---|---|---|---|---|
| 261 | n.d. | n.d. | n.d. | n.d. | n.d. | A31* | 2094829 | 70 kD Heat shock protein | dnaK | Rv0350 |
| 66 | C69* | C526 | C132 | C4 | n.d. | n.d. | 417087 2094830 | Stimulates DnaK ATPase activity | grpE | Rv0351 |
| 8 168 | A524* | A5 | A600* | A158 | n.d. | n.d. | 2909505 | Heat shock protein | clpB | Rv0384c |
| 284 | n.d. | n.d. | n.d. | n.d. | A1* | | 2909505 | ClpB heat shock protein | clpB | Rv0384c |
| 284 | n.d. | n.d. | n.d. | n.d. | A69* | | 2909505 | ClpB heat shock protein | clpB | Rv0384c |
| 284 | n.d. | n.d. | n.d. | n.d. | A77* | | 2909505 | ClpB heat shock protein | clpB | Rv0384c |
| 5 158 262 | A67* | A743 | A431* | A556 | n.d. | A4 | 116244 | 60 kD Chaperonin 2 (Protein CPN60 2) (Groel Protein 2) (65 kD Antigen) (Heat shock protein 65) (Cell wall protein A) (Antigen A) | groEL2 | Rv0440 |
| 75 | A452* | A712 | A295 | A22 + A72 | n.d. | n.d. | 116244 | 60 kD Chaperonin 2 | groEL2 | Rv0440 |
| 123 | A418* | A144 | A613 | A246 | n.d. | n.d. | 116244 | 60 kD Chaperonin 2 | groEL2 | Rv0440 |

| | | | | | | | | | |
|---|---|---|---|---|---|---|---|---|---|
| 292 | n.d. | n.d. | n.d. | n.d. | n.d. | A24* | 116244 | 60 kD Chaperonin 2 | groEL2 Rv0440 |
| 27 15 166 275 | E103* | E84 | E166* | E148 | n.d. | E18* | 231343 | 14 kD Antigen | hspX Rv2031c |
| 271 | n.d. | n.d. | n.d. | n.d. | n.d. | E54* | 231343 | 14 kD Antigen (16 kD Antigen) (Hsp 16.3) | hspX Rv2031c |
| 272 | n.d. | n.d. | n.d. | n.d. | n.d. | E11* | 231343 | 14 kD Antigen (16 kD Antigen) (Hsp 16.3) | hspX Rv2031c |
| 273 | n.d. | n.d. | n.d. | n.d. | n.d. | E53* | 231343 | 14 kD Antigen (16 kD Antigen) (Hsp 16.3) | hspX Rv2031c |
| 274 | n.d. | n.d. | n.d | n.d. | n.d. | E38* | 231343 | 14 kD Antigen (16 kD Antigen) (Hsp 16.3) | hspX Rv2031c |
| 285 | n.d. | n.d. | n.d. | n.d. | n.d. | E51* | 231343 | 14 kD Antigen (16 kD Antigen) (Hsp 16.3) | hspX Rv2031c |
| 69 | F58* | F29 | F47 | F51 | n.d. | n.d. | 1877324 | Probable heat shock protein, similar to YW26__MYCTU Q10865 hypothetical 10.5 kd protein | — Rv3269 |
| 64 | A14* | A133 | A432 | A267 | n.d. | n.d. | 421608 1449370 | Heat shock protein groEL Gpn60-1/60 kD chaperonin 1 | groEL1 Rv3417c |
| 17 165 | E14* | E44 | E100* | E231 | n.d. | n.d. | 116198 | 10 kD Chaperonin (Protein CPN10) (Protein GroES) (immunogenic Protein MPB57) | groES Rv3418c |
| 242 | n.d. | n.d. | n.d. | n.d. | n.d. | E45* | 116200 | 10 kD Chaperonin | groES Rv3418c |
| 243 | n.d. | n.d. | n.d. | n.d. | n.d. | E44* | 116200 | 10 kD Chaperonin | groES Rv3418c |
| 244 | n.d. | n.d. | n.d. | n.d. | n.d. | E46* | 116200 | 10 kD Chaperonin | groES Rv3418c |
| 245 | n.d. | n.d. | n.d. | n.d. | n.d. | E42* | 116200 | 10 kD Chaperonin | groES Rv3418c |
| 246 | n.d. | n.d. | n.d. | n.d. | n.d. | E41* | 116200 | 10 kD Chaperonin | groES Rv3418c |

C Cell division (19)

| | | | | | | | | | |
|---|---|---|---|---|---|---|---|---|---|
| 190 231 | D92* | D158 | — | D59* | n.d. | n.d. | 2072672 | Very similar to Soj protein possible role in chromosome segregation | — Rv3213c |

D Protein and peptide secretion (14)

| | | | | | | | | | |
|---|---|---|---|---|---|---|---|---|---|
| 52 | A10* | A407 | A92 | A651 | n.d. | n.d. | 2791502 | Putative chaperone protein | tig Rv2462c |

E Adaptions and atypical conditions (12)

| | | | | | | | | | |
|---|---|---|---|---|---|---|---|---|---|
| 68 277 | E135* | E41 + E88 | E101 | E168 + E174 | n.d. | E23* | 2105046 2811046 | Cold shock protein, transcriptional regulator | cspA Rv3648c |

F Detoxification (22)

| | | | | | | | | | | |
|---|---|---|---|---|---|---|---|---|---|---|
| 108 | E32* | E21 | C44 | C36 | n.d. | n.d. | 2501346 | Thiol peroxidase | tpx | Rv1932 |
| 43 | C31* | C527 | C53 | C437 | n.d. | n.d. | 2127453 | Alkyl hydroperoxide reductase chain C | ahpC | Rv2428 |
| 42 | D91* | D57 | D54 | — | n.d. | n.d. | 2127455 | Member of AhpC/TSA family | ahpD | Rv2429 |

IV Other

A Virulence (38)

B IS elements, Repeated sequences, and Phage (135)
 1. IS elements (90)
  a IS6110 (32)
  b IS1081 (6)
  c others (52)

| 21b | C241* | C248 | C254 | C289 | n.d. | n.d. | 1869987 | Probable transposase | — | Rv1041c |

2. REP13E12 family (10)

3. Phage-related functions (35)

C PE and PPE families (167)
 1. PE family (99)
  a. PE subfamily (38)
  b. PE_PGRS subfamily (61)
 2. PPE family (68)

D Antibiotic Production and Resistance (14)

E Bacteriocin-Like Proteins (3)

F Cytochrome P450 Enzymes (22)

G Coenzyme F420-dependent enzymes (3)

| 189 | C368* | C387 | — | C459 | n.d. | n.d. | 1817673 | Probable coenzyme F420-dependent enzyme | — | Rv0407 |

H Miscellaneous transferases (61)

| 133 | A302* | A2  | A482 | A462 | n.d. | n.d. | 2791398 | Nifs-like protein  | — | Rv1464  |
| 93  | D28*  | D23 | D24  | C590 | n.d. | n.d. | 2326746 | o-Methyltransferase | — | Rv1703c |

I Miscellaneous phosphatases, lyases, and hydrolases (18)

| 200 | D98 | D65 | D10* | — | n.d. | n.d. | 2494371 | Haloalkane dehalogenase | — | Rv2296 |

J Cyclases (6)

K Chelatases (2)

V Conserved Hypotheticals (912)

| 54 301 | A32 | A62 | A66* | A115 | n.d. | A34* | 1552575 | MLB1770.15c similar to E235827/ hypothetical 38.4 kD protein | — | Rv0020c |
|---|---|---|---|---|---|---|---|---|---|---|
| 53 | A29* | A38 | A56 A576 | — | n.d. | n.d. | 1552575 | MLB1770.15c similar to E235827/ hypothetical 38.4 kD protein | — | Rv0020c |
| 202 | — | C178 | C176* | C404 | n.d. | n.d. | 1552591 | Hypothetical 27.6 kDa protein | — | Rv0036c |
| 126 | A150* | A134 | A151 | A219 | n.d. | n.d. | 1568585 | Similar to *M. leprae* G466956B1620_F3_113 | — | Rv0046c |
| 60 | D248* | D159 | — | — | n.d. | n.d. | 1871589 | Hypothetical protein MTCY08D5.11 | — | Rv0216 |
| 293 | n.d. | n.d. | n.d. | n.d. | n.d. | D15* | 2909625 | Hypothetical protein MTV039.04c | — | Rv0566c |
| 86 286 | E122* | — | E137 | E32 | n.d. | E28* | 2909628 | Hypothetical protein MTV039.07 | — | Rv0569 |
| 84 | F19* | F12 | F18 | F18 | n.d. | n.d. | 1524195 | Similar to MTV007.08, similar to G1001429/ hypothetical 18.9 kd protein | — | Rv0967 |
| 67 | F12* | — | — | F13 | n.d. | n.d. | 1524194 | Conserved hypothetical | — | Rv0968 |
| 207 | A202* | A254 | A249 | A350 | n.d. | n.d. | 2896736 | Hypothetical protein Rv1099c; similar to YWJI_BACSU (52.1%) | — | Rv1099c |
| 99 | C376* | C589 | C389 | C463 | n.d. | n.d. | 1929075 | Similar to *M. leprae* Q49948 U1756F | — | Rv1201c |
| 201 233 | E152 | E109 | C376* | E192* | n.d. | n.d. | 1722951 | Hypothetical 18.2 kD Protein CY373.03 similar to carboanhydrase | — | Rv1284 |
| 295 | n.d. | n.d. | n.d. | n.d. | n.d. | F12* | 1723000 | Hypothetical 16.4 kD protein CY48.07C | — | Rv1558 |
| 14 | E160* | E114 | E127 | E199 | n.d. | n.d. | 2113920 | Conserved hypothetical | — | Rv1636 |
| 260 | n.d. | n.d. | n.d. | n.d. | n.d. | E22* | 2113920 | Conserved hypothetical | — | Rv1636 |
| 290 | n.d. | n.d. | n.d. | n.d. | n.d. | E52* | 2113920 | Conserved hypothetical | — | Rv1636 |
| 205 | C184* | C330 | C181 | C671 | n.d. | n.d. | 2924475 | Similar to MTCY15F10.23 | — | Rv1794 |
| 83 | F3* | — | F5 | E222 | n.d. | n.d. | 2225985 | Hypothetical protein MTCY180.43c | — | Rv1875 |
| 303 | D13 | D11 | D59 | D153* | n.d. | n.d. | 1731252 | Hypothetical 33.9 kD Protein CY39.23C | — | Rv1996 |
| 183 | C406 | C422 | C521* | C502 | n.d. | n.d. | 1731241 | Conserved hypothetical 30.9 kDa protein | — | Rv2005c |
| 30 | E143* | E104 | C336 | E177 | n.d. | n.d. | 2104338 | Similar to hypothetical 17.1 kD *E coli* protein YbhB | — | Rv2140c |
| 258 | n.d. | n.d. | n.d. | n.d. | n.d. | C78* | 2104338 | Similar to hypothetical 17.1 kD *E. coli* protein YbhB | — | Rv2140c |
| 32 | E82* | E143 | E57 | E108 | n.d. | n.d. | 2911105 | Hypothetical protein | — | Rv2185c |
| 176 | — | B59 | B69* | B54 | n.d. | n.d. | 2791489 | Protein MTV008.05c | — | Rv2449c |
| 50 181 | C587* | C504 | C243* | C456 | n.d. | n.d. | 2104288 | Similar to YW12_MYCTU Q10851 hypothetical 30.9 kD protein cy39.12 | — | Rv2623 |
| 90 | E127* | — | — | — | n.d. | n.d. | 2104285 | Conserved hypothetical | — | Rv2626c |
| 91 | E126* | — | — | — | n.d. | n.d. | 2104285 | Conserved hypothetical | — | Rv2626c |
| 76 | E158* | E181 | E162 | E195 | n.d. | n.d. | 2104285 | Conserved hypothetical | — | Rv2626c |
| 79 | E1* | E74 | E75 | E156 | n.d. | n.d. | 2104285 | Conserved hypothetical | — | Rv2626c |
| 306 | E50 + E65 | E48 + E103 | — | E84* | n.d. | n.d. | 2829592 | Hypothetical 16.0 kD Protein CY441.11 YQCK_BACSU P45945 | — | Rv2641 |
| 48 161 | C171* | C424 | C30* | C303 | n.d. | n.d. | 398959 | 35 kD Antigen | 35kd_ag | Rv2744c |
| 193 | C226* | n.d. | C234 | C267 | n.d. | n.d. | 1781160 | Similar to hypothetical bacterial proteins/contains aminotransferase class-II pyridoxal-phosphate attachment site YieF_ECOLI (3e-20) P31465 | — | Rv3054c |
| 1a 140 | C100* | n.d. | C199 | C522 | n.d. | n.d. | 1781138 | Conserved hypothetical; similar to citrate lyase β-chains | — | Rv3075c |

-continued

| | | | | | | | | | |
|---|---|---|---|---|---|---|---|---|---|
| 310 178 | B100* | B51 | B10* | B12 | n.d. | n.d. | 2076700 | Similar to C-terminal part of hypothetical *M. tuberculosis* protein Y07J_MYCU Q11025/ similar to C-terminal part MTCY02B10.19C | — | Rv3127 |
| 29 | E156* | E111 | C387 | E193 | n.d. | n.d. | 1877314 | Conserved hypothetical | — | Rv3555c |
| 87 | F5* | F3 | F6 | E116 | n.d. | n.d. | 2113924 | Conserved-hypothetical | — | Rv3592 |
| 247 | n.d. | n.d. | n.d. | n.d. | n.d. | F3* | 2113924 | Conserved hypothetical | — | Rv3592 |
| 297 | n.d. | n.d. | n.d. | n.d. | n.d. | E50* | 2960226 | Hypothetical protein MTV02709 similar to TR: 033084 (EMBL: Y14967) MLCB628.13) | — | Rv3874 |
| 298 | n.d. | n.d. | n.d. | n.d. | n.d. | E5* | 2960226 | Hypothetical protein MTV027.09 similar to TR: 033084 (EMBL: Y14967) MLCB628.13) | — | Rv3874 |

VI Unknowns (606)

| | | | | | | | | | |
|---|---|---|---|---|---|---|---|---|---|
| 41 | F9* | F5 | F9 | E230 | n.d. | n.d. | 1877374 | Unknown | — | Rv0636 |
| 92 | C443* | C442 | C466 | C542 | n.d. | n.d. | 2896746 | Unknown | — | Rv1109c |
| 62 | C497* | C84 | A68 | C123 | n.d. | n.d. | 1722975 | some similarity to thioredoxins | — | Rv1324 |
| 287 | n.d. | n.d. | n.d. | n.d. | n.d. | E9* | 1806236 | Unknown | — | Rv1926c |
| 85 | E177* | E179 | E144 | E213 | n.d. | n.d. | 2104293 | Unknown | — | Rv2619c |
| 31 | E120* | E157 | C275 | E157 | n.d. | n.d. | 1552871 | Unknown; similar to GREA_MYGLE p46808 transcription elongation factor grea | — | Rv3788 |

| | |
|---|---|
| Total | 3924 |
| Found on 2-DE patterns (Rv Nos) | 150 |
| Investigated spots | 312 |
| Identified spots by PMF | 268 |
| Identified spots by PMF and PSD | 33 |
| Identified spots by pattern comparison | 267 |
| Several spots of one gene in one strain | 36 |
| Cells | 26 |
| Supernatants | 12 |
| Common spots identified in H37Rv and Chicago by PMF | 23 |
| Identified spots in BCG Chicago PMF | 152 |
| Pattern comparison | 10 |
| Identified spots in BCG Copenhagen PMF | 0 |
| Pattern comparison | 154 |
| Identified spots in M.tub H37Rv PMF | 41 |
| Pattern comparison | 113 |
| Identified spots in Mtub Erdman PMF | 12 |
| Pattern comparison | 144 |
| Identified spots in M.tub H37 Rv CSN PMF | 44 |
| Pattern comparison | — |
| Several genes in one spot (e.g. 1a and 1b, 21, 208) | 3 |
| in prep, not identified: | 44 |

| No | Spot No | new Spot No | NCBI AccNo | Name Sanger + NCBI | Short-name Sanger | Rv-name Sanger |
|---|---|---|---|---|---|---|
| 26 | C272(X9) (= D15) + C270 (= D14) | C579 C580 | | | | |
| 35 | C247 (X16) | C395 | 1781068 | unknown; similarityto hypothetical 20.4 kDa protein | | |
| 40 | F22 (X21) | F13 | | | | |
| 55 | A66 (X36) | A385 | | | | |
| 77 | E62 (X58) | G2 | | | | |
| 78 | E89 (X59) | E102 | | | | |
| 88 | E15 (X69) (= F2) | E186 | | | | |
| 109 | F54 | F63 | | | | |
| 110 | D19 | D18 | | | | |
| 113 | Tub1 | | | | | |
| 114 | Tub2 | | | | | |
| 119 | Tub7 | | 2072672 | unknown, similarity to Soj protein | | |
| 122 | Tub10 | | | | | |
| 130 | A333 | C521 | | | | |
| 139 | A95 | C87 | | | | |
| 142 | A413 | A226 | | | | |
| 143 | A47 | A519 | | | | |
| 149 | A307 | G4 | | | | |
| 150 | A521 | A297 | | | | |
| 162 | Tub16 | | | | | |

-continued

| No | Spot No | new Spot No | NCBI AccNo | Name Sanger + NCBI | Short-name Sanger | Rv-name Sanger |
|---|---|---|---|---|---|---|
| 163 | Tub17 | | | | | |
| 171 | Tub25 | | | | | |
| 175 | Tub29 (neu6) | | | | | |
| 177 | Tub31 (neu19) | | | | | |
| 188 | A467 | A257 | | | | |
| 204 | Tub54 | | | | | |
| 216 | B41/B22 (Doppelspot) | A342 A132 | | | | |
| 218 | C75 | C155 | | | | |
| 220 | C102 Tub CSN 12 | C641 F4 | | | | |
| 252 | Tub CSN 16 | C51 | | 398980 Antigen 85-C 1877254 Precursor 85c | | |
| 253 | Tub CSN 17 | A117 | | | | |
| 257 | Tub CSN 21 | C13 | | | | |
| 259 | Tub CSN 23 | C67 | | | | |
| 266 | Tub CSN 30 | E32 | | | | |
| 276 | Tub CSN 56 | E29 | | | | |
| 282 | Tub CSN 47 | A51 | | 2896711 beta-ketoacyl CoA thiolase | | |
| 283 | Tub CSN 48 | A30 | | | | |
| 288 | Tub CSN 55 | C20 | | | | |
| 289 | Tub CSN 59 | C44 | | | | |
| 291 | Tub CSN 70 | E25 | | | | |
| 300 | Tub CSN 62 | ??? nicht vorhanden | | | | |
| 307 | E28 | E42 | | | | |
| 308 | A184 (= C84) | C197 | | 2909470 hypothetical protein MTV035.09 | | |

Table 2: Protein variability between cell proteins (CP) of different strains. Four comparisons were performed: a, *M. bovis* BCG Chicago CP versus *M. tuberculosis* H37Rv CP; b, *M. tuberculosis* H37Rv CP versus Erdman CP; c, *M. bovis* BCG Chicago CP versus Copenhagen CP; and d, *M. bovis* Chicago CP versus *M. tuberculosis* Erdman CP. Each strain was prepared at least 3 times and at least gels of 3 independently prepared samples were compared. Some obvious differences were checked for reproducibility and only variations occurring reproducibly in all gels of one strain were accepted. From these 59 variant spots we identified 50 proteins. [↑] spot intensity increased; [↓] spot intensity decreased; [-] spot not detected on 2-DE pattern; mv mobility variant, spot position shifted, the following spot No corresponds to the shifted spot.

a) Comparison *M. bovis* BCG Chicago CP ↔ *M. tuberculosis* H37Rv CP

| No | BCG Chic CP | H37Rv CP | NCBI AccNo | Name | Short-name | Rv-name |
|---|---|---|---|---|---|---|
| 28 | E54 [↑] | E42 [↓] | 585892 | 50 S Ribosomal protein L7/L12 | rplL | Rv0652 |
| 42 | D91 [↑] | D54 [↓] | 2127455 | Member of AhpC/TSA family | ahpD | Rv2429 |
| 43 | C31 [↑] | C53 [↓] | 2127453 | Alkyl hydroperoxide reductase chain C | ahpC | Rv2428 |
| 81 | A91 | [—] MV A264 | 1542900 | S-adenosylmethionine synthase | metK | Rv1392 |
| 115 | [—] MV A91 | A264 | 1542900 | S-adenosylmethionine synthase | metK | Rv1392 |
| 86 | E122 [↑] | E137 [↓] | 2909628 | Hypothetical protein MTV039.07 | — | Rv0569 |
| 89 | D46 [↑] | D9 [↓] | 1731190 | Hypothetical 21.5 kD protein CY20G9.01 precursor; possible exported protein | — | Rv0475 |
| 130 | C521 [↑] | A228 [↓] | | Not identified | | |
| 188 | A257 | [—] | | Not identified | | |
| 189 | C368 | [—] | 1817673 | Probable coenzmyme F420-dependent enzyme | — | Rv0407 |
| 190 | D92 | [—] | 2072672 | Very similar to Soj protein, possible role in chromosome segregation | — | Rv3213c |

-continued

| No | BCG Chic CP | H37Rv CP | NCBI AccNo | Name | Short-name | Rv-name |
|---|---|---|---|---|---|---|
| 191 | D99 [↑] | D64 [↓] | 2104386 | Probable neuraminidase | — | Rv3463 |
| 192 | D122 [↑] | D78 [↓] | 2104386 | Probable neuraminidase | — | Rv3463 |
| 193 | C226 [↑] | C234 [↓] | 1781160 | Contains aminotransferase class II pyridoxal-phosphate attachment site | — | Rv3054c |
| 194 | A220 | [—] | 2143298 | Probable arylsulphatase | atsD | Rv0663 |
| 209 | C645 | [—] MV C527 | 1524210 | Succinyl-CoA synthase α chain | sucD | RV0952 |
| 118 | [—] MV C645 | C527 | 1524210 | Succinyl-CoA synthase α chain | sucD | Rv0952 |
| 210 | C126 | [—] MV C125 | 1694860 | Oxidoreductase of aldo/keto reductase family | — | Rv2971 |
| 180 | [—] MV C126 | C125 | 1694860 | Oxidoreductase of ado/keto reductase family | — | Rv2971 |
| 113 | [—] | A607 | | Not identified | | |
| 114 | [—] | A115 | | Not identified | | |
| 116 | [—] | C266 | 2117241 | Nicotinate-nucleotide pyrophosphatase | nadC | Rv1596 |
| 117 | [—] | A132 | 231985 | L-Alanine dehydrogenase (40 kD Antigen) | ald | Rv2780 |
| 162 | C155 [↓] | C151 [↑] | | Not identified | | |
| 174 | [—] | A186 | 2960134 | 2-Isopropylmalate synthase | leuA | Rv3710 |
| 176 | [—] | B69 | 2791489 | Conserved hypothetical protein MTV008.05c | — | Rv2449c |
| 177 | [—] | B3 | | Not identified | | |
| 179 | [—] MV D138 | D92 | 2808725 | Oxidoreductase | — | Rv0068 |
| 423 | D138 | [—] MV D92 | 2808725 | Oxidoreductase | — | Rv0068 |
| 202 | [—] | C176 | 1552591 | Conserved hypothetical hypothetical 27.6 kDa protein | — | Rv0036c |
| 566 | [—] | C71 | 127271 | Immunogenic MPB64/MPT64 (antigen MPB64/MPT64) | mpt64 | Rv1980c | b) Comparison *M. tuberculosis* H37Rv CP ↔ *M. tuberculosis* Erdman CP

| No | H37Rv CP | Erdman CP | NCBI AccNo | Name | Short-name | Rv-name |
|---|---|---|---|---|---|---|
| 117 | A132 | [—] | 231985 | L-Alanine dehydrogenase (40 kD antigen) | ald | Rv2780 |
| 119 | D96 | [—] | | Not identified | | |
| 122 | E151 | [—] | | Not identified | | |
| 179 | D92 | [—] MV D100 | 2808725 | Oxidoreductase | — | Rv0068 |
| 305 | [—] MV D92 | D100 | 2808725 | Oxidoreductase | — | Rv0068 |
| 195 | A320 | [—] | 1806192 | Protease IV, signal peptide peptidase | sppA | Rv0724 |
| 196 | A481 | [—] | 231985 | L-Alanine dehydrogenase (40 kD Antigen) | ald | Rv2780 |
| 234 | A386 [↓] | A511 [↑] | 2829813 | Acetylornithine aminotransferase (ACOAT) | argD | Rv1655 |
| 235 | B17 [↓] | A195 [↑] | 2829813 | Acetylornithine aminotransferase (ACOAT) | argD | Rv1655 |
| 199 | A267 | [—] MV A473 | 2791413 | Transcriptional regulator, MoxR homologue | moxR | Rv1479 |
| 232 | [—] MV A267 | A473 | 2791413 | Transcriptional regulator, MoxR homologue | moxR | Rv1479 |
| 200 | D10 | [—] | 2494371 | Haloalkane dehalogenase | — | Rv2296 |
| 233 | C376 [↓] | E192 [↑] | 1722951 | Hypothetical 18.2 kD protein CY373.03 | — | Rv1284 |
| 231 | [—] | D59 | 2072672 | Similar to Soj protein possible role in chromosome segregation | — | Rv3213c |

-continued

| No | H37Rv CP | Erdman CP | NCBI AccNo | Name | Short-name | Rv-name |
|---|---|---|---|---|---|---|
| 302 | C393 [↓] | C458 [↑] | 1839006 | Acetylglutamate kinase | argB | Rv1654 |
| 303 | D59 [↓] | D153 [↑] | 1731252 | Hypothetical 33.9 kD protein CY39.23C | — | Rv1996 |
| 304 | D28 [↓] | D20 [↑] | 3023331 | N-acetyl-γ-glutamyl-phosphate reductase | argC | Rv1652 |
| 306 | [—] | E84 | 2829592 | Hypothetical 16.0 kD protein CY441.11 | — | Rv2641 | c) Comparison *M. bovis* BCG Chicago CP ↔ *M. bovis* BCG Copenhagen CP

| No | Chicago CP | Copenhagen CP | NCBI AccNo | Name | Short-name | Rv-name |
|---|---|---|---|---|---|---|
| 67 | F12 | [—] | 1524194 | Conserved hypothetical | — | Rv0968 |
| 191 | D99 [↑] | D3 [↓] | 2104386 | Probable neuraminidase | — | Rv3463 |
| 192 | D122 [↑] | D82 [↓] | 2104386 | Probable neuraminidase | — | Rv3463 | d) Comparison *M. bovis* BCG Chicago CP ↔ *M. tuberculosis* Erdman CP

| No | Chicago CP | Erdman CP | NCBI AccNo | Name | Short-name | Rv-name |
|---|---|---|---|---|---|---|
| 11 | A8 | [—] MV A473 | 2791413 | Transcriptional regulator MoxR homologue | moxR | Rv1479 |
| 232 | [—] MV A8 | A473 | 2791413 | Transcriptional regulator, MoxR homologue | moxR | Rv1479 |
| 81 | A91 | [—] MV A226 | 1542900 | S-adenosylmethionine synthase | metK | Rv1392 |
| 209 | C645 | [—] MV C336 | 1524210 | Succinyl-CoA synthase α chain | sucD | RV0952 |
| 210 | C126 | [—] MV C143 | 1694860 | Oxidoreductase of aldo/keto reductase family | — | Rv2971 |
| 236 | [—] MV C126 | C143 | 1694860 | Oxidoreductase of aldo/keto reductase family | — | Rv2971 |

Table 3: Intensity Variants Identified on 2-DE Patterns of *M. bovis* BCG Chicago and *M. tuberculosis* H37Rv.

| No | BCG Chic CP | H37Rv CP | NCBI AccNo | Name | Short-name | Rv-name | Status |
|---|---|---|---|---|---|---|---|
| 28 | E54 [↑] | E42 [↓] | 585892 | 50 S Ribosomal protein L7/L12 | rplL | Rv0652 | Compare Copenhagen-H37Rv |
| 42 | D91 [↑] | D54 [↓] | 2127455 | Member of AhpC/TSA family | ahpD | Rv2429 | Compare Copenhagen-H37Rv |
| 43 | C31 [↑] | C53 [↓] | 2127453 | Alkyl hydroperoxide reductase chain C | ahpC | Rv2428 | Compare Copenhagen-H37Rv |
| 86 | E122 [↑] | E137 [↓] | 2909628 | Hypothetical protein MTV039.07 | — | Rv0569 | Compare Copenhagen-H37Rv |
| 89 | D46 [↑] | D9 [↓] | 1731190 | Hypothetical 21.5 kD protein CY20G9.01 precursor; possible exported protein | — | Rv0475 | Compare Copenhagen-H37Rv |
| 130 | C521 [↑] | A228 [↓] | | Not identified | | | Compare Copenhagen H37Rv |

-continued

| No | BCG Chic CP | H37Rv CP | NCBI AccNo | Name | Short-name | Rv-name | Status |
|---|---|---|---|---|---|---|---|
| 191 | D99 [↑] | D64 [↓] | 2104386 | Probable neuraminidase | — | Rv3463 | Compare Copenhagen-H37Rv |
| 192 | D122 [↑] | D78 [↓] | 2104386 | Probable neuraminidase | — | Rv3463 | Compare Copenhagen-H37Rv |
| 193 | C226 [↑] | C234 [↓] | 1781160 | Contains aminotransferase class-II pyridoxal-phosphate attachment site | — | Rv3054c | Compare Copenhagen-H37Rv |
| 162 | C155 [↑] | C151 [↓] | | Not identified | | | Compare Copenhagen-H37Rv |

TABLE 4

Differentially expressed proteins between the virulent strains of *M. tuberculosis* and *M. bovis* BCG (+/− variants):
Comparison *M. bovis* BCG Chicago CP ←→ *M. tuberculosis* H37Rv CP ←→ *M. bovis* BCG Copenhagen CP ←→ *M. tuberculosis* Erdman CP

| No | BCG Chicago CP | BCG Copenhagen CP | H37Rv CP | Erdman CP | NCBI AccNo | Protein name | Short-name | Rv-name |
|---|---|---|---|---|---|---|---|---|
| Xx2 | — | — | A187 | A509 | 2181962 | Elongation factor G | FusA2 | Rv0120c |
| Xx4 | — | — | C236 | C271 | 1709963 | Uridylate kinase | PyrH | Rv2883c |
| Xx6 | — | — | C608 | C523 | 2791397 | ABC-type transporter | — | Rv1463 |
| Xx7 | — | — | C416 | C487 | 1781191 | Short chain dehydro-genase/reductase family | — | Rv1856c |
| Xx9 | — | — | C278 | C315 | 1478233 | 1,3,4,6-tetrachloro-1,4,-cyclohexadiene hydrolase | LinB | Rv2579 |
| Xx10 | — | — | C407 Lower part | C474 Lower part | 2500011 | Phosphoribosylamino-imidazole carboxylase catalytic subunit | PurE | Rv3275c |
| Xx11 | — | — | C144 | C2 | 2496493 | Hypothetical protein | — | Rv2557 |
| Xx13 | — | — | F52 | F44 | 2496475 | Hypothetical protein | — | Rv3407 |
| Xx1 | — | — | A607 | A148 | 2960233 | Hypothetical protein | — | Rv3881c |
| Xx3 | — | — | B69 | B54 | 2791489 | Hypothetical protein | — | Rv2449c |
| Xx5 | — | — | C176 | C404 | 1552591 | Hypothetical protein | — | Rv9936c |
| Xx8 | — | — | C434 | C508 | 1731241 | Hypothetical protein | — | Rv2005c |
| Xx12 | — | — | D12 | D115 | 2960100 | Transcriptional regulator(Crp/Fnr family) | — | Rv3676 |
| | — | — | D115 | D130 | | | | |

The invention claimed is:

1. An isolated or purified nucleic acid molecule coding for a protein selected from the group consisting of oxidoreductase (Rv0068) (SEQ ID NO: 1) from *M. tuberculosis*, hypothetical protein (Rv3407) (SEQ ID NO: 2) from *M. tuberculosis*, and a fusion protein comprising said Rv0068 or said Rv3407 protein or a combination of Rv0068 and Rv3407.

2. A composition comprising at least one nucleic acid molecule of claim 1.

3. A composition comprising a nucleic acid molecule of claim 1, wherein said composition is a pharmaceutical composition further comprising a pharmaceutically acceptable carrier.

4. The composition of claim 3, wherein said composition is a vaccine.

5. A composition comprising a nucleic acid molecule of claim 1, wherein said composition is a diagnostic composition further comprising suitable means for detection.

6. A method for the production of a vaccine against a virulent strain of the *M. tuberculosis* comprising the steps of:
  (a) recombinantly expressing a differentially expressed protein selected from the group consisting of oxidoreductase (Rv0068) (SEQ ID NO: 1) from *M. tuberculosis*, hypothetical protein (Rv3407) (SEQ ID NO: 2) from *M. tuberculosis*, or a fusion protein comprising said protein, and
  (b) combining said recombinantly expressed protein, or said fusion protein with a pharmaceutically acceptable carrier.

7. A method for the production of a vaccine against a virulent strain of *M. tuberculosis* comprising combining a vector comprising a nucleic acid molecule of claim 1 with a biologically acceptable carrier, wherein said nucleic acid molecule in said vector is placed under the control of an expression control sequence.

8. A method of preventing, ameliorating or treating tuberculosis induced by *M. tuberculosis* in a subject in need thereof comprising administering an effective amount of the vaccine of claim 4 to the subject.

9. A method of detecting the presence of *M. tuberculosis* in a sample, comprising contacting the composition of claim 5 with a sample suspected of containing *M. tuberculosis*, and detecting the presence of a polynucleotide coding for a protein selected from the group consisting of oxidoreductase (Rv0068) (SEQ ID NO: 1) from *M. tuberculosis*, hypothetical protein (Rv3407) (SEQ ID NO: 2) from *M. tuberculosis*, and a fusion protein comprising Rv0068, Rv3407, or a combination of Rv0068 and Rv3407 in the sample.

10. The method of claim 9, wherein said detection is indicative of tuberculosis.

11. An isolated or purified nucleic acid molecule coding for hypothetical protein (Rv3407) (SEQ ID NO: 2) from *M. tuberculosis*, or a fusion protein comprising said protein.

12. A composition comprising a nucleic acid molecule of claim 11, wherein said composition is a pharmaceutical composition further comprising a pharmaceutically acceptable carrier.

13. The composition of claim 12, wherein said composition is a vaccine.

14. An isolated or purified nucleic acid molecule coding for oxidoreductase (Rv0068) (SEQ ID NO: 1) from *M. tuberculosis*, or a fusion protein comprising said protein.

15. A composition comprising a nucleic acid molecule of claim 14, wherein said composition is a pharmaceutical composition further comprising a pharmaceutically acceptable carrier.

16. The composition of claim 15, wherein said composition is a vaccine.

* * * * *